United States Patent
Smitz et al.

(10) Patent No.: US 11,566,289 B2
(45) Date of Patent: *Jan. 31, 2023

(54) MARKER GENES FOR OOCYTE COMPETENCE

(71) Applicant: Vrije Universiteit Brussel, Brussels (BE)

(72) Inventors: Johan Smitz, Brussels (BE); Sandra Wathlet, Brussels (BE); Tom Adriaenssens, Brussels (BE)

(73) Assignee: Vrije Universiteit Brussel, Brussels (BE)

( * ) Notice: Subject to any disclaimer, the term of this patent is extended or adjusted under 35 U.S.C. 154(b) by 1052 days.

This patent is subject to a terminal disclaimer.

(21) Appl. No.: 16/040,059

(22) Filed: Jul. 19, 2018

(65) Prior Publication Data

US 2018/0327841 A1 Nov. 15, 2018

Related U.S. Application Data

(63) Continuation-in-part of application No. 14/768,578, filed as application No. PCT/EP2014/053164 on Feb. 18, 2014, now Pat. No. 10,053,733.

(30) Foreign Application Priority Data

Feb. 18, 2013 (EP) .................................... 13155633

(51) Int. Cl.
| | |
|---|---|
| *C12Q 1/6881* | (2018.01) |
| *G16B 25/10* | (2019.01) |
| *C12Q 1/6883* | (2018.01) |
| *C12N 5/075* | (2010.01) |
| *C12N 5/071* | (2010.01) |
| *G16B 40/20* | (2019.01) |
| *G16B 20/00* | (2019.01) |
| *G16B 25/00* | (2019.01) |

(52) U.S. Cl.
CPC ......... *C12Q 1/6881* (2013.01); *C12N 5/0609* (2013.01); *C12N 5/0682* (2013.01); *G16B 20/00* (2019.02); *G16B 25/10* (2019.02); *G16B 40/20* (2019.02); *C12N 2501/11* (2013.01); *C12N 2501/31* (2013.01); *C12Q 1/6883* (2013.01); *C12Q 2600/124* (2013.01); *C12Q 2600/158* (2013.01); *G16B 25/00* (2019.02)

(58) Field of Classification Search
None
See application file for complete search history.

(56) References Cited

FOREIGN PATENT DOCUMENTS

| WO | 2011/000805 A1 | 1/2011 |
| WO | 2011/057411 A1 | 5/2011 |
| WO | 2012/109326 A2 | 8/2012 |

OTHER PUBLICATIONS

Sandra Wathlet et al.—"New candidate genes to predict pregnancy outcome in single embryo transfer cycles when using cumulus cell gene expression". Fertility and Sterility, Elsevier science, vol. 98, No. 2, May 3, 2012, pp. 432-439, New York, NY.
Sandra Wathlet et al., "Cumulus cell gene expression predicts better cleavage-stage embryo or blastocyst development and pregnancy for ICSI patients", Human Reproduction, vol. 26, No. 5, Mar. 3, 2011, XP055067465, pp. 1035-1051.
Zamalou Gisele Ouandaogo et al.—"Human Cumulus Cells Molecular Signature in Relation to Oocyte Nuclear Maturity Stage", PLOS One, vol. 6, No. 11, Nov. 7, 2011, XP055066991.
Hamel Melanie et al.—"Genomic assessment of follicular marker genes as pregnancy predictors for human IVF", Molecular Human Reproduction, Oxford Press, vol. 16, No. 2, Feb. 1, 2010, pp. 87-96, England.
Kathryn Michelle Gebhardt et al.—"Human cumulus cell gene expression as a biomarker of pregnancy outcome after single embryo transfer", Fertility and Sterility, vol. 96, No. 1, Jul. 1, 2011, XP055067464, pp. 47-52, New York, NY.
T. Adriaenssens et al.—"Cumulus cell gene expression is associated with oocyte developmental quality and influenced by patient and treatment characteristics", Human Reproduction, vol. 25, No. 5, Mar. 13, 2010, pp. 1259-1270, XP055066622.
Bitton Danny A. et al.—"Exon level integration of proteomics and microarray data", BMC Bioinformatics, Biomed Central, vol. 9, No. 1, Feb. 25, 2008, p. 118, London, GB, XP02131682.
A.A. Pohl et al.—"Affy Exxon tissues: exon levels in normal tissues in human, mouse and rat", Bioinformatics, vol. 25, No. 18, Jul. 1, 2009, pp. 2442-2443, XP055119461.
International Search Report and Written Opinion pertaining to Application No. PCT/EP2014/053164 with an international filing date of Feb. 18, 2014.

*Primary Examiner* — Olivia M. Wise
(74) *Attorney, Agent, or Firm* — Dinsmore & Shohl LLP

(57) ABSTRACT

Cumulus cell (CC) gene expression is being explored as an additional method to morphological scoring to choose the embryo with the highest chance to pregnancy. The present invention relates to a novel method of identifying biomarker genes for evaluating the competence of a mammalian oocyte in giving rise to a viable pregnancy after fertilization, based on the use of live birth and embryonic development as endpoint criteria for the oocytes to be used in an exon level analysis of potential biomarker genes. The invention further provides CC-expressed biomarker genes thus identified, as well as prognostic models based on the biomarker genes identified using the methods of the present invention.

7 Claims, 15 Drawing Sheets

Specification includes a Sequence Listing.

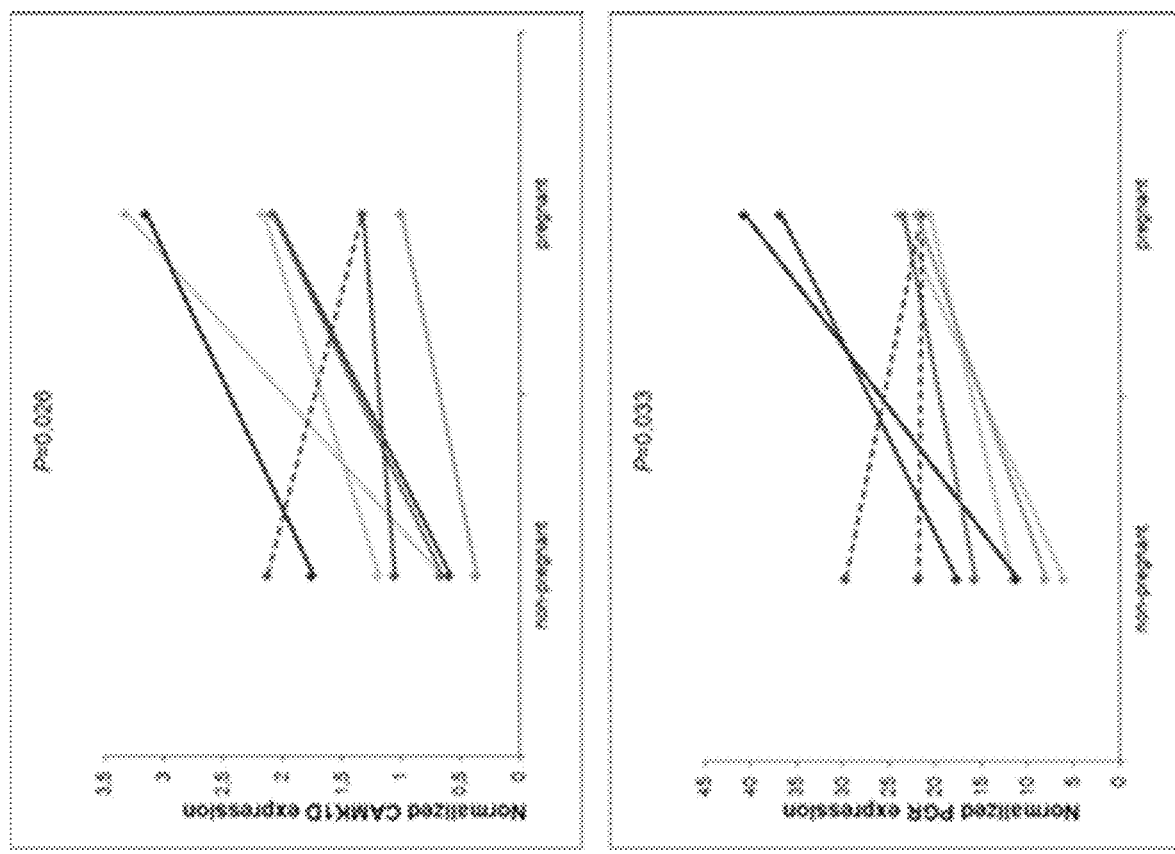

SEQUENCE LISTING

<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Forward Primer GPX3/Other DNA

<400> SEQUENCE: 1
ggggacaaga gaagtcgaag a      21

<210> SEQ ID NO 2
<211> LENGTH: 20
<212> TYPE: DNA
<213> ORGANISM: Artificial Sequence
<220> FEATURE:
<223> OTHER INFORMATION: Reverse Primer GPX3/Other DNA

<400> SEQUENCE: 2
gccagcatac tgcttgaagg      20

<210> SEQ ID NO 3
<211> LENGTH: 20
<212> TYPE: DNA
<213> ORGANISM: Artificial Sequence
<220> FEATURE:
<223> OTHER INFORMATION: Forward Primer GSR/Other DNA

<400> SEQUENCE: 3
caatgatcag caccaactgc      20

<210> SEQ ID NO 4
<211> LENGTH: 24
<212> TYPE: DNA
<213> ORGANISM: Artificial Sequence
<220> FEATURE:
<223> OTHER INFORMATION: Reverse Primer GSR/Other DNA

<400> SEQUENCE: 4
agtcttttta acctccttga cctg      24

```
<210> SEQ ID NO 5
<211> LENGTH: 20
<212> TYPE: DNA
<213> ORGANISM: Artificial Sequence
<220> FEATURE:
<223> OTHER INFORMATION: Forward Primer GSTA3/Other DNA

<400> SEQUENCE: 5
gatgccaaga ttgccttgat                                               20

<210> SEQ ID NO 6
<211> LENGTH: 22
<212> TYPE: DNA
<213> ORGANISM: Artificial Sequence
<220> FEATURE:
<223> OTHER INFORMATION: Reverse Primer GSTA3/Other DNA

<400> SEQUENCE: 6
ttgtccatgg ctctgtaaca ct                                            22

<210> SEQ ID NO 7
<211> LENGTH: 21
<212> TYPE: DNA
<213> ORGANISM: Artificial Sequence
<220> FEATURE:
<223> OTHER INFORMATION: Forward Primer GSTA4/Other DNA

<400> SEQUENCE: 7
cctcaaggag agaaccctga t                                             21

<210> SEQ ID NO 8
<211> LENGTH: 21
<212> TYPE: DNA
<213> ORGANISM: Artificial Sequence
<220> FEATURE:
<223> OTHER INFORMATION: Reverse Primer GSTA4/Other DNA

<400> SEQUENCE: 8
ggatgcatga taagcagttc c                                             21

<210> SEQ ID NO 9
<211> LENGTH: 18
<212> TYPE: DNA
<213> ORGANISM: Artificial Sequence
<220> FEATURE:
<223> OTHER INFORMATION: Forward Primer ITPR1/Other DNA

<400> SEQUENCE: 9
tacccagcgg ctgctaac                                                 18

<210> SEQ ID NO 10
<211> LENGTH: 20
<212> TYPE: DNA
<213> ORGANISM: Artificial Sequence
<220> FEATURE:
<223> OTHER INFORMATION: Reverse Primer ITPR1/Other DNA

<400> SEQUENCE: 10
tgcaaatcct gctcctctgt                                               20

<210> SEQ ID NO 11
<211> LENGTH: 20
<212> TYPE: DNA
<213> ORGANISM: Artificial Sequence
<220> FEATURE:
<223> OTHER INFORMATION: Forward Primer PGR/Other DNA
```

```
<400> SEQUENCE: 11
gtcatagacc cccgttgcta                                                  20

<210> SEQ ID NO 12
<211> LENGTH: 20
<212> TYPE: DNA
<213> ORGANISM: Artificial Sequence
<220> FEATURE:
<223> OTHER INFORMATION: Reverse Primer GPR/Other DNA

<400> SEQUENCE: 12
gtcatagacc cccgttgcta                                                  20

<210> SEQ ID NO 13
<211> LENGTH: 19
<212> TYPE: DNA
<213> ORGANISM: Artificial Sequence
<220> FEATURE:
<223> OTHER INFORMATION: Forward Primer SLC2A1/Other DNA

<400> SEQUENCE: 13
gtctggcatc aacgctgtc                                                   19

<210> SEQ ID NO 14
<211> LENGTH: 18
<212> TYPE: DNA
<213> ORGANISM: Artificial Sequence
<220> FEATURE:
<223> OTHER INFORMATION: Reverse Primer SLC2A1/Other DNA

<400> SEQUENCE: 14
acgataccgg agccaatg                                                    18

<210> SEQ ID NO 15
<211> LENGTH: 18
<212> TYPE: DNA
<213> ORGANISM: Artificial Sequence
<220> FEATURE:
<223> OTHER INFORMATION: Forward Primer TGFB1/Other DNA

<400> SEQUENCE: 15
agtggttgag ccgtggag                                                    18

<210> SEQ ID NO 16
<211> LENGTH: 20
<212> TYPE: DNA
<213> ORGANISM: Artificial Sequence
<220> FEATURE:
<223> OTHER INFORMATION: Reverse Primer TGFB1/Other DNA

<400> SEQUENCE: 16
gcagtgtgtt atccctgctg                                                  20

<210> SEQ ID NO 17
<211> LENGTH: 19
<212> TYPE: DNA
<213> ORGANISM: Artificial Sequence
<220> FEATURE:
<223> OTHER INFORMATION: Forward Primer THBS1/Other DNA

<400> SEQUENCE: 17
aatgctgtcc tcgctgttg                                                   19

<210> SEQ ID NO 18
<211> LENGTH: 20
```

```
<212> TYPE: DNA
<213> ORGANISM: Artificial Sequence
<220> FEATURE:
<223> OTHER INFORMATION: Reverse Primer THBS1/Other DNA

<400> SEQUENCE: 18
gccacagctc gtagaacagg                                              20

<210> SEQ ID NO 19
<211> LENGTH: 347
<212> TYPE: DNA
<213> ORGANISM: Homo sapiens

<400> SEQUENCE: 19
gtggggagga gcacgtgttt gagaattcgc cggtcctgga tgaacggtcc gccctctact    60
ctggcgtgca caagaagccc cttttctttg atggctctcc tgagaaacct cccgaagatg   120
actcagactc tctcaccacg tctccatcct ccagcagcct ggacacctgg ggggctggcc   180
ggaagttggt caaaaccttc agcaaaggag agagccgggg cctgattaag cccccaaga   240 agatggggac attcttctcc tacccagaag aagaaaaggc ccagaaagtg tcccgctccc   300
tcaccgaggg ggagatgaag aagggtctcg ggtccctaag ccacggg               347

<210> SEQ ID NO 20
<211> LENGTH: 211
<212> TYPE: DNA
<213> ORGANISM: Homo sapiens

<400> SEQUENCE: 20
agaaaccctc ataaagtaga tgcagagggc agtaagatat aactcaactt tgaaaatgtc    60
agccgttata gttgaagaaa tctgacccaa gagacttcgc tccgctgcaa gatggaagga   120
agcttaagta agacataaat ttgtaatgaa cttgctcaca acatccgccg ccactgtgac   180
ttgcagtcat catccattac cacaaaatta g                                  211

<210> SEQ ID NO 21
<211> LENGTH: 77
<212> TYPE: DNA
<213> ORGANISM: Homo sapiens

<400> SEQUENCE: 21
ttgcaggatg gctactcgta tccctccaca catgatcatc agtatttgcc tcctgtgtcc    60
caaccggcct gagtcaa                                                  77

<210> SEQ ID NO 22
<211> LENGTH: 369
<212> TYPE: DNA
<213> ORGANISM: Homo sapiens

<400> SEQUENCE: 22
aagaaagtag cagaaagtga ggctggcagg cggcggcaaa ggagccggcg cgcggcggcg    60
gcaggaagtc tgtgcccgag aacagcagaa ataagagcca gggagggacc gcggccgcgg   120
cggcggcggc gagagcgaaa gaggaaactg cagaggagga agctgcgccg cagcccgagc   180
cgcccggcat cccccgccgcc tctgcgcccg cgccgcgccc ccggcgcccc ctccccagcg   240
cgcccccggc cgctcctccg cgccgcgctc gtcggccatg gcccgggaga acggcgagag   300
cagctcctcc tggaaaaagc aagctgaaga catcaagaag atcttcgagt tcaaagagac   360
cctcggaac                                                          369
```

<210> SEQ ID NO 23
<211> LENGTH: 79
<212> TYPE: DNA
<213> ORGANISM: Homo sapiens

<400> SEQUENCE: 23
caaaagactt cattcggaac ctgatggaga aggacccgaa taaaagatac acgtgtgagc    60
aggcagctcg gcacccatg                                                79

<210> SEQ ID NO 24
<211> LENGTH: 139
<212> TYPE: DNA
<213> ORGANISM: Homo sapiens

<400> SEQUENCE: 24
gcaggaggaa gttaccgtgc gctggcagag gctccttcag catctacagg gacagaggaa    60
gcaggtggca gacatgcagg ctgtgctgag cctgctgcag gaggtggagg ctgcctccca   120
ccagctggag gagctgcag                                                139

<210> SEQ ID NO 25
<211> LENGTH: 138
<212> TYPE: DNA
<213> ORGANISM: Homo sapiens

<400> SEQUENCE: 25
gtatgcccag gatgccctga gagttctgct gaattgttct ggactgcaac aggtggatat    60
tactctaatg aaggagaatt tctgggacca gttatctgaa gatctgtgtt actatcatgg   120
agtctgcttt attgctaa                                                 138

<210> SEQ ID NO 26
<211> LENGTH: 505
<212> TYPE: DNA
<213> ORGANISM: Homo sapiens

<400> SEQUENCE: 26
tgagtaaatg ccgcagattc tggaaagttc tgatcagtgc gatacataag gctgaggaag    60
tgggacctcc cctttgggt cggtagttca gcgccggcgc cggtgtgcga gccgcggcag   120
agtgaggcag gcaacccgag gtgcggagcg acctgcggag gctgagcccc gctttctccc   180
agggtttctt atcagccagc cgccgctgtc cccggggag taggaggctc ctgacaggcc   240
gcggctgtct gtgtgtcctt ctgagtgtca gaggaacggc cagaccccgc gggcggagc   300 agaacgcggc cagggcagaa agcggcggca ggagaagcag gcaggggcc ggaggacgca   360 gaccgagacc cgaggcggag gcggaccgcg agccggccat gtcggtggtg gggttggacg   420
tgggctcgca gagctgctac atcgcggtag cccgggccgg gggcatcgag accatcgcca   480
atgagttcag cgaccggtgc acccc                                         505

<210> SEQ ID NO 27
<211> LENGTH: 2005
<212> TYPE: DNA
<213> ORGANISM: Homo sapiens

<400> SEQUENCE: 27
gtcccctcct tctttacaga tgctgagagg cgatctgtgt tagatgctgc acagattgtt    60
ggcctaaact gtttaagact tatgaatgac atgcagctg gtaaggaaaa ggcatttgtg   120
tggaagtgaa tatactatca gaactaaaga tgttctcagt gctattactt tcttatagat   180

```
acagaaacac agcctgttaa aaagtcaagt cagatttgaa acaaaagtc tacctcttaa         240 aatgcttatg gttaatgaga aattggtatt ttatcaaact tatgaatctg ctttcattag         300
agaattcttt tcatgttttt taatcctttg aaaatgtagg ttggatttag ctttgtttcc         360
ttacattgca tttatagtta ggaagcaatt tttcccacaa tcttaaaatt ctgggcttca         420
aaactacctt ggcttataag taaatgattt agtttaaaaa atttttttt atctactgaa          480 ctgtagatag gtgatcattt atcaaatatt gctttaagcc tgtactattt gaatgtgtta         540
ggctaggtat tgtggatata cagaggtgat tacagcatct cttcttgag cttttggtag          600 tttattatga ttacagatga acaaaaaatc agttaaggaa aaaaatcagt ttttatgctg         660
aaaagtttta ctcatatttc tgttaggttt ttggaaaact gttaaatatt ggtaaaaata         720 tgttttagg tatacatgtt tagaaataca gttgtttaaa gttcagaaaa aaactttta           780 aggttgatca gctatttagc tcagatctaa aaattggtag gaactatagt tgctgtagtt         840
gtatattaaa ttcttaattt ttttggataa gcggtgtcct agcaggttgt ggttaaaatg         900
taagtattgc ataatgagtc tgatactgtc tgtgatacgt ggttatgttt cactgtattc         960
acgccatatg ttttgtctag cacatctcca tatattgaaa agtgatagag cattgttctg        1020
aaatcagaaa gagagtaata attaattcca agaaaatcag tgtgaagtca ggtataaaag        1080
gaatgtaatg tgttcacctt taattgtttc aagttaatag tcaagcttcc tgcatgtgta        1140
attttatgta acagtgagat tcctaagaaa atgtgaacca agaattgaa acatacttat         1200 tttttgtagt tgctttgaat tacgaaattt ataagcagga tctcccaagc ctggatgaga        1260
aacctcggat agtggttttt gttgatatgg gacattcagc ttttcaagtg tctgcttgtg        1320
cttttaacaa gggaaaattg aaggtaaagt catacattgg aactcagtgt ccaaaacacg        1380
ttaagtgttg tgactttaag ctactgagcc tctttactag gcttttctt cttggtaatg         1440 aagagtttta ttttaggtaa agatgttaac aggaaacggt tgctaaggtt gagctccata        1500
aagatgatgt aattgtctta gcatactctt aagtgttctt gtttaggaaa gaaaaggctt        1560
tttacagtta ttttctatgt agtcatttaa aagtcaaaaa tatcttagag atttattcct        1620
gactgatttg gatttcatgt tataatttaa atatagtctt gagtctctta gtctttcatt        1680
gtttgagtag taatatttaa gattctagtt acaaatgtga ttgaaaataa ccagactatt        1740
tgttgtttca accaaattag gtactgggaa cagcttttga tcctttctta ggaggaaaaa        1800
acttcgatga aaagttagtg gaacattttt gtgcagaatt taaaactaag tacaagttgg        1860
atgcaaaatc caaaatacga gcactcctac gtctgtatca ggaatgtgaa aaactgaaaa        1920
agctaatgag ctctaacagc acagaccttc cactgaatat cgaatgcttt atgaatgata        1980
aagatgtttc cggaaagatg aacag                                              2005

<210> SEQ ID NO 28
<211> LENGTH: 185
<212> TYPE: DNA
<213> ORGANISM: Homo sapiens

<400> SEQUENCE: 28
catttgtaat cagtacagcc acatcgcaga caaagtcagt gaggttcctg ccaacactaa          60
ggagctggta tccctcattg aattcctaaa gaaatccagt gctgtcactg tgttcaaact         120
caggaggcaa cttagagatg caagtgaacg gctggagttc ctgatggact atgcagactt         180
gccgt                                                                    185
```

<210> SEQ ID NO 29
<211> LENGTH: 222
<212> TYPE: DNA
<213> ORGANISM: Homo sapiens

<400> SEQUENCE: 29

```
aacctgaagc gggtagctga gacctggatg gatgaatttg ccgagtacat ttaccagcgg      60
cggccggagt acaggcatct ctccacgggg gacatctctg cccagaagga gctgcgcaag     120
cagctcaagt gcaaggactt caaatggttc atggctgctg tggcctggga cgtgcctaaa     180
tactaccctc cagtggagcc cccgcctgct gcctgggggg ag                        222
```

MARKER GENES FOR OOCYTE COMPETENCE

CROSS-REFERENCE TO RELATED APPLICATIONS

This application is filed under 35 U.S.C. § 111 as a continuation-in-part of U.S. application Ser. No. 14/768,578 (File Reference VUB-001), filed Aug. 18, 2015, which is a U.S. National Stage Entry of International Patent Application No. PCT/EP2014/053164, filed on Feb. 18, 2014, which designates the United States and claims priority to European Patent Office Application No. 13155633.4, filed on Feb. 18, 2013, the contents of which are hereby incorporated by reference in their entirety.

FIELD OF THE INVENTION

Cumulus cell (CC) gene expression is being explored as an additional method to morphological scoring to choose the embryo with the highest chance to pregnancy. The present invention relates to a novel method of identifying biomarker genes for evaluating the competence of a mammalian oocyte in giving rise to a viable pregnancy after fertilization, based on the use of live birth and embryonic development as endpoint criteria for the oocytes to be used in an exon level analysis of potential biomarker genes. The invention further provides CC-expressed biomarker genes thus identified, as well as prognostic models based on the biomarker genes identified using the methods of the present invention.

BACKGROUND TO THE INVENTION

Single embryo transfer (SET) is the preferred treatment to limit multiple pregnancies after ART. In order not to compromise the carry home baby rate, the selection of the embryo for transfer in the first cycle becomes even more important. Next to the existing criterion based on morphology, other methods are currently under investigation. The use of quantitative gene expression measurements in cumulus cells (CC), which are in close contact with the oocyte during growth and maturation, seems a promising method (Huang and Wells 2010). Since the first published study on the subject where CC expression could be related to embryo development (McKenzie et al. 2004), several other studies have investigated this possibility and try to relate CC expression to different endpoints. Examples of endpoints investigated are: embryo development (Anderson et al. 2009; Cillo et al. 2007; Feuerstein et al. 2007; Hasegawa et al. 2005; van Montfoort et al. 2008; Zhang et al. 2005), aneuploidy stage of the oocyte (Fragouli et al. 2012b), oocyte nuclear maturity stage (Ouandaogo et al. 2011) and probably the most important from a patient perspective: pregnancy outcome (Assidi et al. 2011; Assou et al. 2008; Gebhardt et al. 2011; Wathlet et al. 2012; Wathlet et al. 2011). Confirmation of results between different studies does not seem obvious in the analysis of CC gene expression. In the current literature not many genes were found in common in different studies. For example, hyaluronan synthase 2 (HAS2) was higher expressed in good quality embryos compared to low embryo morphology in two studies (Cillo et al. 2007; McKenzie et al. 2004), but could not be related to embryo morphology in two other studies (Anderson et al. 2009; Gebhardt et al. 2011). Divergences can be due to a different experimental design, with different endpoints, but gene expression can be influenced by known factors such as the stimulation protocol of the patients (Adriaenssens et al. 2009; Adriaenssens et al. 2010; Grondahl et al. 2009) or not yet assessed factors such as culture media used in the different IVF laboratories.

In this study, 47 individual cumulus complexes from 47 Intra-cytoplasmic sperm injection (ICSI) patients were retrospectively analyzed with quantitative real-time polymerase chain reaction (QPCR). Using the current sample set, a pregnancy prediction model from a previous study (Wathlet et al. 2012) was validated for its predictive power. In a next step, in an attempt to search for new genes with a stronger predictive power, new multiparametric models were built considering the 3 genes (ephrin-B2 (EFNB2), calcium/calmodulin-dependent protein kinase ID (CAMK1D), stanniocalcin 1 (STC1)) described earlier and multiple novel genes and splice variants of said genes in mathematical models to predict the oocyte competence (see Tables).

Our patient sample set allowed for an analysis never reported before in literature: CC from oocytes that did not result in pregnancy in the fresh transfer cycle and the CC from their sibling oocytes that resulted in pregnancy after a frozen embryo transfer (FRET) cycle were analyzed (Intra-patient analysis). To our knowledge this is the first study to compare pregnant and non-pregnant CC from the same retrieval cycle in a SET setting as would be done in a final clinical application.

This figure represents the distribution of the samples used for the different analyses performed in this study. The grey background fields delimit the samples that were used for the specific analyses which are marked on the left side of the field. SET: single embryo transfer; FRET: frozen embryo transfer cycle; rFSH: recombinant Follicle Stimulating Hormone. [a]: (Wathlet et al. 2012).

A: Pregnancy analyses (inter-patient)

Validation of the pregnancy model from an earlier study[a] (EFNB2, CAMK1D and STC1)

t-test analyses pregnant vs non-pregnant

Building new pregnancy model with new genes

B: Pregnancy analyses (intra-patient)

Paired t-test pregnant vs non-pregnant

Testing the muliparametric models found in the inter-patient analyses

Figure 2A:
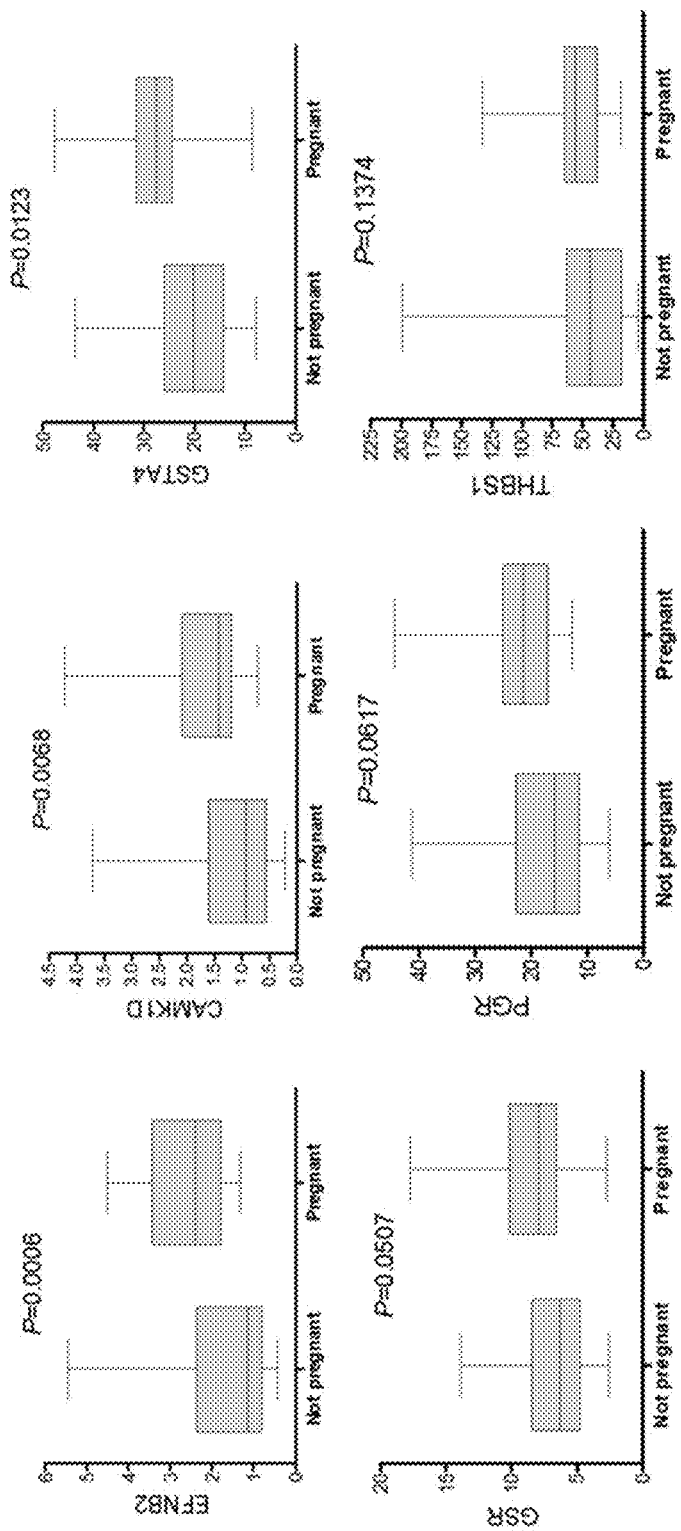

FIG. 2A: t-test of normalized gene expression values of non-pregnant versus live birth related cumulus cell samples.

The graphs represent the differences in gene expression between the cumulus cell samples associated to an oocyte that after in vitro fertilization treatment resulted in a live birth (n=19) or not (n=28). Normalization was done to the mean of B2M and UBC. Since multiple genes were tested, the Bonferroni correction allowed us to consider only P-values <0.0042 as significant. The total range of expressions found is depicted by the boxes and whiskers respectively representing the two inner and the two outer quartiles with centrally the median.

Figure 2B:
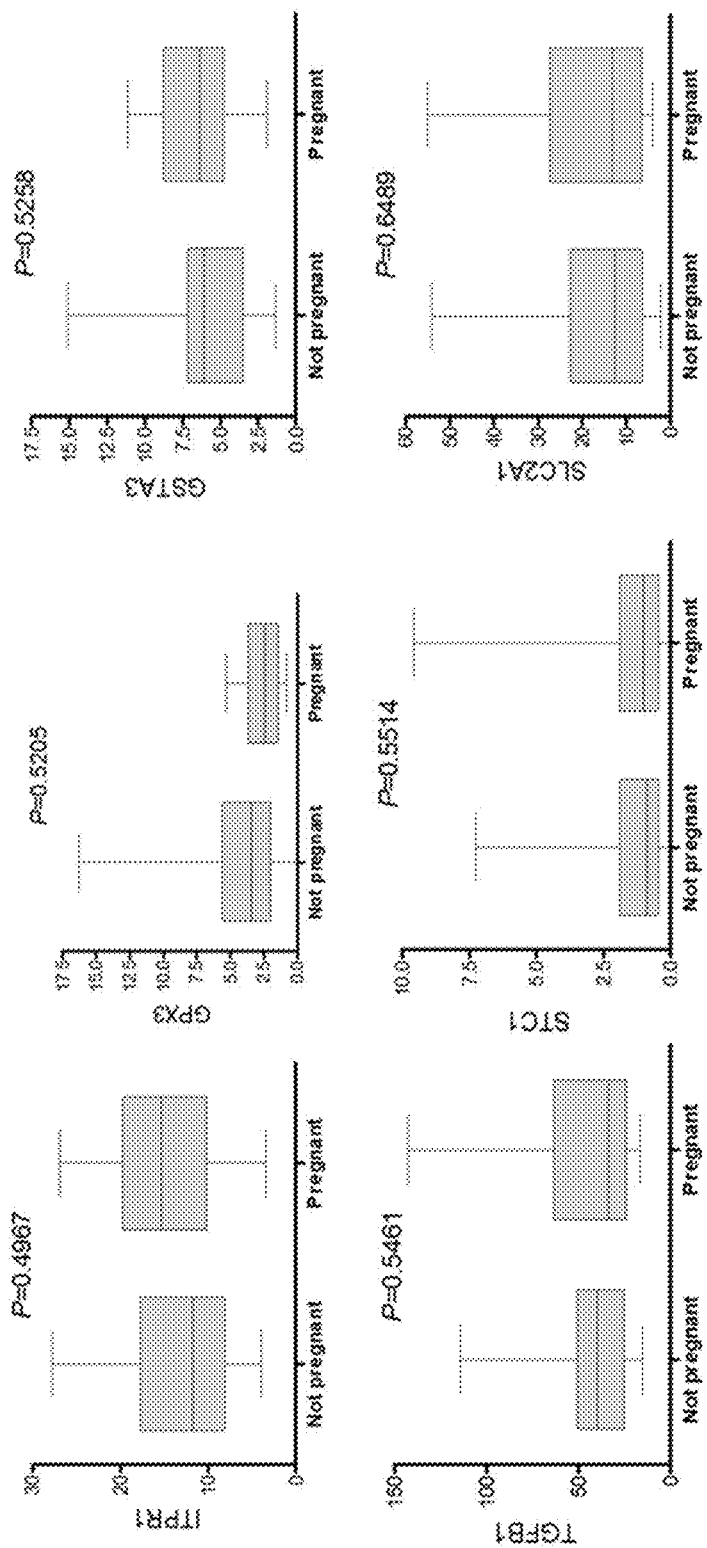

FIG. 2B: t-test of normalized gene expression values of non-pregnant versus live birth related cumulus cell samples.

The graphs represent the differences in gene expression between the cumulus cell samples associated to an oocyte that after in vitro fertilization treatment resulted in a live birth (n=19) or not (n=28). Normalization was done to the mean of B2M and UBC. Since multiple genes were tested, the Bonferroni correction allowed us to consider only P-values <0.0042 as significant. The total range of expressions found is depicted by the boxes and whiskers respectively representing the two inner and the two outer quartiles with centrally the median.

Figure 3:
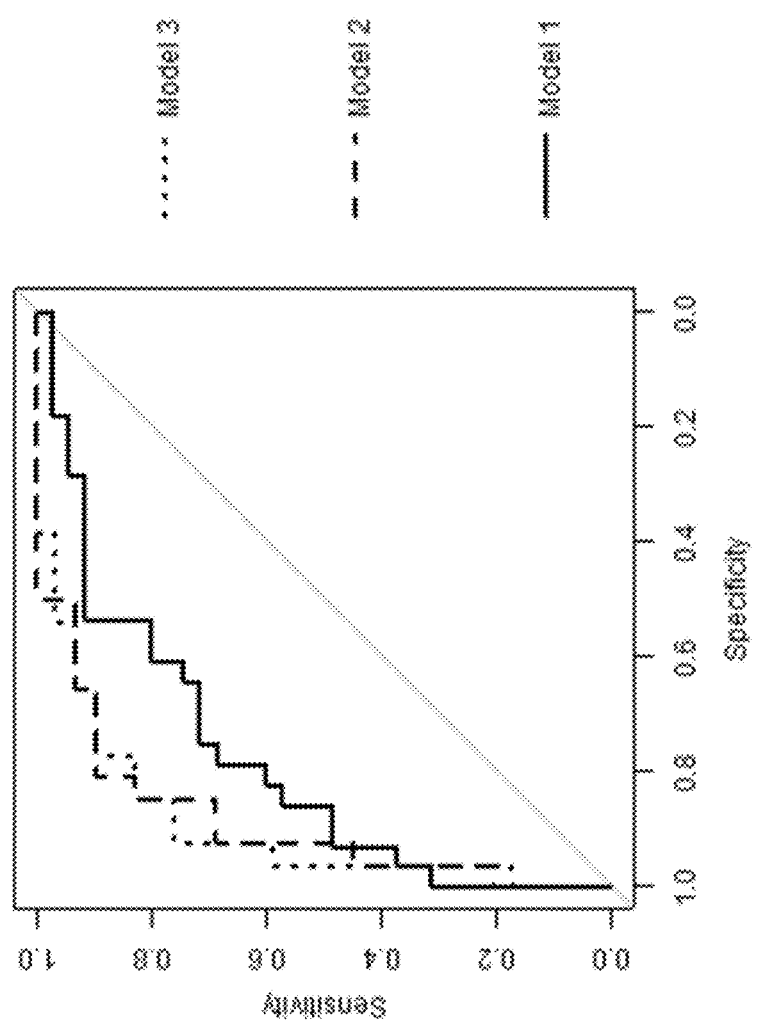

FIG. 3: Receiver operating characteristic (ROC) curve of the 3 pregnancy models.

Multiparametric models were built to predict the chance to pregnancy including the gene expression levels measured in cumulus cell samples associated to an oocyte that after in vitro fertilization treatment resulted in a live birth or not. For Model 3 patient and cycle characteristics were also included (from Table 3). Model 1 was limited to 3 genes and is composed of EFNB2, PGR and GSTA4. In Model 2 all genes were allowed into the model as long as they could improve the model. Five genes were retained for Model 2: EFNB2, PGR, GSTA4, GTSA3, GPX3. To try to improve Model 2, in Model 3 patient and cycle characteristics were allowed into the model if they could improve the P-value of the model: EFNB2, PGR, GSTA4, GTSA3, GPX3, age, Relative E2, and number of days of ovarian stimulation. The respective areas under the curve are 0.79, 0.89 and 0.90. Relative E2: E2 value measured on day of hCG over the number of cumulus oophorus complexes.

Figure 4A:
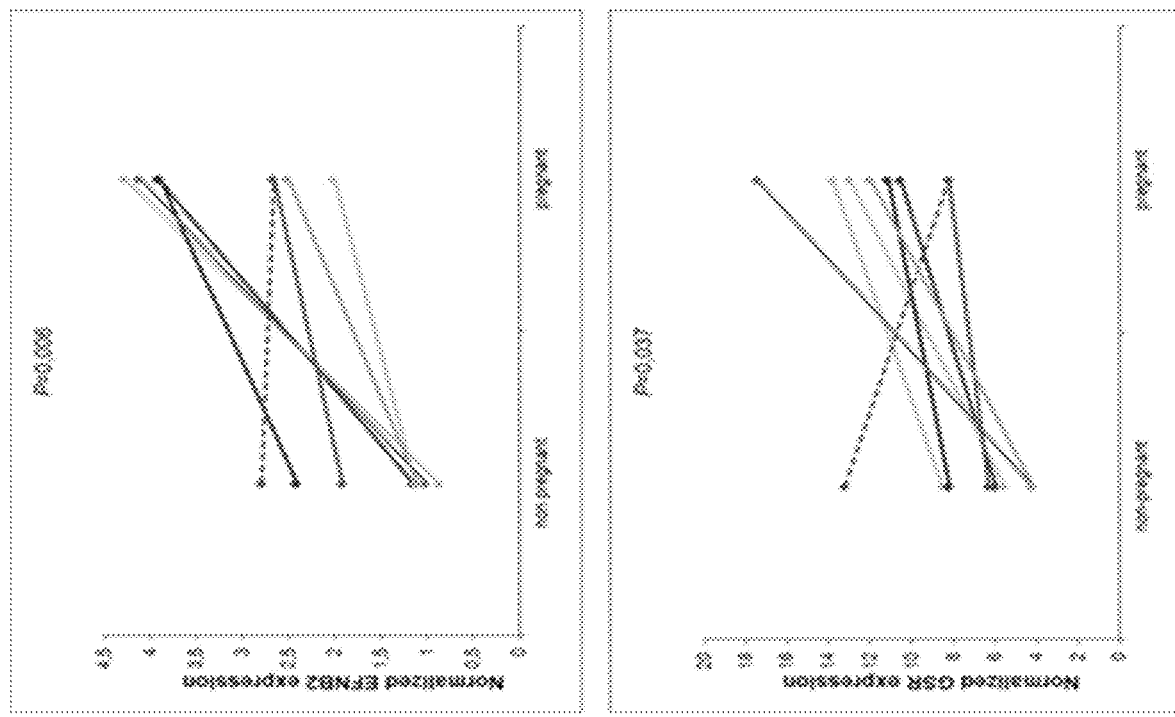

FIG. 4A: Paired t-test for the Intra-patient analysis pregnant versus non-pregnant.

The graphs compare for each patient the gene expression of a cumulus complex that corresponded to an oocyte that did not result in pregnancy to one that resulted in pregnancy in a subsequent single embryo frozen transfer cycle. Per patient the oocytes originate from one retrieval cycle. One patient had 2 consecutive frozen cycles, the first one not resulting in pregnancy. One color represents one patient. The dashed lines show (only in the graphs with a major trend: up or down from non-pregnant to pregnant with P<0.1) the pairs not following the major trend. Those pairs are also marked with '$a$' in Table 7.

Figure 4B:
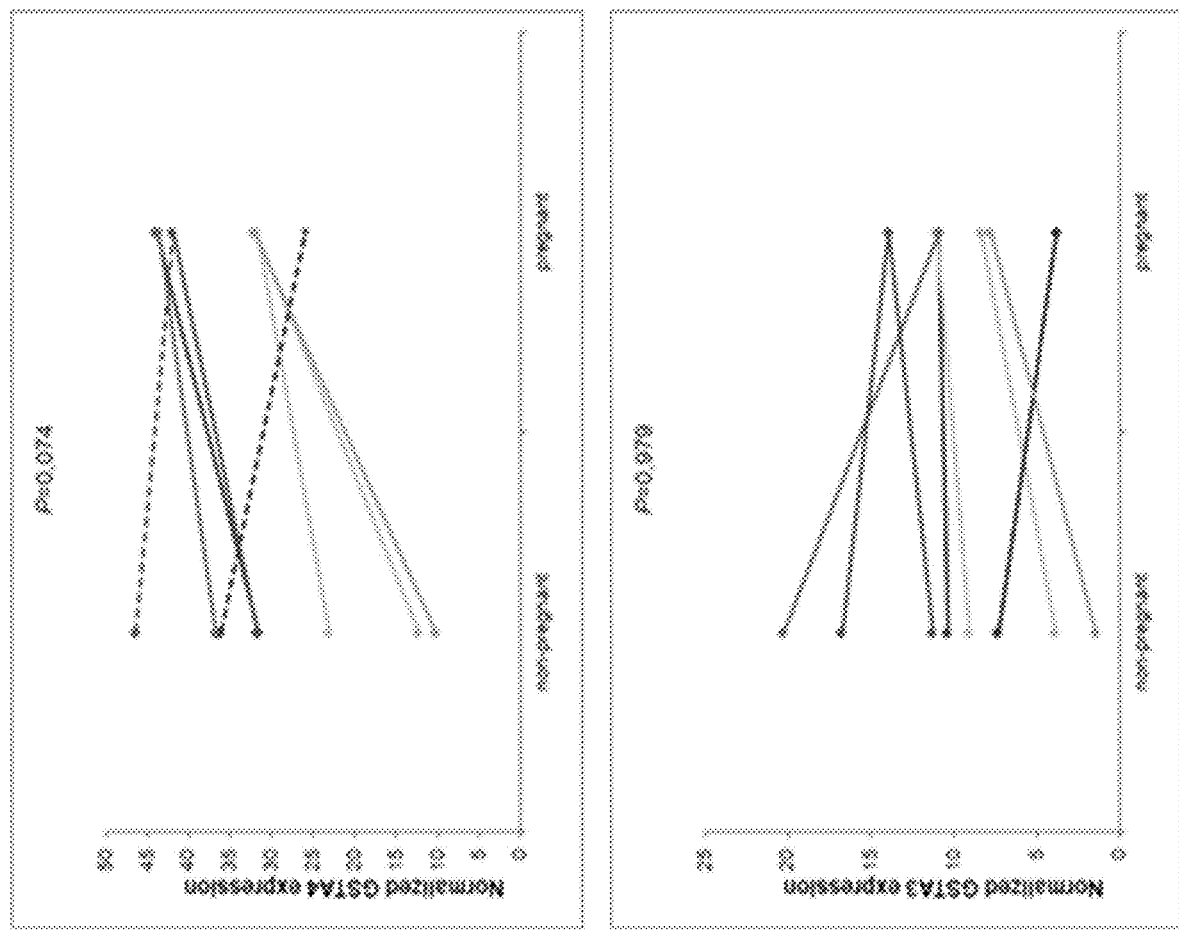

FIG. 4B: Paired t-test for the Intra-patient analysis pregnant versus non-pregnant.

The graphs compare for each patient the gene expression of a cumulus complex that corresponded to an oocyte that did not result in pregnancy to one that resulted in pregnancy in a subsequent single embryo frozen transfer cycle. Per patient the oocytes originate from one retrieval cycle. One patient had 2 consecutive frozen cycles, the first one not resulting in pregnancy. One color represents one patient. The dashed lines show (only in the graphs with a major trend: up or down from non-pregnant to pregnant with P<0.1) the pairs not following the major trend. Those pairs are also marked with '$a$' in Table 7.

FIG. 4C: Paired t-test for the Intra-patient analysis pregnant versus non-pregnant.

The graphs compare for each patient the gene expression of a cumulus complex that corresponded to an oocyte that did not result in pregnancy to one that resulted in pregnancy in a subsequent single embryo frozen transfer cycle. Per patient the oocytes originate from one retrieval cycle. One patient had 2 consecutive frozen cycles, the first one not resulting in pregnancy. One color represents one patient. The dashed lines show (only in the graphs with a major trend: up or down from non-pregnant to pregnant with P<0.1) the pairs not following the major trend. Those pairs are also marked with '$a$' in Table 7.

Figure 4D:
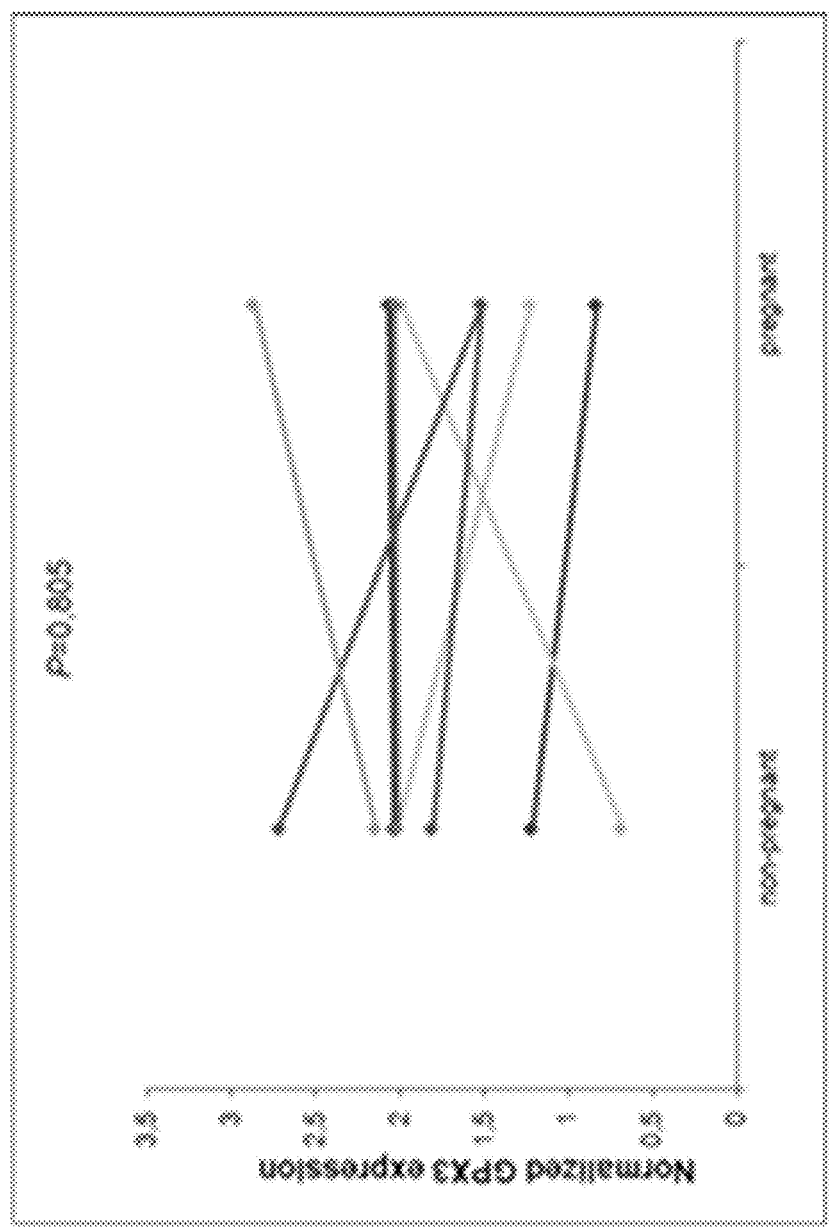

FIG. 4D: Paired t-test for the Intra-patient analysis pregnant versus non-pregnant.

The graphs compare for each patient the gene expression of a cumulus complex that corresponded to an oocyte that did not result in pregnancy to one that resulted in pregnancy in a subsequent single embryo frozen transfer cycle. Per patient the oocytes originate from one retrieval cycle. One patient had 2 consecutive frozen cycles, the first one not resulting in pregnancy. One color represents one patient. The dashed lines show (only in the graphs with a major trend: up or down from non-pregnant to pregnant with P<0.1) the pairs not following the major trend. Those pairs are also marked with '$a$' in Table 7.

Figure 5:
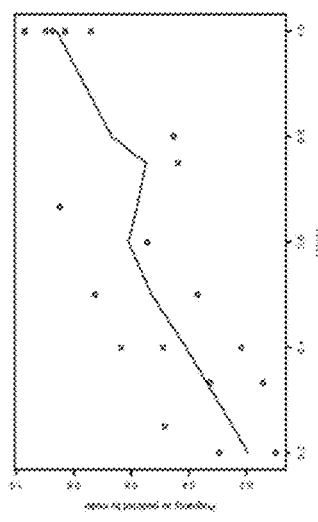
Figure 5:
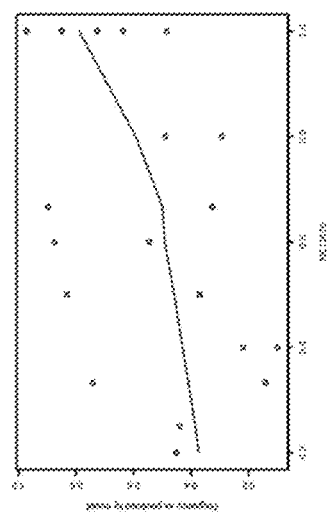
Figure 5:
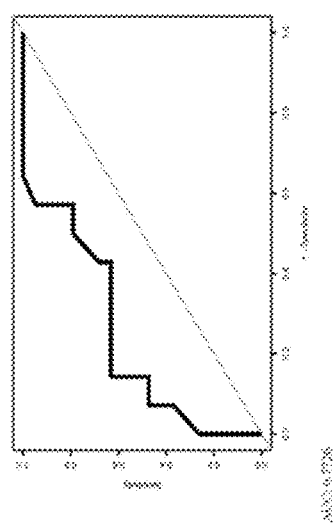

FIG. 5: The strongest model obtained with the intra-patient analysis predictive for pregnancy, AUC=Area under the curve. Formula: to predict the chance on pregnancy=3.23+2.57*EFNB2+1.87*NCOA7 p=0.0127. (a value of at least 0.5 refers to pregnancy, a lower value to no pregnancy)

Figure 6:
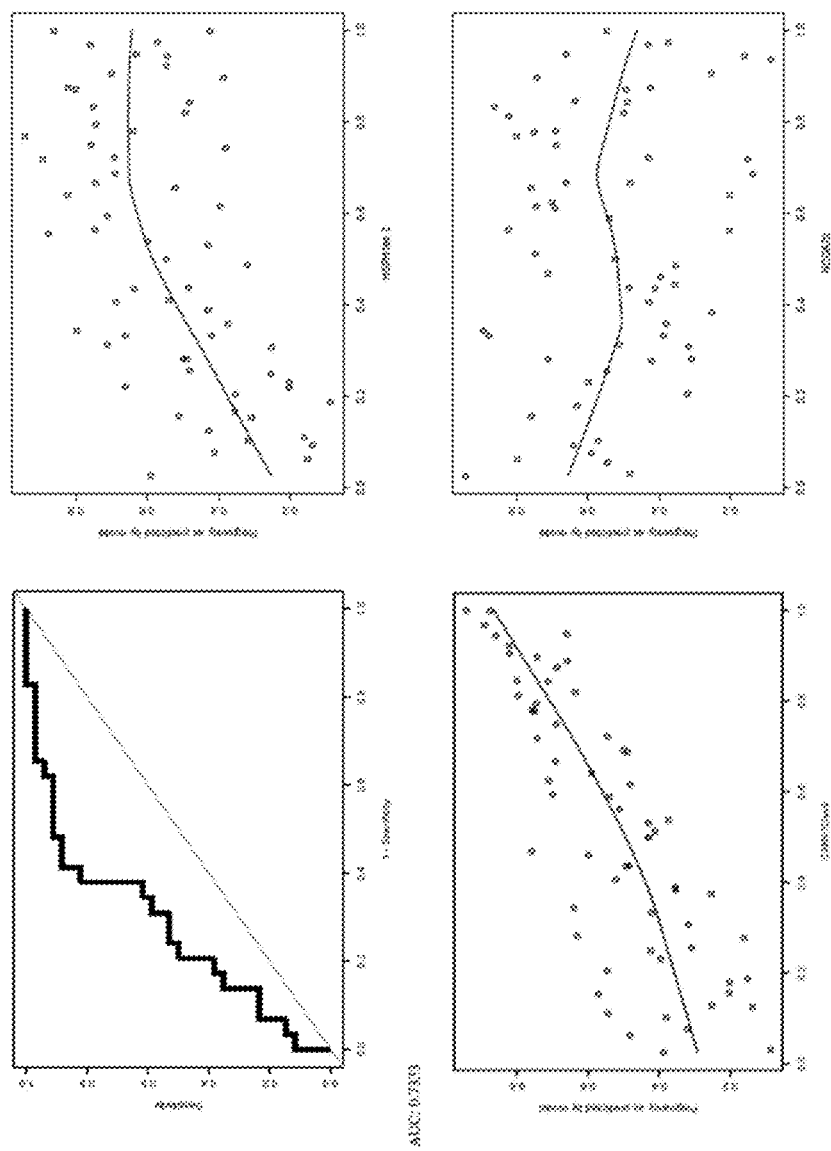

FIG. 6: One of the strongest models obtained with the inter-patient analysis after GnRH antagonist and rFSH pretreatment predictive for pregnancy, AUC=Area under the curve. Formula: Pregnant=−1.36999+1.79393*CAMK1D exon 9+0.89385*HSPH1exon 2−0.73763*NCOA7 (a positive value refers to a pregnancy a negative value to no pregnancy)

Figure 7:
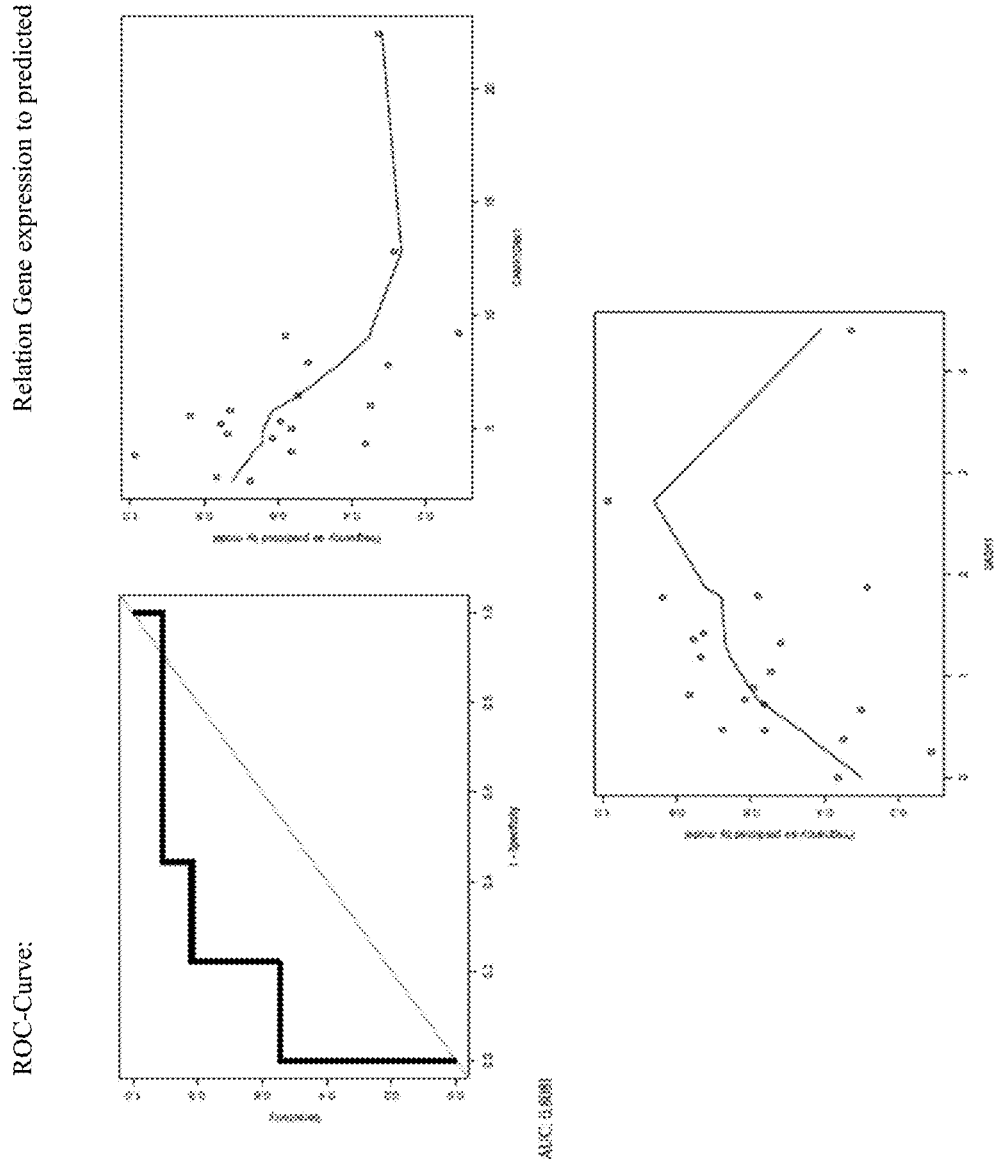

FIG. 7: One of the strongest models obtained with the inter-patient analysis after GnRH antagonist and HP-hMG pretreatment predictive for pregnancy, AUC=Area under the curve. Formula: Pregnant=0.46786+0.90886*SASH1−0.2264*CAMK1D exon 1 (a positive value refers to a pregnancy a negative value to no pregnancy)

Figure 8:
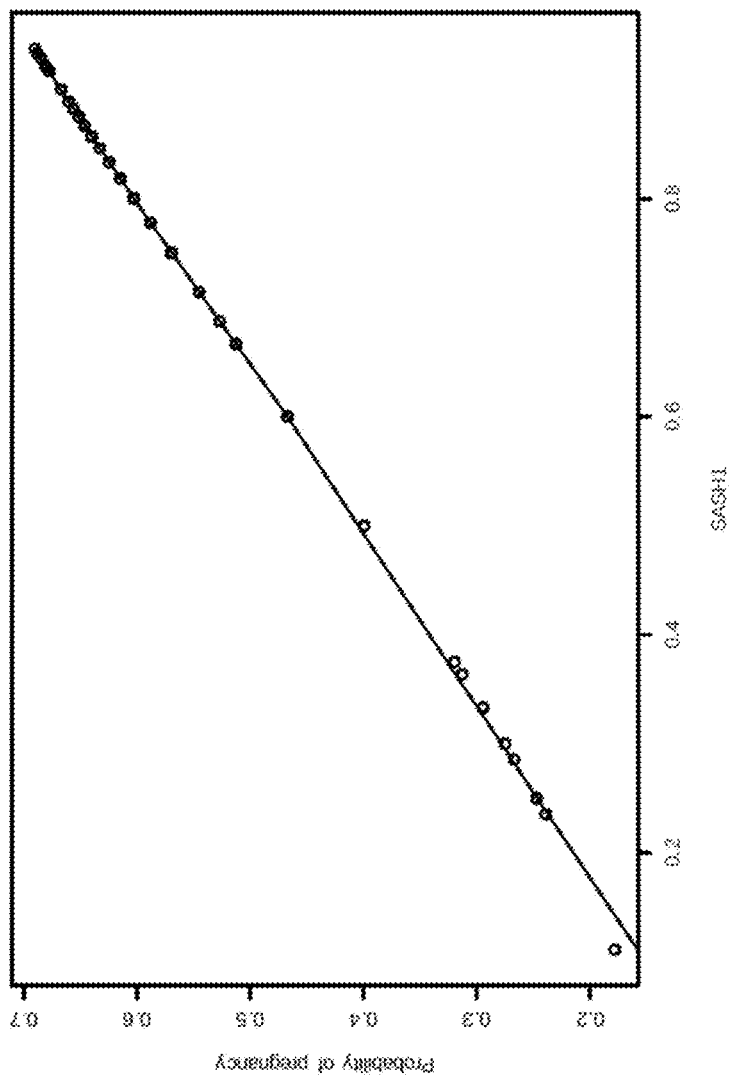

FIG. 8: Statistical analysis of probability of pregnancy for a predictive model comprising SASH1 alone.

Figure 9A:
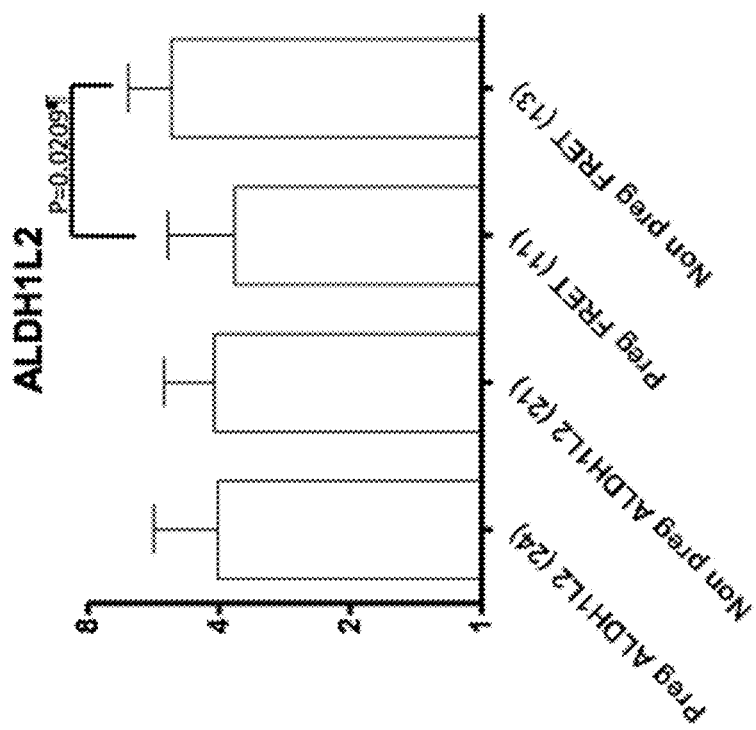

FIG. 9A: Comparing CC gene expression levels in CC of oocytes/embryos resulting in a pregnancy or not. Graphs depict log 2 transformed mRNA expression values of 3 preselected genes (FIG. 9A: ALDH1L2, FIG. 9B: ASNA; FIG. 9C: GOT1). Columns and error bars respectively represent the mean expression value and the standard deviation. T-test analysis found no statistical difference (p>0.05) when comparing the 2 fresh transfer groups. In patients having the embryo transfer in a consecutive menstrual cycle CC gene expression of the selected genes was significantly different between the CC of oocytes resulting in a pregnancy or not. The number of samples in each group is indicated between brackets.

Figure 9B:
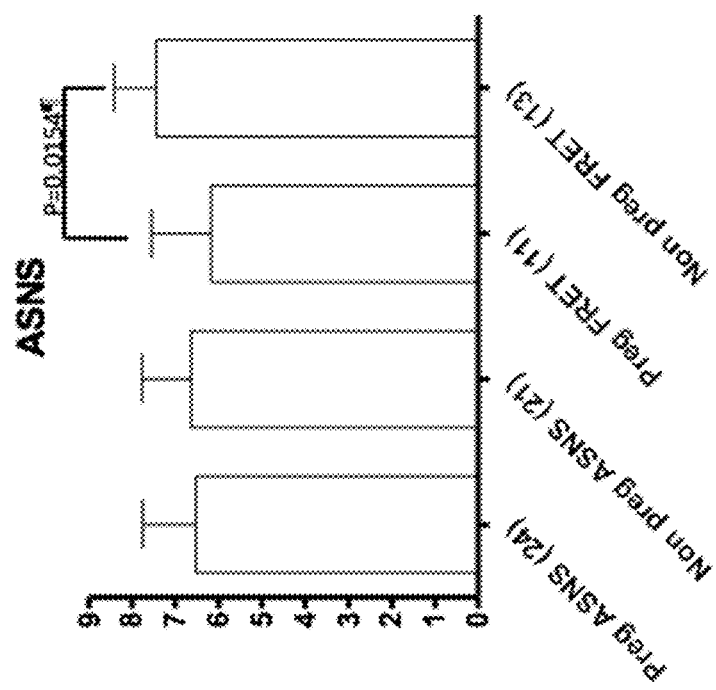
Figure 9C:
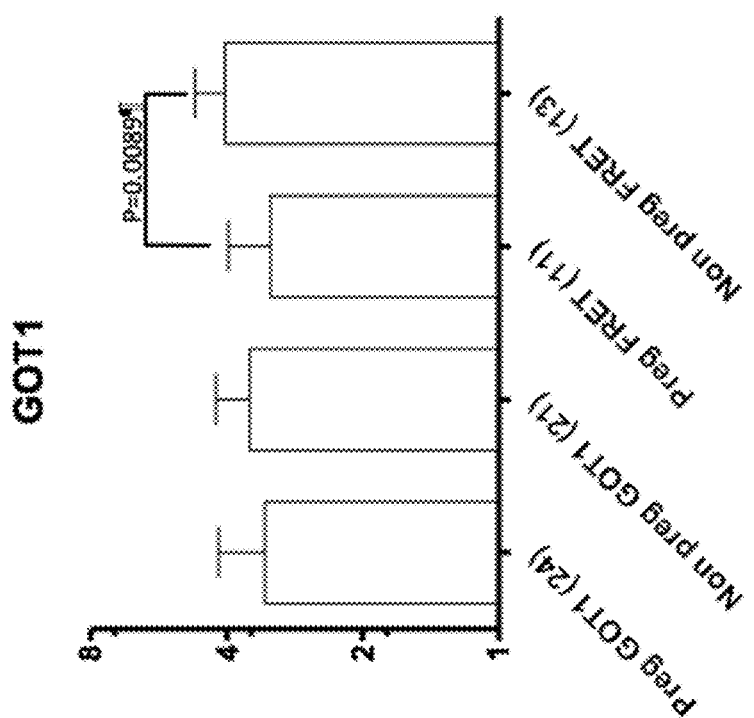

FIG. 9B: Comparing CC gene expression levels in CC of oocytes/embryos resulting in a pregnancy or not. Graphs depict log 2 transformed mRNA expression values of 3 preselected genes (FIG. 9A: ALDH1L2, FIG. 9B: ASNA; FIG. 9C: GOT1). Columns and error bars respectively represent the mean expression value and the standard deviation. T-test analysis found no statistical difference (p>0.05) when comparing the 2 fresh transfer groups. In patients having the embryo transfer in a consecutive menstrual cycle CC gene expression of the selected genes was significantly different between the CC of oocytes resulting in a pregnancy or not. The number of samples in each group is indicated between brackets.

FIG. 9C: Comparing CC gene expression levels in CC of oocytes/embryos resulting in a pregnancy or not. Graphs depict log 2 transformed mRNA expression values of 3 preselected genes (FIG. 9A: ALDH1L2, FIG. 9B: ASNA; FIG. 9C: GOT1). Columns and error bars respectively represent the mean expression value and the standard deviation. T-test analysis found no statistical difference (p>0.05) when comparing the 2 fresh transfer groups. In patients having the embryo transfer in a consecutive menstrual cycle CC gene expression of the selected genes was significantly different between the CC of oocytes resulting in a pregnancy or not. The number of samples in each group is indicated between brackets.

SUMMARY OF THE INVENTION

The present invention is directed to a method for detecting a biomarker gene or its splice variant for evaluating the competence of a mammalian oocyte to lead to childbirth, to implantation, to form a pre-implantation blastocyst or embryo, and/or to lead to fertilization; said method comprising using live birth or embryo development as a selection endpoint for the oocytes to be used;

making exon level analysis of gene expression in a micro array experiment of a sample comprising at least one granulosa or cumulus cell associated with the oocyte;

making intra-patient based comparison of said exon level analysis of gene expression; and consider only p-values <0.05 in a paired t-test as significant for a biomarker gene in being capable for evaluating the competence of a mammalian oocyte to lead to childbirth, to implantation, to form a pre-implantation blastocyst or embryo, and/or to lead to fertilization.

In an alternative embodiment a gene is considered a biomarker gene in evaluating the competence of an oocyte in case of differential expression of said exon level gene analysis, wherein said differential expression is at least 20% different from the exon level expression of said gene in control or reference standard.

Compared to existing methods the method of the present invention differs in the selection endpoint for the oocytes, in the exon level analysis of the genes, and the intra-patient based comparison. Using live birth and embryo development as the selection endpoint for the oocytes to be used in the identification of biomarker genes does indeed differentiate the results of the present finding over the art in which other endpoints, also referred to as 'intermediate endpoints', like fertilisation, morphology based embryo quality, or blastocyst development have been used. The relevance of the intermediate endpoints for full oocyte competence is limited as for example oocytes with a good (morphology based) embryo development capacity on day 3 will only result in a pregnancy in 33% of the cases. Choice of the proper endpoint has accordingly been key to come to the present set of biomarkers genes shown to give Positive Predictive Values (PPV's) and Negative Predictive Values (NPV's) of at least 60%.

A further differentiating feature is based on the fact that the gene selection was based on an intra-patient comparison. Doing for example a retrospective cumulus cell analysis of patients that became pregnant or not, the data will be biased by the inter-patient variance influencing the expression of the genes. Cumulus cell gene expression levels are influenced by: patient specific characteristics (e.g.: age, BMI, pretreatment), oocyte quality, and by expression of other genes (Adriaenssens et al. 2010). The competence of an oocyte is also determined by the ability to succeed in different processes. By using intra-patient samples instead, said inter-patient variability is suppressed, adding to the identification of the biomarker genes of the present invention shown to be applicable genes that can be used for live birth prediction for patients with different pretreatments.

Finally, the oocyte gene expression analysis is performed as an exon level analysis. As demonstrated in the examples hereinafter, this added to the resolving power of the predictive models. Where the overall expression for some of the genes was shown not to be predictive, looking at the expression level of exons within these genes showed to have a predictive value. When looking at the overall expression of a gene some of the signals associated at exon level will be leveled out with possible loss of interesting markers.

Using the foregoing method a minimal list of predictive biomarker genes has been obtained, and is presented in Table 13 herein below. Accordingly, in a further aspect the present invention provides the foregoing method wherein the exon level analysis of gene expression is performed on the genes of Table 13. This list of genes is to be seen as a reservoir of oocyte competence marker genes that can be used in multiparametric analyses to select the combinations of independent genes with the strongest prediction capacity for live birth. As demonstrated in the examples herein below, the present inventors successfully applied combinations of these genes in predictive models of oocyte competence after different types of Assisted Reproduction Technology (ART) treatment.

Thus in another embodiment the present invention provides a method to detect a biomarker gene combination model of genes or splice variants using cumulus cell gene expression from oocytes in a screening experiment comprising:

a. Detecting at least 2 biomarker genes identified using the foregoing method;

b. Using a two-tailed t-test to assess the correlation of the biomarker gene expression combinations of said at least 2 biomarker genes with the oocytes capacity for live birth, and retaining combinations of said at least 2 biomarker genes with a cut off value of Type I p<0.05 as a model to predict the competence of a mammalian oocyte in being capable of live birth or for evaluating embryo or blastocyte in vitro-development;

c. Making a stepwise multiparametric regression analysis to establish whether splice variants of said at least 2 biomarkers have a type III p value <0.3 and adding said splice variant to the model retained in step b; and d. Determining the overall p value of the model comprising the splice variants of step c, and retaining said splice variants in said model when the overall p value is further reduced.

As evident from the examples hereinafter, in one embodiment the foregoing screening experiment is a micro array experiment or a QPCR experiment.

In an alternative approach one departs from combinations of at least 2 biomarker genes of the genes as presented in Table 13 instead. In a particular embodiment the genes used to establish a biomarker gene expression model are selected from the 11 genes listed in Table 8 below. Using the thus identified biomarker genes and combination of biomarkers genes, the present invention further provides the use of said genes and gene combinations in an in vitro method of evaluating the competence of a mammalian oocyte to lead to childbirth, to implantation, to form a pre-implantation blastocyst or embryo, and/or to lead to fertilization.

Thus, in a further embodiment the present invention provides an in vitro method for evaluating the competence of a mammalian oocyte to lead to childbirth, to implantation, to form a pre-implantation blastocyst or embryo, and/or to lead to fertilization; said method comprising the steps of:

determining the level of a biomarker gene expression identified using the above mentioned method; or the level of biomarker gene expression of a combination of biomarkers identified using the foregoing method to detect a biomarker gene combination model of genes or splice variants, in a sample comprising at least one granulosa or cumulus cell associated with the oocyte; and evaluating the competence of the oocyte to lead to childbirth, to implantation, to form a pre-implantation blastocyst or embryo, and/or to lead to fertilization; based on said expression level(s).

In the foregoing method, evaluating the competence of the oocyte is done using a biomarker gene combination model determined using the method of the present invention. In particular using one of the biomarker gene combination models as described herein. In said models the expression levels of the genes will be used in a mathematical formula (infra) providing the probability of pregnancy (P) of said oocyte. In one embodiment, the expression levels used in evaluating the competence of the oocyte are normalized expression levels. Thus in one embodiment the in vitro methods for evaluating the competence of a mammalian oocyte as provided herein, further comprise the step of normalizing the expression levels. In another embodiment it comprises the step of normalizing the expression levels, wherein expression levels of the biomarker genes are normalized by correcting the absolute expression level of a said marker by comparing its expression to the expression of a gene that is not a marker, e.g., a housekeeping gene that is constitutively expressed. In one embodiment the housekeeping gene used in normalizing the biomarker gene expression levels is selected from the group consisting UBC, B2M, actin, GAPDH. HPRT, CPB, G6PD, histone H2A, and mitochondrial ribosomal protein S 18C gene (also known as RNA18S5); in particular UBC or 132M.

In an alternative method the competence of a mammalian oocyte is evaluated by comparing the level of marker gene expression with a control of which the competence is known. Differential expression of said gene is indicative for the competence of the oocyte when there is at least 20% difference in expression level. Thus in one embodiment the competence of a mammalian oocyte is evaluated using one of the biomarker gene combination models as described herein. In said embodiment the in vitro methods may further comprise the step of normalizing the exon level gene expression of said genes; and evaluating the competence of the oocyte to lead to childbirth, to implantation, to form a pre-implantation blastocyst or embryo, and/or to lead to fertilization; based on said normalized expression levels. In another embodiment the oocyte is evaluated by comparing the level of marker gene expression with a control of which the competence is known, optionally using normalized expression levels, and wherein said oocyte is capable to lead to childbirth, to implantation, to form a pre-implantation blastocyst or embryo, and/or to lead to fertilization, when there is at least 20% difference in expression level for said gene.

The skilled artisan is well aware of the methodologies available to determine the level of marker gene expression of said one or more biomarker genes. In one embodiment it comprises measuring polynucleotide levels of said genes by means of biological assays using primers and/or probes capable of specifically hybridizing to said polynucleotides or to one or more regions within said polynucleotides. In another embodiment it comprises measuring protein levels of related gene products by means of biological assays using binders, antibodies or fragments thereof, for said proteins, their pro-forms, their substrates, or their metabolisation products.

Although the foregoing methods are configured to determine the competence of a mammalian oocyte and in particular a human oocyte, this thus not imply the sample to be limited thereto. Samples to be used in the present invention evidently include granulosa or cumulus originating from an oocytes, but may as well be based on follicular fluid, or from culture medium, comprising at least one granulosa or cumulus cell associated with an oocyte. In the control or reference sample the competence of the oocyte is known, either samples with known competent or known non-competent oocytes can be used, wherein said samples could be obtained from the same or a different subject than the sample to be tested. In a particular embodiment the control or reference sample comprises at least one granulosa or cumulus cell associated with a known non-competent oocyte, either or not obtained from the same subject as the sample to be tested.

As follows from the examples hereinafter, it has been found by that the exon level analysis of the following genes, i.e. CAMK1D, PTGS2, EFNB2, VCAN, STC1, STC2, PGR and GPX3 allows to establish biomarker gene expression models to predict the competence of an oocyte in a sample. In particular the biomarker genes to be used in the in vitro methods according to the invention, are selected from the group comprising SASH1, MROH9, NCOA7, DNAH3, HSPH1 exon 2, HSPH1exon 6, GALNTL6, SPTBN5, CAMK1D exon 1, CAMK1D exon 9, and EFNB2. The present invention thus provides an in vitro method for evaluating the competence of a mammalian oocyte to lead to childbirth, to implantation, to form a pre-implantation blastocyst or embryo, and/or to lead to fertilization; said method comprising the steps of:
  determining exon level gene expression of one or more biomarker genes selected from the group consisting of CAMK1D, PTGS2, EFNB2, VCAN, STC1, STC2, PGR and GPX3 in a sample comprising at least one granulosa or cumulus cell associated with the oocyte;
  comparing the level of biomarker gene expression with a control of which the competence is known; and
  evaluating the competence of the oocyte to lead to childbirth, to implantation, to form a pre-implantation blastocyst or embryo, and/or to lead to fertilization; based on said comparison.

In a particular embodiment, the exon level analysis of gene expression is performed on the splice variant of one or more genes selected from SASH1, MROH9, NCOA7, DNAH3, HSPH1 exon 2, HSPH1exon 6, GALNTL6, SPTBN5, CAMK1D exon 1, CAMK1D exon 9, and EFNB2. Preferred combinations of biomarkers within the foregoing set of genes are selected from the list comprising;
  EFNB2 and NCOA7;
  CAMK1D exon 9 and HSPH1 exon2 and NCOA7
  CAMK1D exon 9 and HSPH1 exon6 and NCOA7
  CAMK1D exon 1 and SASH1; and
  EFBN2 and SASH1; eventually in combination with one or more additional genes selected from the genes enlisted in Table 13; in particular with one ore more additional more genes selected from the genes enlisted in Table 8; in particular with one or more additional genes selected from the group consisting of CAMK1D, PTGS2, EFNB2, VCAN, STC1, STC2, PGR and GPX3; more particular with a gene selected from EFNB2, CAMK1D exon 1, CAMK1D exon 9, HSPH1 exon 2, HSPH1 exon 6, NCOA7 and SASH1; even more in particular with a gene selected from of HSPH1 exon 2, HSPH1 exon 6, NCOA7 and SASH1

Thus in a further embodiment the present invention provides an in vitro method for evaluating the competence of a mammalian oocyte to lead to childbirth, to implantation, to form a pre-implantation blastocyst or embryo, and/or to lead to fertilization; said method comprising the steps of:
  determining exon level gene expression of 2, 3, 4, 5, 6, 7, or 8 biomarker genes selected from the group consisting of CAMK1D, PTGS2, EFNB2, VCAN, STC1, STC2, PGR and GPX3 in a sample comprising at least one granulosa or cumulus cell associated with the oocyte;

normalizing the exon level gene expression of said genes; and evaluating the competence of the oocyte to lead to childbirth, to implantation, to form a pre-implantation blastocyst or embryo, and/or to lead to fertilization; based on said normalized expression levels.

In another embodiment the present invention provides an in vitro method for evaluating the competence of a mammalian oocyte to lead to childbirth, to implantation, to form a pre-implantation blastocyst or embryo, and/or to lead to fertilization; said method comprising the steps of:

determining exon level gene expression of either CAMK1D exon 1, CAMK1D exon 9 or EFNB2, in combination with one or more genes selected from the genes enlisted in Table 13; in particular with one ore more additional genes selected from the genes enlisted in Table 8; in particular with one or more additional genes selected from the group consisting of HSPH1 exon 2, HSPH1 exon 6, NCOA7 and SASH1 in a sample comprising at least one granulosa or cumulus cell associated with the oocyte;

normalizing the exon level gene expression of said genes; and evaluating the competence of the oocyte to lead to childbirth, to implantation, to form a pre-implantation blastocyst or embryo, and/or to lead to fertilization; based on said normalized expression levels.

In a further aspect the present invention provides the use of the in vitro methods according to invention for identifying oocytes that are capable of giving rise to a viable pregnancy after fertilization, optionally in combination with another in vitro oocyte, sperm or embryo evaluation method.

In a further aspect the present invention provides an oocyte bank comprising mammalian oocytes scored according to an in vitro method according the invention, as well as a method of preparing an embryo comprising the use of an oocyte scored according to an in vitro method according the invention.

Further numbered embodiments of the present invention include;

1. An in vitro method of selecting oocytes having the highest chance of viable pregnancy after fertilization, said method comprising the steps of:

(a) collecting oocytes with their cumulus and/or granulosa cells from a female having undergone an ovarian stimulation treatment;

(b) measuring in the cumulus or granulosa cells from the oocytes, exon levels of gene expression from one or more genes as represented in table 13;

(c) making intra-patient based comparison of said exon level analysis of said gene expression in the oocytes;

(d) ranking said oocytes based on the level of expression for at least one of said genes;

(e) based on said ranking, determining said oocytes competence to lead to childbirth, to implantation, to form a pre-implantation blastocyst or embryo, and/or to lead to fertilization;

(f) selecting said oocyte having the highest competence, as being the one having the highest chance of viable pregnancy after fertilization.

2. The in vitro method of embodiment 1; wherein said ovarian stimulation treatment is selected from the list comprising Luteinizing hormone and analogs, Chorionic Gonadotrophins and analogs, FSH and agonists, GnRH and GnRH analogs (agonists and antagonists) associated with recombinant FSH and/or hMG, Epidermal growth factor (EGF) and analogs, EGF-like proteins (peptides), amphiregulin, epiregulin, betacellulin and analogs, Interleukin-6, Interleukin-1, Leukemia Inhibitory Factor (LIF), Phosphodiesterase type 4 Inhibitors, Low Molecular weight compounds activating any of the foregoing, clomiphene citrate, tamoxifen, letrozole; and any combinations of the foregoing.

3. The in vitro method according to embodiment 1, wherein the exon level analysis of gene expression is performed on the splice variant of a gene selected from the list comprising: SASH1, CAMK1D, EFNB2, and HSPH1.

4. The in vitro method according to embodiment 1, wherein the exon level analysis of gene expression is performed on the splice variant of SASH1.

5. The in vitro method according to embodiment 1, further comprising the step of normalizing the exon level gene expression of said one or more genes.

6. An in vitro method according to embodiment 1, wherein determining the exon level analysis of gene expression of said one or more genes comprises measuring polynucleotide levels of said genes by means of biological assays using primers and/or probes capable of specifically hybridizing to said polynucleotides or to one or more regions within said polynucleotides.

7. An in vitro method according to embodiment 1, wherein determining the exon level analysis of gene expression of said one or more genes comprises measuring protein levels of related gene products by means of biological assays using binders, antibodies or fragments thereof, for said proteins, their pro-forms or their metabolisation products.

8. A method of implanting an embryo in a female, said method comprising the steps of:

(a) collecting oocytes with their cumulus and/or granulosa cells from a female having undergone an ovarian stimulation treatment;

(b) measuring in the cumulus or granulosa cells from the oocytes, exon levels of gene expression from one or more genes as represented in table 13;

(c) making intra-patient based comparison of said exon level analysis of said gene expression in the oocytes;

(d) ranking said oocytes based on the level of expression for at least one of said genes;

(e) based on said ranking, determining said oocytes competence to lead to childbirth, to implantation, to form a pre-implantation blastocyst or embryo, and/or to lead to fertilization;

(f) selecting said oocyte having the highest competence, as being the one having the highest chance of viable pregnancy after fertilization.

(g) fertilizing the oocyte having the highest competence as determined in (f); and (h) implanting the embryo in a female.

9. The in vitro method of embodiment 8; wherein said ovarian stimulation treatment is selected from the list comprising Luteinizing hormone and analogs, Chorionic Gonadotrophins and analogs, FSH and agonists, GnRH and GnRH analogs (agonists and antagonists) associated with recombinant FSH and/or hMG, Epidermal growth factor (EGF) and analogs, EGF-like proteins (peptides), amphiregulin, epiregulin, betacellulin and analogs, Interleukin-6, Interleukin-1, Leukemia Inhibitory Factor (LIP), Phosphodiesterase type 4 Inhibitors, Low Molecular weight compounds activating any of the foregoing, clomiphene citrate, tamoxifen, letrozole; and any combinations of the foregoing.

10. The in vitro method according to embodiment 8, wherein the exon level analysis of gene expression is performed on the splice variant of a gene selected from the list comprising: SASH1, CAMK1D, EFNB2, and HSPH1.

11. The in vitro method according to embodiment 8, wherein the exon level analysis of gene expression is performed on the splice variant of SASH1.

12. The in vitro method according to embodiment 8, further comprising the step of normalizing the exon level gene expression of said one or more genes.

13. An in vitro method according to embodiment 8, wherein determining the exon level analysis of gene expression of said one or more genes comprises measuring polynucleotide levels of said genes by means of biological assays using primers and/or probes capable of specifically hybridizing to said polynucleotides or to one or more regions within said polynucleotides.

14. An in vitro method according to embodiment 8, wherein determining the exon level analysis of gene expression of said one or more genes comprises measuring protein levels of related gene products by means of biological assays using binders, antibodies or fragments thereof, for said proteins, their pro-forms or their metabolisation products.

DETAILED DESCRIPTION OF THE INVENTION

In the context of the present invention the term 'oocyte competence' or 'competence' is meant to be the ability of an oocyte to resume meiosis, cleave after fertilization, help promote embryonic development and pregnancy establishment, and bring a pregnancy to term in good health. In other words, it represents the ability of a mammalian oocyte to lead to childbirth, to implantation, to form a pre-implantation blastocyst or embryo, and/or to lead to fertilization.

In the context of the present invention, the term "embryo" is meant to be a fertilized oocyte.

According to the invention, the oocyte may result from a natural cycle, a modified natural cycle or a stimulated cycle for ART (Assisted reproduction techniques) comprising e.g. In Vitro Fertilization (IVF) or intracytoplasmic sperm injection (ICSI). The oocytes used in the methods of the present invention are typically obtained between 20 to 44 hours after ovulation induction, wherein the ovulation induction could be obtained in a natural or modified natural cycle. The term "natural cycle" refers to the natural cycle by which the female or woman produces an oocyte. The term "modified natural cycle", also referred to as a "stimulated cycle" refers to the process by which, multiple follicle growth and/or ovulation of the oocytes is induced by treatment of the female or woman. Ovulation triggers that can be used in such stimulated cycle include for example Luteinizing hormone or analogs. Chorionic Gonadotrophins and analogs, FSH and agonists. GnRH and analogs. Epidermal growth factor (EGF) and analogs, EGF-like proteins (peptides) amphiregulin, epiregulin, betacellulin and their analogs, Interleukin-6, Interleukin-1, Leukemia Inhibitory Factor (LIF) Phosphodiesterase type 4 Inhibitors, Low Molecular weight compounds activating any of the foregoing, and Any combinations of the foregoing. Particular treatments include ovarian stimulation with GnRH analogs (agonist or antagonists) associated with recombinant FSH and/or hMG; or with clomiphene citrate, tamoxifen, letrozole and the like.

In one embodiment the oocytes used in the methods of the present invention are obtained and/or collected between 20 to 40 hours after the ovulatory trigger. In another embodiment the oocytes used in the methods of the present invention are obtained and/or collected between 34 to 38 hours after ovulation induction; in particular 36 hours after ovulation induction. As will be evident to the skilled artisan the ovulatory trigger to the oocytes can be performed in vitro or in vivo.

A 'granulosa cell' also referred to as a 'follicular cell', is a somatic cell of the sex cord that is closely associated with the developing female gamete (oocyte) in the ovary of mammals.

A 'cumulus cell' is a cell as present in the discus proligerus (cluster of cells) that surrounds the oocyte both in the ovarian follicle and after ovulation.

Within the methods of the present invention, reference to 'an oocyte' is meant to include granulosa cells and/or cumulus cells associated with an oocyte matured and/or ovulation induced oocyte. Thus in one embodiment the present invention the oocytes used refer to cumulus cells, wherein said cumulus cells can be analyzed using the methods of the present invention prior or after the ovulatory trigger.

By the phrase "determining the level of marker expression" is meant an assessment of the degree of expression of a marker in a sample at the nucleic acid or protein level, using technology available to the skilled artisan to detect a sufficient portion of any marker expression product (including nucleic acids and proteins). The 'marker gene expression level' may for example be determined using nucleic acid microarray. Northern blot, reverse transcription PCR, Western blot, enzyme-linked immunosorbent assay, protein microarray or FACS analysis. The term 'marker gene expression' is meant to include expression of the full-length gene or variants thereof, in particular splice variants containing specific exons. Particularly interesting splice variants in the context of the present invention are any of the following splice variants or combinations thereof comprising:

Exon 2 and/or exon 6 of HSPH1,
Exon 1 and/or exon 9 of CAMK1D,
Exon 1 and/or exon 2 of NCOA7,
Exon 12 of SASH1,
Exon 14 of MROH9,
Exon 8 of SPTBN5,
Exon 16 of GALNTL6, and/or
Exon 21 of DNAH3

In a particular embodiment the combination of splice-variants used in the methods of the present invention is selected from the list comprising: exon 2 of HSPH1 and exon 6 of HSPH1, exon 2 of HSPH1 and exon 1 or exon 9 of CAMK1D, exon 2 of HSPH1 and exon 1 or exon 2 of NCOA7; exon 2 of HSPH1 and exon 12 of SASH1, exon 2 of HSPH1 and exon 14 or MROH9, exon 2 of HSPH1 and exon 8 of SPTBN5, exon 2 of HSPH1 and GALNTL6, exon 2 of HSPH1 and exon 21 of DNAH3, exon 6 of HSPH1 and exon 1 or exon 9 of CAMK1D, exon 6 of HSPH1 and exon 1 or exon 2 of NCOA7; exon 6 of HSPH1 and exon 12 of SASH1, exon 6 of HSPH1 and exon 14 or MROH9, exon 6 of HSPH1 and exon 8 of SPTBN5, exon 6 of HSPH1 and GALNTL6, exon 6 of HSPH1 and exon 21 of DNAH3, exon 2 and exon 6 of HSPH1 and exon 1 of CAMK1D, exon 2 and exon 6 of HSPH1 and exon 9 of CAMK1D, exon 2 and exon 6 of HSPH1 and exon 1 of NCOA7, exon 2 and exon 6 of HSPH1 and exon 2 of NCOA7; exon 2 and exon 6 of HSPH1 and exon 12 of SASH1, exon 2 and exon 6 of HSPH1 and exon 14 or MROH9, exon 2 and exon 6 of HSPH1 and exon 8 of SPTBN5, exon 2 and exon 6 of HSPH1 and GALNTL6, exon 2 and exon 6 of HSPH1 and exon 21 of DNAH3, exon 2 and exon 6 of HSPH1 and exon 1 and exon 9 of CAMK1D, exon 2 and exon 6 of HSPH1 and exon 1 and exon 9 of CAMK1D and exon 1 and exon 2 of NCOA7, exon 2 and exon 6 of HSPH1 and exon 1 and exon 9 of CAMK1D and exon 1 and exon 2 of NCOA7 and exon 12 of SASH1, exon 2 and exon 6 of HSPH1 and exon 1 and exon 9 of CAMK1D and exon 1 and exon 2 of NCOA7 and exon 12 of SASH1 and exon 14 of MROH9, exon 2 and exon 6 of HSPH1 and exon 1 and exon 9 of CAMK1D and exon 1 and exon 2 of NCOA7 and exon 12 of SASH1 and exon 14 of MROH9 and exon 8 of SPTBN5, exon 2 and exon 6 of HSPH1 and exon 1 and exon 9 of CAMK1D and exon 1 and exon 2 of NCOA7 and exon 12 of SASH1 and exon 14 of MROH9 and exon 8 of SPTBN5 and exon 16 of GALNTL6, exon 2 and exon 6 of HSPH1 and exon 1 and exon 9 of CAMK1D and exon 1 and exon 2 of NCOA7 and exon 12 of SASH1 and exon 14 of MROH9 and exon 8 of SPTBN5 and exon 16 of GALNTL6 and exon 21 of DNAH3.

In a further particular embodiment the combination of splice-variants used in the methods of the present invention is selected from the list comprising: exon 1 of CAMK1D and exon 9 of CAMK1D, exon 1 of CAMK1D and exon 2 or exon 6 of HSPH1, exon 1 of CAMK1D and exon 1 or exon 2 of NCOA7, exon 1 of CAMK1D and exon 12 of SASH1, exon 1 of CAMK1D and exon 14 of MROH9, exon 1 of CAMK1D and exon 8 of SPTBN5, exon 1 of CAMK1D and exon 16 of GALNTL6, exon 1 of CAMK1D and exon 21 of DNAH3, exon 9 of CAMK1D and exon 2 or exon 6 of HSPH1, exon 9 of CAMK1D and exon 1 or exon 2 of NCOA7, exon 9 of CAMK1D and exon 12 of SASH1, exon 9 of CAMK1D and exon 14 of MROH9, exon 9 of CAMK1D and exon 8 of SPTBN5, exon 9 of CAMK1D and GALNTL6, exon 9 of CAMK1D and exon 21 of DNAH3, exon 1 and 9 of CAMK1D and exon 2 of HSPH1, exon 1 and 9 of CAMK1D and exon 6 of HSPH1, exon 1 and 9 of CAMK1D and exon 1 of NCOA7, exon 1 and 9 of CAMK1D and exon 2 of NCOA7, exon 1 and 9 of CAMK1D and exon 12 of SASH1, exon 1 and 9 of CAMK1D and exon 14 of MROH9, exon 1 and 9 of CAMK1D and exon 8 of SPTBN5, exon 1 and 9 of CAMK1D and exon 16 of GALNTL6, exon 1 and 9 of CAMK1D and exon 21 of DNAH3, exon 1 and 9 of CAMK1D and exon 2 and exon 6 of HSPH1, exon 1 and 9 of CAMK1D and exon 2 and exon 6 of HSPH1 and exon 1 of NCOA7, exon 1 and 9 of CAMK1D and exon 2 and exon 6 of HSPH1 and exon 1 and exon 2 of NCOA7, exon 1 and 9 of CAMK1D and exon 2 and exon 6 of HSPH1 and exon 1 and exon 2 of NCOA7 and exon 12 of SASH1, exon 1 and 9 of CAMK1D and exon 2 and exon 6 of HSPH1 and exon 1 and exon 2 of NCOA7 and exon 12 of SASH1 and exon 14 of MROH9, exon 1 and 9 of CAMK1D and exon 2 and exon 6 of HSPH1 and exon 1 and exon 2 of NCOA7 and exon 12 of SASH1 and exon 14 of MROH9 and SPTBN5, exon 1 and 9 of CAMK1D and exon 2 and exon 6 of HSPH1 and exon 1 and exon 2 of NCOA7 and exon 12 of SASH1 and exon 14 of MROH9 and SPTBN5 and exon 16 of GALNTL6, exon 1 and 9 of CAMK1D and exon 2 and exon 6 of HSPH1 and exon 1 and exon 2 of NCOA7 and exon 12 of SASH1 and exon 14 of MROH9 and SPTBN5 and exon 16 of GALNTL6 and exon 21 of DNAH3, exon 1 of CAMK1D and SASH1, exon 9 of CAMK1D and exon 2 of HSPH1 and NCOA7, exon 9 of CAMK1D and exon 2 of HSPH1 and exon 1 or exon 2 of NCOA7, exon 1 of CAMK1D and exon 12 of SASH1, exon 9 of CAMK1D and exon 6 of HSPH1 and exon 12 of SASH1, exon 9 of CAMK1D and exon 6 of HSPH1 and SASH1

In another embodiment the combination of splice-variants used in the methods of the present invention is selected from the list comprising: EFNB2 and exon 9 or exon 1 of CAMK1D, EFNB2 and exon 2 or exon 6 of HSPH1, EFNB2 and exon 1 or exon 2 of NCOA7. EFNB2 and exon 12 of SASH1. EFNB2 and exon 14 of MROH9, EFNB2 and exon 8 of SPTBN5, EFNB2 and exon 16 of GALNTL6, EFNB2 and exon 21 of DNAH3, EFNB2 and exon 9 or exon 1 of CAMK1D and exon 2 or exon 6 of HSPH1, EFNB2 and exon 9 or exon 1 of CAMK1D and exon 1 or exon 2 of NCOA7. EFNB2 and exon 9 or exon 1 of CAMK1D and exon 12 of SASH1, EFNB2 and exon 2 or exon 6 of HSPH1 and exon 1 or exon 2 of NCOA7. EFNB2 and exon 2 or exon 6 of HSPH1 and exon 12 of SASH1. EFNB2 and exon 1 or exon 2 of NCOA7 and exon 9 or exon 1 of CAMK1D, EFNB2 and exon 1 or exon 2 of NCOA7 and exon 2 or exon 6 of HSPH1. EFNB2 and exon 1 or exon 2 of NCOA7 and exon 12 of SASH1. EFNB2 and exon 12 of SASH1 and exon 1 or exon 2 of NCOA7 and exon 2 or exon 6 of HSPH1, EFNB2 and exon 9 or exon 1 of CAMK1D and exon 2 or exon 6 of HSPH1 and exon 1 or exon 2 of NCOA7, EFNB2 and NCOA7, EFNB2 and SASH1, EFNB2 and exon 1 or exon 2 of NCOA7, EFNB2 and exon 12 of SASH1.

In another embodiment the combinations of splice variants used in the methods of the present invention is selected from the list comprising exon 12 of SASH1 and HSPH1 or exon 2 or exon 6 of HSPH1; exon 12 of SASH1 and MROH9 or exon 14 of MROH9; exon 12 of SASH1 and SPTBN5 or exon 8 of SPTBN5; exon 12 of SASH and CAMK1D or exon 1 or exon 9 of CAMK1D; exon 12 of SASH1 and GALNTL6 or exon 16 of GALNTL6; exon 12 of SASH1 and NCOA7 or exon 1 or exon 2 of NCOA7; exon 12 of SASH1 and DNAH3 or exon 21 of DNAH3; exon 12 of SASH1 and EFNB2; exon 12 of SASH1 and HSPH1 or exon 2 or exon 6 of HSPH1 and SPTBN5 or exon 8 of SPTBN5; exon 12 of SASH1 and HSPH1 or exon 2 or exon 6 of HSPH1 and CAMK1D or exon 1 or exon 9 of CAMK1D; exon 12 of SASH1 and HSPH1 or exon 2 or exon 6 of HSPH1 and GALNTL6 or exon 16 of GALNTL6; exon 12 of SASH1 and HSPH1 or exon 2 or exon 6 of HSPH1 and NCOA7 or exon 1 or exon 2 of NCOA7; exon 12 of SASH1 and HSPH1 or exon 2 or exon 6 of HSPH1 and DNAH3 or exon 21 of DNAH3; exon 12 of SASH1 and HSPH1 or exon 2 or exon 6 of HSPH1 and EFNB2; exon 12 of SASH1 and HSPH1 or exon 2 or exon 6 of HSPH1 and MROH9 or exon 14 of MROH9; exon 12 of SASH1 and HSPH1 or exon 2 or exon 6 of HSPH1 and MROH9 or exon 14 of MROH9 and SPTBN5 or exon 8 of SPTBN5; exon 12 of SASH1 and HSPH1 or exon 2 or exon 6 of HSPH1 and MROH9 or exon 14 of MROH9 and CAMK1D or exon 1 or exon 9 of CAMK1D; exon 12 of SASH1 and HSPH1 or exon 2 or exon 6 of HSPH1 and MROH9 or exon 14 of MROH9 and GALNTL6 or exon 16 of GALNTL6; exon 12 of SASH1 and HSPH1 or exon 2 or exon 6 of HSPH1 and MROH9 or exon 14 of MROH9 and NCOA7 or exon 1 or exon 2 of NCOA7; exon 12 of SASH1 and HSPH1 or exon 2 or exon 6 of HSPH1 and MROH9 or exon 14 of MROH9 and DNAH3 or exon 21 of DNAH3; exon 12 of SASH1 and HSPH1 or exon 2 or exon 6 of HSPH1 and MROH9 or exon 14 of MROH9 and EFNB2; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D; exon 12 of SASH1 and HSPH1 or exon 2 or exon 6 of HSPH1 and MROH9 or exon 14 of MROH9 and SPTBN5 or exon 8 of SPTBN5 and GALNTL6 or exon 16 of GALNTL6; exon 12 of SASH1 and HSPH1 or exon 2 or exon 6 of HSPH1 and MROH9 or exon 14 of MROH9 and SPTBN5 or exon 8 of SPTBN5 and NCOA7 or exon 1 or exon 2 of NCOA7; exon 12 of SASH1 and HSPH1 or exon 2 or exon 6 of HSPH1 and MROH9 or exon 14 of MROH9 and SPTBN5 or exon 8 of SPTBN5 and DNAH3 or exon 21 of DNAH3; exon 12 of SASH1 and HSPH1 or exon 2 or exon 6 of HSPH1 and MROH9 or exon 14 of MROH9 and SPTBN5 or exon 8 of SPTBN5 and EFNB2; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and NCOA7 or exon 1 or exon 2 of NCOA7; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and DNAH3 or exon 21 of DNAH3; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and EFNB2; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and NCOA7 or exon 1 or exon 2 of NCOA7; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and DNAH3 or exon 21 of DNAH3; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and EFNB2; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and NCOA7 or exon 1 or exon 2 of NCOA7 and DNAH3 or exon 21 of DNAH3; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and NCOA7 or exon 1 or exon 2 of NCOA7 and EFNB2; exon 12 of SASH1 and HSPH1 or exon 2 or exon 6 of HSPH1 and MROH9 or exon 14 of MROH9 and SPTBN5 or exon 8 of SPTBN5 and CAMK1D or exon 1 or exon 9 of CAMK1D and GALNTL6 or exon 16 of GALNTL6 and NCOA7 or exon 1 or exon 2 of NCOA7 and DNAH3 or exon 21 of DNAH3 and EFNB2.

In another embodiment the models used in the in vitro models according to the invention is based on the determination of either EFNB2, or exon 1 or exon 9 of CAMK1D in combination with one or more marker genes selected from STC1, SASH, PGR, GSTA4. GSTA3, GPX, NCOA7, HSPH1, MROH9. DNAH3, GALNTL6 and SPTBN5; in particular with one or more genes selected from STC1, SASH1, PGR, GSTA4, GSTA3, GPX, NCOA7, and HSPH1. In a further embodiment the models used are based on the determination of either EFNB2, or exon 1 or exon 9 of CAMK1D in combination with one or more splice variants selected from exon 12 of SASH1, exon 1 of NCOA7, exon 2 of NCOA7, exon 2 of HSPH1, exon 6 of HSPH1, exon 14 of MROH9, exon 21 of DNAH3, exon 16 of GALNTL6 and exon 8 of SPTBN5; in particular with one or more splice variants selected from exon 12 of SASH1, exon 1 of NCOA7, exon 2 of NCOA7, exon 2 of HSPH1, and exon 6 of HSPH1.

The control is at least one granulosa or cumulus cell associated with an oocyte, of which the competence is known. In this respect a positive control is at least one granulosa or cumulus cell associated with an oocyte competent to lead to childbirth, to implantation, to form a pre-implantation blastocyst or embryo, and/or to lead to fertilization. In another embodiment, a positive control may be a chromosomally normal oocyte.

In certain embodiments the level of expression of at least 2 marker genes of Table 13 is determined. In a particular embodiment the level of biomarker gene expression is determined for one of the following combinations;

EFNB2, GSTA4 and PGR;
EFNB2, GSTA4. PGR, GPX3 and GSTA3;
EFNB2, and NCOA7:
EFNB2, and SASH1;
EFNB2, CAMK1D exon 1. CAMK1D exon 9, SASH1, MROH9. NCOA7, DNAH3, HSPH1 exon 2. HSPH1exon 6. GALNTL6, and SPTBN5;
EFNB2. CAMK1D exon 1. CAMK1D exon 9. HSPH1 exon 2, HSPH1 exon 6. NCOA7, and SASH1;
CAMK1D exon 9, HSPH1 exon 2 and NCOA7;
CAMK1D exon 9, HSPH1 exon 6 and NCOA7;
CAMK1D exon 1, and SASH1;

These new models proved to be able to rank oocyte for their potential for pregnancy, and live birth. As is evident from the foregoing models CAMK1D exon 1 or exon 9 and EFNB2 are confirmed as positive control genes in both intra- and inter-patient analysis, combining these markers with further genes selected from GSTA4, GSTA3, PGR, GPX3, NCOA7, SASH1, MROH9, DNAH3, HSPH1 exon 2, HSPH1exon 6, GALNTL6 and SPTBN5, results in models that are predictive in determining an oocyte competence to pregnancy and live-birth. As is evident form the examples hereinafter, using these combinations of genes the PPV, NPV and accuracy of the prediction exceeded 60%. In another embodiment the in vitro models of the present invention, see for example model 3 in Table 6 below, may further comprise patient and/or cycle parameters such as for example age, days of stimulation and relative estradiol (E2), Anti-Mullerian hormone levels (AMH), day 3 follicle stimulating hormone levels (Day 3 FSH) and the like; in a particular embodiment the patient and cycle parameters used in the in vitro models of the present invention are days of stimulation, relative E2 and age.

In one embodiment and departing from the foregoing set of genes, the present invention provides an in vitro model for predicting the competence of a mammalian oocyte to lead to pregnancy and live birth; said method comprising the steps of:

determining the level of marker gene expression of EFNB2. GSTA4 and PGR in a sample comprising at least one granulosa or cumulus cell associated with the oocyte comparing the level of marker gene expression with a control of which the competence is known; or normalizing the exon level gene expression of said genes and evaluating the competence of the oocyte to lead to pregnancy and live birth based on said comparison or on said normalized expression levels.

In one embodiment of the foregoing method the competence of the oocyte is based on determining the probability of pregnancy (P) given by the equation $P=-a+b*EFNB2+c*GSTA4-d*PGR$; wherein a is a number from and between 1.00 to 4.00; b is a number from and between 0.00 and 2.00; c is a number from and between 0.00 and 2.00; d is a number from between 0.00 and 2.00; EFNB2 is the normalized expression level of EFNB2; GSTA4 is the normalized expression level of GSTA4; and PGR is the normalized expression level of PGR. In a particular embodiment a is a number from and between 2.00 to 3.00; b is a number from and between 0.00 and 1.00; c is a number from and between 0.00 and 1.00; d is a number from between 0.00 and 1.00, in the foregoing equation. In an even further embodiment a is 2.26; b is 0.79; c is 0.095; and d is 0.096 in the foregoing equation.

In one embodiment of the foregoing model based on EFNB2, GSTA4 and PGR, the in vitro method further includes determining the level of marker gene expression of GPX3 and GSTA3 in a sample comprising at least one granulosa or cumulus cell associated with the oocyte, and using said further marker gene expression in evaluating the competence of the oocyte. In a further embodiment of the foregoing model based on EFNB2. GSTA4 and PGR, the competence of the oocyte is based on determining the probability of pregnancy (P) given by the equation $P=-a+b*EFNB2+c*GSTA4-d*PGR-e*GPX3-f*GSTA3$; wherein a is a number from and between 1.00 to 4.00; b is a number from and between 0.00 and 2.00; c is a number from and between 0.00 and 2.00; d is a number from between 0.00 and 2.00; e is a number from and between 0.00 and 2.00; f is a number from and between 0.00 and 2.00; EFNB2 is the normalized expression level of EFNB2; GSTA4 is the normalized expression level of GSTA4; PGR is the normalized expression level of PGR; GPX3 is the normalized expression of GPX3; and GSTA3 is the normalized expression level of GSTA3. In particular embodiment a is a number from and between 1.00 to 2.00: b is a number from and between 0.00 and 1.00; c is a number from and between 0.00 and 1.00; d is a number from between 0.00 and 1.00; e is a number from and between 0.00 and 1.00; and f is a number from between 0.00 and 1.00 in the foregoing equation. More in particular a is 1.02, b is 0.63, c is 0.27, d is 0.11, e is 0.43 and f is 0.51 in the foregoing equation.

In one embodiment of the foregoing models based on EFNB2, GSTA4 and PGR, the in vitro method further includes determining the patient and cycle characteristics age, days of stimulation and Rel E2 (Relative E2), and using said further patient and cycle characteristics in evaluating the competence of the oocyte. In a further embodiment of the foregoing model based on EFNB2, GSTA4 and PGR, the competence of the oocyte is based on determining the probability of pregnancy (P) given by the equation $P=-a+b*EFNB2+c*GSTA4-d*PGR-e*GPX3-f*GSTA3+g*days$ of $stimulation+h*Rel\ E2+i*age$; wherein a is a number from and between 5.00 to 15.00; b is a number from and between 0.00 and 2.00; c is a number from and between 0.00 and 2.00; d is a number from between 0.00 and 2.00; e is a number from and between 0.00 and 2.00; f is a number from and between 0.00 and 2.00; g is a number from and between 0.00 and 2.00; h is a number from and between 0.00 and 2.00; i is a number from and between 0.00 and 2.00; EFNB2 is the normalized expression level of EFNB2; GSTA4 is the normalized expression level of GSTA4; PGR is the normalized expression level of PGR; GPX3 is the normalized expression of GPX3; and GSTA3 is the normalized expression level of GSTA3. In particular embodiment a is a number from and between 9.00 to 13.00; b is a number from and between 1.00 and 2.00; c is a number from and between 0.00 and 1.00; d is a number from between 0.00 and 1.00; e is a number from and between 0.00 and 1.00; and f is a number from between 0.00 and 1.00; g is a number from and between 0.00 and 1.00; h is a number from and between 0.00 and 1.00; and i is a number from and between 0.00 and 1.00 in the foregoing equation. More in particular a is 11.27, b is 1.35, c is 0.46, d is 0.24, e is 0.66, f is 0.86, g is 0.0.50, h is 0.009 and i is 0.14 in the foregoing equation.

In one embodiment and departing from the foregoing set of genes, the present invention provides an in vitro model for predicting the competence of a mammalian oocyte to lead to pregnancy and live birth; said method comprising the steps of:

determining the level of marker gene expression of EFNB2 and NCOA7 in a sample comprising at least one granulosa or cumulus cell associated with the oocyte comparing the level of marker gene expression with a control of which the competence is known; or normalizing the exon level gene expression of said genes and evaluating the competence of the oocyte to lead to pregnancy and live birth based on said comparison or on said normalized expression levels.

In one embodiment of the foregoing method the competence of the oocyte is based on determining the probability of pregnancy (P) given by the equation $P=a+b*EFNB2+c*NCOA7$; wherein a is a number from and between 2.00 to 5.00; b is a number from and between 2.00 and 4.00; c is a number from and between 1.00 and 3.00; EFNB2 is the normalized expression level of EFNB2; and NCOA7 is the normalized expression level of NCOA7. In a particular embodiment the probability of pregnancy (P) is given by the equation $P=a+b*EFNB2+c*NCOA7$; wherein a is a number from and between 3.00 to 4.00; b is a number from and between 2.00 and 3.00; c is a number from and between 1.00 and 2.00. In an even further embodiment a is 3.23; b is 2.57 and c is 1.87 in the foregoing equation.

In one embodiment and departing from the foregoing set of genes, the present invention provides an in vitro model for predicting the competence of a mammalian oocyte to lead to pregnancy and live birth in a subject pretreated with a GnRH (Gonadotropin-releasing Hormone) antagonist and rFSH (recombinant Follicle Stimulating Hormone); said method comprising the steps of:

determining the level of marker gene expression of CAMK1D exon 9, HSPH1 exon 2, and NCOA7 in a sample comprising at least one granulosa or cumulus cell associated with the oocyte comparing the level of marker gene expression with a control of which the competence is known; or normalizing the exon level gene expression of said genes; and evaluating the competence of the oocyte to lead to pregnancy based on said comparison or on said normalized expression levels.

In one embodiment of the foregoing method the competence of the oocyte is based on determining the probability of pregnancy (P) given by the equation $P=a+b*CAMK1D\ exon\ 9+c*HSPH1\ exon\ 2+d*NCOA7$; wherein a is a number from and between −3.00 to −1.00; b is a number from and between 2.00 and 4.00; c is a number from and between 0.00 and 3.00; d is a number from and between 0.00 and 2.00; CAMK1D exon 9 is the normalized expression level of CAMK1D exon 9; HSPH1 exon 2 is the normalized expression level of HSPH1 exon 2; NCOA7 is the normalized expression level of NCOA7; and wherein a positive value refers to pregnancy and a negative value to no pregnancy. In a particular embodiment the probability of pregnancy (P) is given by the equation $P=a+b*CAMK1D\ exon\ 9+c*HSPH1\ exon\ 2+d*NCOA7$: wherein a is a number from and between −2.00 to −1.00; b is a number from and between 1.00 and 2.00; c is a number from and between 0.00 and 1.00; d is a number from and between 0.00 and 1.00. In an even further embodiment a is −1.37; b is 1.79; c is 0.89 and d is 0.74.

In one embodiment and departing from the foregoing set of genes, the present invention provides an in vitro model for predicting the competence of a mammalian oocyte to lead to pregnancy and live birth in a subject pretreated with a GnRH (Gonadotropin-releasing Hormone) antagonist and HP-hMG (highly purified human menopausal gonadotropin); said method comprising the steps of:
  determining the level of marker gene expression of CAMK1D exon 1 and SASH1 in a sample comprising at least one granulosa or cumulus cell associated with the oocyte
  comparing the level of marker gene expression with a control of which the competence is known; or normalizing the exon level gene expression of said genes and
  evaluating the competence of the oocyte to lead to pregnancy based on said comparison or on said normalized expression levels.

In one embodiment of the foregoing method the competence of the oocyte is based on determining the probability of pregnancy (P) given by the equation $P=a+b*SASH1-c*CAMK1D$ exon 1; wherein a is a number from and between 0.00 to 2.00; b is a number from and between 0.00 and 2.00; c is a number from and between 0.00 and 2.00; CAMK1D exon 1 is the normalized expression level of CAMK1D exon 1: SASH1 is the normalized expression level of SASH1; and wherein a positive value refers to pregnancy and a negative value to no pregnancy. In a particular embodiment the probability of pregnancy (P) is given by the equation $P=a+b*SASH1-c*CAMK1D$ exon 1; wherein a is a number from and between 0.00 to 1.00; b is a number from and between 0.00 and 1.00; c is a number from and between 0.00 and 1.00. In an even further embodiment a is 0.47; b is 0.91; and c is 0.0.23.

Comparison of gene expression levels according to the methods of the present invention is preferably performed after the gene expression levels obtained have been corrected for both differences in the amount of sample assayed and variability in the quality of the sample used (e.g., amount and quality of mRNA tested). Normalizing the levels against reference genes in the same sample may carry out correction. Typically☐ "housekeeping genes", such as UBC, B2M, actin, GAPDH, HPRT, CPB. G6PD, histone H2A, or mitochondrial ribosomal protein S 18C gene, in particular UBC or B2M are used for this normalization. Expression levels of a marker gene may be normalized by correcting the absolute expression level of a marker by comparing its expression to the expression of a gene that is not a marker, e.g., a housekeeping gene that is constitutively expressed. Suitable genes for normalization include housekeeping genes such as UBC, B2M, actin, GAPDH. HPRT, CPB. G6PD, histone H2A, or mitochondrial ribosomal protein S 18C gene. This normalization allows amongst others the comparison of the expression level in one sample, e.g., a test sample to a control sample.

Differences in marker gene expression in cumulus cells or granulosa cells associated with a given oocyte, compared to the expression level of cumulus or granulosa cells associated with other oocytes in a group, permits ranking of oocytes in a group of oocytes according to relative quality. Thus, in one embodiment of the invention, a plurality of oocytes from an individual, or group of individuals, are grouped and screened in a single assay; the oocytes characterized with the highest quality probability scores are then selected for fertilization and/or implantation.

The identification of the markers and the determination of the association between change in marker gene expression in cumulus cells and attendant oocyte quality provides the basis for clinical diagnostic kits based on either mRNA or protein expression. Basic materials and reagents required for determination of oocyte quality according to the invention may be assembled in a kit. In certain embodiments, the kit comprises at least one reagent that specifically detects expression levels of at least one gene as disclosed herein, and instructions for using the kit according to one or more methods of the invention. Each kit necessarily comprises reagents which render the procedure specific. Thus, for detecting mRNA expressed by at least one marker gene of the set, the reagent will comprise a nucleic acid probe complementary to mRNA, such as, for example, a cDNA or an oligonucleotide. The nucleic acid probe may or may not be immobilized on a substrate surface (e.g., a microarray). For detecting a polypeptide product encoded by at least one gene of the set, the reagent will comprise an antibody that specifically binds to the polypeptide. Depending on the procedure, the kit may further comprise one or more of: ☐ extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may also be included in the kit. Reagents may be supplied in a solid (e.g., lyophilized) or liquid form. Kits of the present invention may optionally comprise different containers (e.g., vial, ampoule, test tube, flask or bottle) for each individual buffer and/or reagent. Other containers suitable for conducting certain steps for the disclosed methods may also be provided. In certain embodiments, the kits of the present invention further comprise control samples. Instructions for using the kit according to one or more methods of the invention may comprise instructions for processing the cumulus cell or granulosa cells samples, and/or performing the test, and instructions for interpreting the results, i.e. to decide on the competence of the oocyte to lead to childbirth, to implantation, to form a pre-implantation blastocyst or embryo, and/or to lead to fertilization. In one embodiment, a kit for determining mRNA expression of marker genes by quantitative RT-PCR would include standard primers and other reagents for performing quantitative RT-PCR, with reaction components formulated for optimized success in detection for each gene to be assayed. The amplification primers may be selected based on the nucleotide sequence of the relevant marker gene(s), depending on the species of mammalian oocyte being assessed. Any single or combination of the marker genes could be incorporated into the kit. To provide users options to choose balance between coverage and cost, different kits could provide different collections of primers for the marker genes targeted for analysis.

Possible Applications of the Method According to this Invention

In preferred embodiments, the inventive methods may also be used to identify women subjects who produce or do not produce pregnancy competent oocytes based on the levels of expression of a set of differentially expressed genes. However, the inventive methods are applicable to non-human animals as well, e.g., other mammals, avians, amphibians, reptiles, et al. For example, the subject invention may be used to derive animal models for the study of putative female fertility treatments.

Additionally, the present invention may be used to identify female subjects who have an abnormality that precludes or inhibits their ability to produce pregnancy competent oocytes, e.g., exposure to medication, exposure to toxicants, environmental factors, ovarian dysfunction, ovarian cyst, pre-menopausal or menopausal condition, cancer, autoimmune disorder, hormonal dysfunction, cell proliferation disorder, or another health condition that inhibits or precludes the development of pregnancy competent oocytes. □ □ For example, subjects who do not express specific pregnancy signature genes at characteristic expression levels may be screened to assess whether they have an underlying health condition that precludes them from producing pregnancy competent oocytes. Particularly, such subjects may be screened to assess whether they are exhibiting signs of menopause, whether they have a cancer, autoimmune disease or ovarian abnormality, e.g., ovarian cyst, or whether they have another health condition, e.g., hormonal disorder, allergic disorder, etc., that may preclude the development of "pregnancy competent" oocytes.

Additionally, the subject methods may be used to assess the efficacy of putative female fertility treatments in humans or non-human female subjects. Essentially, such methods may comprise treating a female subject, preferably a woman, with a putative fertility enhancing treatment, isolating at least one oocyte and associated surrounding follicular or granulosa cells from said woman after treatment, optionally further isolating at least one oocyte and associated surrounding cells prior to treatment, isolating at least one cumulus cell from each of said isolated oocytes; detecting the levels of expression of at least one gene that is expressed or not expressed at characteristic levels by cumulus cells that are associated with (surround) pregnancy competent oocytes; and assessing the efficacy of said putative fertility treatment based on whether it results in cumulus cells that express at least one pregnancy signature gene at levels more characteristic of cumulus cells that surround pregnancy competent oocytes (than without treatment). As noted, while female human subjects are preferred, the subject methods may be used to assess the efficacy of putative fertility treatments in non-human female animals, e.g., female non-human primates or other suitable animal models for the evaluation of putative human fertility treatments.

Still further, the present invention may be used to enhance the efficacy of in vitro or in vivo fertility treatments. Particularly, oocytes that are found to be "pregnancy incompetent", or are immature, may be cultured in a medium containing one or more gene products that are encoded by genes identified as being "pregnancy signature" genes, e.g., hormones, growth factors, differentiation factors, and the like, prior to, during, or after in vivo, or in vitro fertilization. Essentially, the presence of these gene products should supplement for a deficiency in nutritional gene products that are ordinarily expressed by cumulus and/or granulosa cells that surround "pregnancy competent" oocytes, and which normally nurture oocytes and thereby facilitate the capability of these oocytes to yield viable pregnancies upon fertilization.

Alternatively, one or more gene products encoded by said pregnancy signature genes may be administered to a subject who is discovered not to produce pregnancy competent oocytes according to the methods of the invention. Such administration may be parenteral. e.g., by intravenous, intramuscular, intravaginal, subcutaneous injection or by oral or transdermal administration. Alternatively, these gene products may be administered locally to a target site, e.g., a female ovarian or uterine environment. For example, a female subject may have her uterus or ovary implanted with a drug delivery device that provides for the sustained delivery of one or more gene products encoded by "pregnancy signature" genes.

As detailed above, differences in marker gene expression in cumulus cells or granulosa cells associated with a given oocyte, compared to the expression level of cumulus or granulosa cells associated with other oocytes in a group, permits ranking of oocytes in a group of oocytes according to relative quality. Thus, in one embodiment of the invention, a plurality of oocytes from an individual, or group of human or non-human female subjects, are grouped and screened in a single assay; the oocytes characterized with the highest quality probability scores are then selected for fertilization and/or implantation.

EXAMPLES

Example 1

QPCR Analysis

Material and Methods
Patient Population

This study was approved by the Ethical Committee of the UZBrussel and the patients written consent was obtained. Forty seven ICSI patients were selected based on the embryo transfer policy (single embryo transfer) and ovarian stimulation protocol prescribed: GnRH antagonist in combination with recombinant follicle stimulating hormone (FSH) (Gonal-f. Merck-Serono, Geneva. Switzerland; n=4 or Puregon, MSD, Oss, The Netherlands; n=43). Causes of infertility were: male factor only (n=19), female factor only (ovulation disorder n=3 and tubal infertility n=2), combination male and female factor (OAT and endometriosis n=3) and idiopathic (n=20). Twenty patients had single embryo transfer on day 3 of culture, from these 10 became pregnant. Twenty seven patients had transfer on day 5, from these 9 became pregnant.

Collection of Human Cumulus Cells and Embryo Culture

Vaginal ultrasound was used to monitor follicular development. The endocrine profile was monitored by analysis of serum 17β-estradiol (E2), progesterone, FSH and LH by electrochemiluminescence on a COBAS 6001 immunoanalyser (Roche, Roche Diagnostics. Mannheim, Germany) using validated assays with respectively sensitivities of 5 ng/l, 0.03 µg/l, <0.1 IU/l, 0.1 IU/l and total imprecisions (% CV) of respectively <6, <7, <6 and <6. Final follicular maturation was induced with a dose of 10 000 IU hCG when at least three follicles of 17 mm in diameter were observed by transvaginal ultrasound. Oocyte retrieval was done 36 h later. CC collection was done as described in (Wathlet et al. 2011). Briefly, individual oocyte denudation was performed in 40 µl droplets of HTF-SSS containing 80 IU/ml Cumulase (MediCult, Lyon, France) for not longer than 30 s and washed sequentially in droplets without enzyme. At any time, oocytes were handled individually from this point onwards in order to allow retrospective analysis of the CC per oocyte. After denudation, the CC were plunged directly in liquid nitrogen. ICSI was performed as described previously (Van Landuyt et al. 2005) and embryos were cultured in sequential media of SAGE (CooperSurgical, Leisegang Medical, Berlin). Embryos were vitrified on day 3 or day 5/6 of embryo culture as was described earlier (Van Landuyt et al. 2011) and used in a subsequent FRET cycle.

Figure 1:
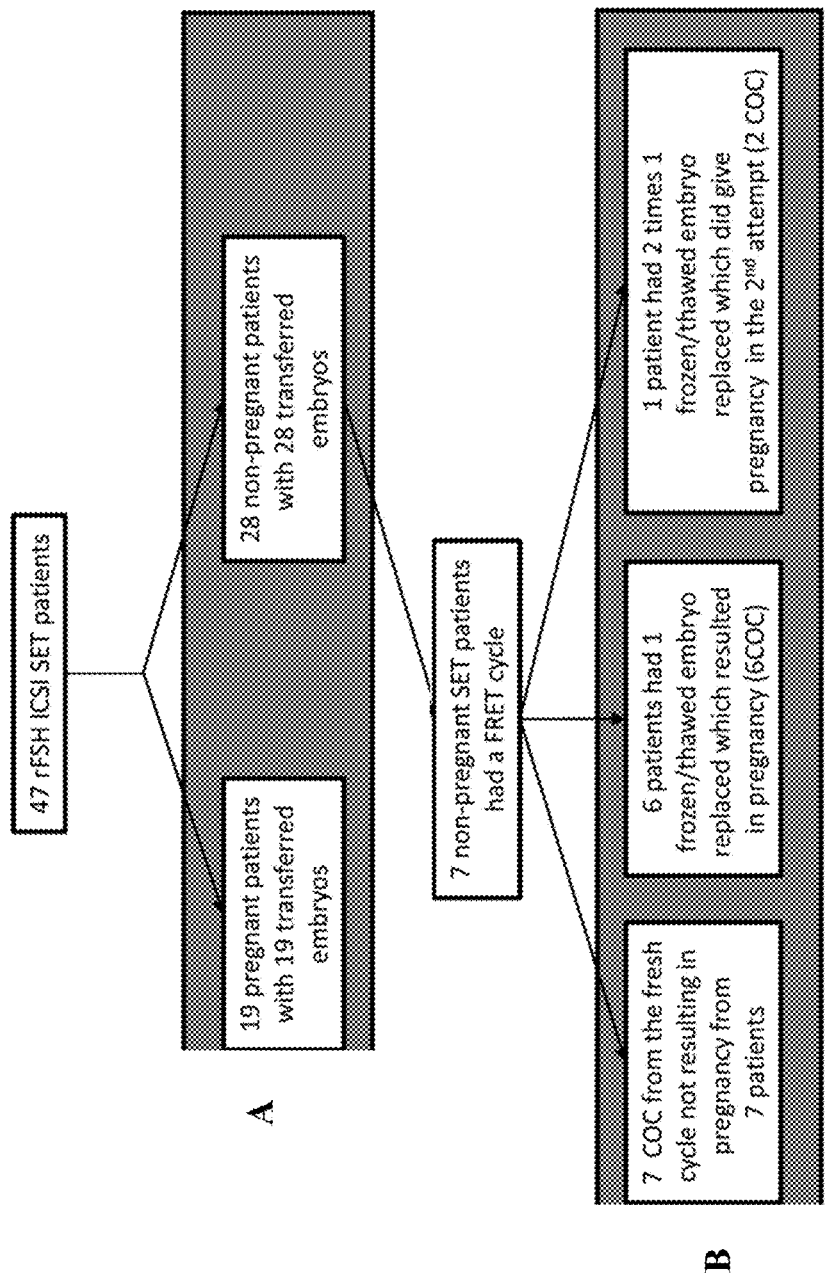
FIG. 1: Overview of the samples used in this study.

For all 47 patients, only the CC related to those oocytes resulting in embryos selected for transfer were analyzed exception made for 7 of the 28 non-pregnant patients, 1 extra CC sample (except for 1 patient, 2 CC samples) related to a vitrified embryo giving pregnancy after a frozen single-embryo transfer cycle, was analyzed (8 extra CC in total from 7 patients). FIG. 1 shows the different samples used for each analysis.

Gene Selection

This study is the 3rd one in a row to evaluate the predictive value of CC gene expression for oocyte quality using QPCR. Over the 3 studies, we followed a precise strategy to choose which genes to analyze regarding to oocyte quality in ICSI patients. The first study identified 4 top genes, 2 predictive for embryo morphology (inositol-trisphosphate 3-kinase A (ITPKA) and transient receptor potential cation channel, subfamily M, member 7 (TRPM7)) and 2 for pregnancy outcome (syndecan 4 (SDC4) and versican (VCAN)). It was chosen to include those 4 genes in the next study (Wathlet et al. 2012). ITPKA and TRPM7 were again related to embryo development, but SDC4 and VCAN were not retained this time in the pregnancy models and were replaced by EFNB2, CAMK1D and STC1 when using stepwise multiple regression analysis. As several studies showed no relation between the genes predictive for embryo development and pregnancy outcome (Gebhardt et al. 2011; Wathlet et al. 2012), it was decided to repeat only the 3 pregnancy related genes in this third study. Our hypothesis is that by this 'cascade' testing strategy, the strongest pregnancy predictive genes may be filtered out through the consecutive studies (Table 2). The other 9 genes analyzed in this study were: GSTA3, GSTA4, GPX3, GSR, ITPR1, SLC2A1, THBS1, TGFB1 and PGR (Table 1).

TABLE 1

Genes analyzed in cumulus cells for pregnancy prediction.

| Gene symbol (name) | General Function | Previously described as oocyte quality marker in human CC | References |
|---|---|---|---|
| EFNB2 (ephrin-B2) | B-Class Ephrins are transmembrane proteins possibly involved in luteinization events | Higher in the CC of pregnant ICSI patients | (Egawa et al. 2003) (A) (Wathlet et al. 2012) (B) |
| CAMK1D (calcium/calmodulin-dependent protein kinase ID | Member of the Ca2+/calmodulin-dependent protein kinase 1 subfamily of serine/threonine kinases | Higher in the CC of pregnant ICSI patients | (Verploegen et al. 2000) (A) (Wathlet et al. 2012) (B) |
| STC1 (stanniocalcin 1) | Decreases FSH induced progesterone production in rat granulosa cell cultures | Tended to be lower in pregnant ICSI patients | (Luo et al. 2004; Luo et al. 2005) (A) (Wathlet et al. 2012) (B) |
| GSR (glutathione reductase) | Cellular antioxidant defense enzyme | Not yet described | (Pastore et al. 2003) (A) |
| GPX3 (glutathione peroxidase 3) | Helps in the detoxification of hydrogen peroxide | Negative predictor for early cleavage embryos | (Pastore et al. 2003) (A) (van Montfoort et al. 2008) (B) |
| GSTA3 (glutathione S-transferase alpha 3) | Detoxification function next to a function in progesterone production | Not yet described | (Pastore et al. 2003; Raffalli-Mathieu et al. 2008) (A) |
| GSTA4 (glutathione S-transferase alpha 4) | Detoxification function | Not yet described | (Pastore et al. 2003) (A) |
| TGFB1 (transforming growth factor, beta 1) | Can play a role in cell proliferation and differentiation. It was shown to be related to follicle development in adult mice. | Not yet described | (Govinden and Bhoola 2003; Liu et al. 1999; Verploegen et al. 2000) (A) |
| PGR (progesterone receptor) | Anti-apoptotic effect through the binding of progesterone in cultured human granulosa cells | Lower expressed in good morphology blastocysts. Up-regulated in follicular cells of pregnant patients (array results) | (Makrigiannakis et al. 2000) (A) (Hamel et al. 2010b; Hasegawa et al. 2005) (B) |
| ITPR1 (inositol 1,4,5-trisphosphate receptor, type 1 | Receptor for inositol 1,4,5-triphsopahte, releasing calcium from the endoplasmatic reticulum | Up-regulated in non-early cleavage embryos (array results) | (Berridge 2009) (A) (van Montfoort et al. 2008) (B) |
| SLC2A1 (solute carrier family 2 (facilitated glucose transporter), member 1) | Glucose transporter responsible for the facilitated transport of glucose through the plasma membrane of mammalian cells | Not yet described | (Olson and Pessin 1996) (A) |
| THBS1 (thrombospondin 1) | Can mediate cell-cell and cell-matrix interactions. Can activate TGFB1 | Not yet described | (Adams 1997; Hayashi et al. 2012) (A) |
| SASH1 (SAM and SH3 domain containing 1) | 1.1. Acts downstream of TLR4, the Toll-like receptor involved in the cytokine production | Not yet described | (Dauphinee et al. 2013) (A) |
| SPTBN5 (spectrin, beta, non-erythrocytic 5) | 1.2. Relates the epidermal growth factor (EGF) response | Not yet described | (Odell AF 2008) (A) |
| DNAH3 (dynein, axonemal, heavy chain 3) | The exact function is currently unknown | Not yet described | |
| GALNTL6 (UDP-N-acetyl-alpha-D-galactosamine: polypeptide N-acetylgalactosaminyltransferase-like 6) | The exact function is currently unknown | Not yet described | |
| NCOA7 (nuclear receptor coactivator 7) | Regulates the estrogen receptor-signal | Not yet described | (Halachmi S et al. 1994 Kawagoe et al. 2012) (A) |
| MROH9 (maestro heat-like repeat family member 9) | The exact function is currently unknown | Not yet described | |

(A) Refers to information from the 'General Function' column;
(B) Refers to the information from the 'Previously described as oocyte quality marker in human CC' column;
CC: cumulus cells;
FSH: Follicle stimulating hormone;
ICSI: Intra-cytoplasmic sperm injection

TABLE 2

Strategy over 3 studies to obtain the strongest quality related genes on stored cumulus cells from ICSI patients

|  | Wathlet et al. 2011 | Wathlet et al. 2012 | Current study |
|---|---|---|---|
| Genes tested with QPCR | SDC4, VCAN, ITPKA, TRPM7, PTGS2, GREM1, CALM2, ALCAM | SDC4, VCAN, ITPKA, TRPM7, CAMK1D, EFNB2, STC1, STC2, CYP11A1, HSD3B1, PTHLH | CAMK1D, EFNB2, STC1, GSTA4, GSTA3, GSR, GPX3, PGR, THBS1, SLC2A1, ITPR1, TGFB1 |
| Stimulation protocol | antagonist rFSH (25 patients) agonist HP-hMG (20 patients) | Antagonist rFSH (33 patients) | Antagonist rFSH (47 patients) |
| Embryo culture medium | BlastAssist System (Medicult) | Vitrolife G7 (Vitrolife) | SAGE (CooperSurgical) |
| End points | Embryo morphology (75 CC for rFSH and 67 CC for HP-hMG from 2 × 10 patients). Clinical pregnancy (42 patients of both stimulation protocols of which 19 pregnant = 19 COC) | Embryo morphology (99 CC). Biochemical and live birth pregnancy (16 pregnant, 17 non-pregnant = 33 COC) | Live birth pregnancy inter-patient analysis (19 live birth, 28 non-pregnant = 47 COC). Pregnancy Intra-patient (7 patients with 2 or 3 CC from the same retrieval cycle) |
| Best genes retained for next study | Pregnancy prediction: SDC4 and VCAN. Embryo morphology prediction: ITPKA and TRPM7 | Pregnancy prediction: CAMK1D, EFNB2 and STC1 | To be determined in the current study |

The gene expression of cumulus cells (CC) related to different embryo morphology or pregnancy outcome of the corresponding oocytes in ICSI was assessed for three gene panels on three different sample sets. The genes found most predictive in each sample set were tested in the subsequent independent patient samples set. Genes marked in bold were retained as best predictive genes from the previous study. MII: metaphase II oocytes; COC: cumulus oophorus complex; rFSH: recombinant Follicle Stimulating Hormone; HP-hMG: Highly Purified human Menopausal Gonadotropin RNA Extraction and cDNA Synthesis Total RNA was extracted as described earlier (Adriaenssens et al. 2010) using the RNeasy Micro Kit (Qiagen, Westburg, Leusden, The Netherlands) including a DNase step and addition of 5 ng/µl poly(dA) (Roche Applied Science, Mannheim, Germany) prior to extraction. Extraction was followed by a second DNase treatment (RQ1 RNase-Free DNase, Promega, Leiden, The Netherlands).

Reverse transcriptase (RT) was done as previously described (Adriaenssens et al. 2010) with the iScript cDNA Synthesis Kit (Bio-Rad Laboratories, Ghent, Belgium). Negative controls were generated by omitting the enzyme or the RNA in the RT reaction.

Real-Time PCR

Primer sequences for CAMK1D, STC1 and EFNB2 are listed in Wathlet et al 2012. Primers for GPX3, GSTA3, GSTA4, PGR, THB1, ITPRA, SLC2A1, GSR and TGFb1 can be found in Table 3. Both beta-2-microglobulin (B2M) and ubiquitin C (UBC) were validated and used before as normalization factor (Wathlet et al. 2011). Cycling conditions, negative controls, standard curves and normalization (with B2M and UBC) are as described earlier (Wathlet et al. 2011), but all PCR reactions were adapted to 10 µl reactions. All values mentioned hereafter are the normalized values to the mean of both B2M and UBC for each sample.

TABLE 3

Primer sequences.

| Gene Symbol | Reference Sequence Gene name | Forward and Reverse primer 5'→3' | SEQ ID No |
|---|---|---|---|
| GPX3 | NM_002084 | ggggacaagagaagtcgaaga | 1 |
|  |  | gccagcatactgcttgaagg | 2 |
| GSR | NM_000637 | caatgatcagcaccaactgc | 3 |
|  |  | agtcttttaacctccttgacctg | 4 |
| GSTA3 | NM_000847 | gatgccaagattgccttgat | 5 |
|  |  | ttgtccatggctctgtaacact | 6 |
| GSTA4 | NM_001512 | cctcaaggagagaaccctgat | 7 |
|  |  | ggatgcatgataagcagttcc | 8 |

TABLE 3-continued

Primer sequences.

| Gene Symbol | Reference Sequence Gene name | Forward and Reverse primer 5'→3' | SEQ ID No |
|---|---|---|---|
| ITPR1 | NM_002222 | tacccagcggctgctaac | 9 |
|  |  | tgcaaatcctgctcctctgt | 10 |
| PGR | NM_000926 | gtcatagaccccgttgcta | 11 |
|  |  | gctaagccagcaagaaatgg | 12 |
| SLC2A1 | NM_006516 | gtctggcatcaacgctgtc | 13 |
|  |  | acgataccggagccaatg | 14 |
| TGFB1 | NM_000660 | agtggttgagccgtggag | 15 |
|  |  | gcagtgtgttatccctgctg | 16 |
| THBS1 | NM_003246 | aatgctgtcctcgctgttg | 17 |
|  |  | gccacagctcgtagaacagg | 18 |

Statistics

Inter-Patient Analysis

In a first analysis, a two-tailed t-test (GraphPad Prism version 4.01 for Windows, GraphPad Software, San Diego Calif. USA) was used to compare cumulus complexes of oocytes resulting in pregnancy or not (19 live birth, 28 non-pregnant). All data were LOG transformed to obtain normal distribution. Since multiple genes were tested, the Bonferroni correction allowed us to consider only P-values <0.0042 were considered significant after Bonferroni correction.

In a second analysis, a model was built using stepwise multiple regression analysis as described earlier (Wathlet et al. 2011). Briefly, a linear regression model, with an equation as output 'y=a+bx+cz+ds+et+fu+gv+hw', was built with as response variables (x, z, s, t, u, v, w) gene expression and/or patient and cycle characteristics (all are listed in Table 3). 'b-h' are the respective indexes of the included variables and 'a' is the intercept of the equation. A variable was added to the model if the type III P-value of the variable was <0.3 and if the P-value of the model was improved. At the end of the model a backwards regression step was performed to exclude redundant variables. Four different models were built to predict pregnancy. In two models only gene expression values were allowed (first the model was restricted to 3 genes, next all genes were allowed into the models as long as they improved the P-value of the model). In two other models, the need for correction by patient and cycle characteristics was assessed by allowing all patient and cycle characteristics to the models only composed of genes, when those extra variables could improve the model. By introducing those extra factors, possible inter-patient variability on gene expression could be leveled out and increase the differences related to oocyte quality.

For all models, accuracy ((True positive+true negative)/(true positive+false positive+false negative+true negative)) and positive and negative predictive values (PPV=True positive/(true positive+false negative) and NPV=True negative/(true negative+false positive) were calculated. The power of all models was represented by Receiver Operating Characteristic (ROC) and the area under curve (AUC) was calculated.

taining only genes and built on the 47 CC samples (19 live birth), but excluding the 8 CC samples from the frozen cycles.

Results

Patient Population

No statistical differences were found between the patient and cycle characteristics of the pregnant and the non-pregnant groups (Table 3). Mean age and BMI for both groups of patients was low but comparable. Progesterone levels were low in both groups. Mean cycle number attempt was not different in both groups: respectively in the pregnant and non-pregnant group 12 and 17 patients underwent their first cycle, 6 and 10 their second cycle and 1 for both groups their third cycle. Percentages of oocyte maturity and fertilization were normal in both groups, and the percentage of good quality embryos on day 3 was more than 50%. Embryo quality score on moment of transfer was not different for both groups. Nineteen fresh SET cycles resulted in live birth.

TABLE 3

Patient and cycle characteristics.

| Variable | Unit | Pregnant average | SD | n | Non-pregnant average | SD | n | t-test |
|---|---|---|---|---|---|---|---|---|
| Age | Year | 30 | 4 | 19 | 31 | 5 | 28 | ns |
| BMI | kg/m2 | 23 | 4 | 17 | 23 | 4 | 25 | ns |
| Days of stimulation | # | 9 | 2 | 19 | 8 | 1 | 28 | ns |
| Gonadotrophine dose | U/day | 167 | 34 | 19 | 169 | 36 | 28 | ns |
| FSH$^a$ | U/l | 11 | 3 | 16 | 12 | 4 | 26 | ns |
| LH$^a$ | U/l | 1.88 | 1.46 | 10 | 1.18 | 0.86 | 24 | ns |
| Relative E2 | ng/l | 150 | 98 | 16 | 162 | 87 | 26 | ns |
| Progesterone$^a$ | μg/l | 0.79 | 0.26 | 16 | 0.77 | 0.42 | 26 | ns |
| COC retrieved at pick up | # | 10 | 5 | 19 | 9 | 5 | 28 | ns |
| Ovarian Response | # | 6 | 3 | 19 | 6 | 3 | 28 | ns |
| Oocyte Maturity | % | 89 | 10 | 19 | 80 | 15 | 28 | ns |
| 2PN | % | 82 | 15 | 19 | 87 | 16 | 28 | ns |
| ≥7cell day 3 | % | 74 | 25 | 19 | 72 | 29 | 28 | ns |
| Low Fragmentation | % | 65 | 30 | 19 | 73 | 29 | 28 | ns |
| Good Quality Embryos | % | 58 | 17 | 19 | 53 | 29 | 28 | ns |

COC: cumulus oocyte complex;
Relative E2: E2/COC retrieved;
Ovarian Response: (COC retrieved/Gonadotrophine dose) × 100;
Oocyte Maturity: proportion of MII/COC retrieved;
2PN: proportion of 2PN/intact oocytes after ICSI;
≥7cell day 3 = proportion of embryos with at least 7 cells on day 3/2PN;
Low Fragmentation: proportion of embryos with <10% fragmentation on day 3/2PN;
Good Quality Embryos: proportion of embryos on day 3 with <10% fragmentation and at least 7 cells/2PN;
$^a$Serum values as measured on day of hCG;
ns: P > 0.05;
SD = standard deviation.

Intra-Patient Analysis

Finally, the study allowed comparing 2 (or 3) oocytes originating from one oocyte retrieval cycle with known pregnancy outcome per oocyte, as all embryos were transferred individually in consecutive cycles. For this purpose, from 7 of the 28 patients that were not pregnant in the fresh cycle, the CC of the embryos that were replaced in a subsequent frozen single embryo transfer cycle resulting in pregnancy were compared to those transferred in the fresh cycle. For one patient, two consecutive frozen embryo replacement cycles were analyzed as the first embryo did not end in a pregnancy. Seven genes were chosen for this analysis based on their presence in one of the above mentioned models or their P-value of addition, when first added to a pregnancy model. A paired t-test was performed for each gene and the chance to pregnancy was calculated with the earlier defined models from the inter-patient analysis, con- Pregnancy Prediction Validation of predictive genes (CAMK1D, EFNB2 and STC1) using a model built on a previous sample set A model predicting pregnancy composed of 3 genes, considered in a previous study (Wathlet et al. 2012), was tested in the current, independent patient series. The gene expression values for CAMK1D, EFNB2 and STC1 of the CC of the 47 patients were introduced in the equation obtained before and gave a value predicting the chance to pregnancy for each of the 47 oocytes. The obtained PPV and NPV calculated with the 47 samples of this study were 62% and 86%, with an accuracy of 72%.

Inter-Patient Analysis: t-Test of all 12 Genes in the Current Sample Set

The cumulus complexes of 28 oocytes not resulting in pregnancy were compared to 19 CC of oocytes that resulted in a live birth. Only EFNB2 was statistically higher in the pregnant group. CAMK1D, GSTA4 and GSR only showed a trend of higher expression in the pregnant group (respective P-values: 0.0068, 0.0123 and 0.0507). Graphs for all genes can be found in FIGS. 2A-2B.

Inter-Patient Analysis: Stepwise Multiple Regression Analysis

In a first step to build a pregnancy model, the P-value of addition when added as first variable was calculated for all genes and can be found in Table 4.

TABLE 4

P-value of addition for the different genes tested.

| Variable | P-value of addition |
|---|---|
| EFNB2 | 0.01 |
| GSTA4 | 0.01 |
| GPX3 | 0.04 |
| CAMKID | 0.05 |
| GSR | 0.06 |
| PGR | 0.16 |
| STC1 | 0.38 |
| TGFB1 | 0.43 |
| ITPR1 | 0.50 |
| SLC2A1 | 0.61 |

TABLE 4-continued

P-value of addition for the different genes tested.

| Variable | P-value of addition |
|---|---|
| THBS1 | 0.68 |
| GSTA3 | 0.75 |

The P-value of addition is obtained when each gene is inserted as first variable in a pregnancy model. The genes are ordered with increasing P-value.

First, the model was restricted to the inclusion of 3 of the 12 genes (Model 1). EFNB2. GSTA4 and PGR were retained and gave a model with a P-value of 0.0015, a PPV of 68%, a NPV of 79% an accuracy of 73% and an AUC of 0.82. When trying to improve this model by also allowing patient and cycle characteristics (from Table 3), no improvement on the previous model was found (Model 1 bis).

In a next step, more than 3 genes were allowed into the model if improving the P-value (Model 2). Five of the 12 genes were retained in this model (i.e. EFNB2, GSTA4. PGR, GPX3 and GSTA3) which yielded a P-value <0.0001 with a PPV of 78%, a NPV of 83%, an accuracy of 81% and an AUC of 0.93. Adding patient and cycle characteristics improved the model (Model 3). The retained parameters were: days of stimulation, relative E2 and age. The PPV, NPV and accuracy of the extended model all increased to 93% and the AUC to 0.95 (Table 5). Full mathematical models can be found in Table 6. ROC curves are shown in FIG. 3.

TABLE 5

Schematic overview of the multiparametric models for live birth prediction.

| | Total # of patients | # of pregnant patients | GPX3 | GSTA3 | GSTA4 | PGR | EFNB2 |
|---|---|---|---|---|---|---|---|
| Model 1 (3 genes) | 47 | 19 | | | $x^a$ | x | $x^a$ |
| Model 1 bis (Model 1 + patient and cycle parameters) | cycle and patient parameters could not improve the first model | | | | | | |
| Model 2 (unlimited # of genes) | 47 | 19 | $x^a$ | $x^a$ | $x^a$ | x | x |
| Model 3 (Model 2 + patient and cycle parameters) | 42* | 16 | $x^a$ | $x^a$ | $x^a$ | $x^a$ | $x^a$ |

| | AGE | Rel E2 | # Days stim | P model | PPV (%) | NPV (%) | Accuracy (%) | AUC |
|---|---|---|---|---|---|---|---|---|
| Model 1 (3 genes) | | | | 0.0015 | 68 | 79 | 73 | 0.82 |
| Model 1 bis (Model 1 + patient and cycle parameters) | cycle and patient parameters could not improve the first model | | | | | | | |
| Model 2 (unlimited # of genes) | | | | 0 | 78 | 83 | 81 | 0.93 |
| Model 3 (Model 2 + patient and cycle parameters) | x | x | x | 0 | 93 | 93 | 93 | 0.95 |

Only genes and factors that were at least retained once are listed. In Model 1 a maximum of three genes were retained to finalize the model. In Model 2 an unlimited number of genes were allowed into the model, if they could improve the P-value of the model. To try to improve Model 1 and Model 2 patient and cycle characteristics from Table 3 were allowed into the model. Only Model 2 could be improved and resulted in Model 3.
x: factor significantly improving the model;
: number; 'unlimited' refers to the fact that all 12 genes were allowed into the model if they could improve the model;
stim: ovarian stimulation;
PPV: positive predictive value;
NPV: negative predictive value;
AUC: Area under the curve;
[a] Final type-III P-value < 0.01 in the model;
*only 42 patients were included to build this model as E2 values on day of hCG were missing for 5 patients.

TABLE 6

Mathematical models for pregnancy prediction.

| | |
|---|---|
| Model 1 (max 3 genes) = | $-2.25846 + 0.79256 \times EFNB2 + 0.09491 \times GSTA4 - 0.09632 \times PGR$ |
| Model 1bis (max 3 genes + parameters Table 3) = | cycle and patient parameters could not improve the first model |
| Model 2 (unlimited # of genes) = | $-1.02049 + 0.63484 \times EFNB2 + 0.27346 \times GSTA4 - 0.10864 \times PGR - 0.43395 \times GPX3 - 0.51067 \times GSTA3$ |
| Model 3 (unlimited # of genes + parameters Table 3) = | $-11.26732 + 1.3462 \times EFNB2 + 0.45884 \times GSTA4 - 0.2423 \times PGR - 0.65786 \times GPX3 - 0.85875 \times GSTA3 + 0.49709 \times$ days of stimulation $+ 0.0092 \times$ Rel E2 $+ 0.13864 \times$ age |

Full mathematical models used to predict pregnancy outcome using cumulus cell gene expression values and patient and cycle characteristics.
: number Intra-Patient Pregnancy Prediction For seven patients, cryostored CC samples related to cryopreserved embryos which had led to a clinical pregnancy after transfer in a subsequent transfer cycle were analyzed. This material was used to analyze the genes present in the above obtained multiparametric models (Table 6) and/or the 5 genes with the smallest P-value of addition (Table 4) i.e. CAMK1D, EFNB2, GPX3, GSR, GSAT4, GSTA3 and PGR. As a first explorative method a paired t-test for those seven genes was performed and can be found in FIGS. 4A-4D. Five genes had an upwards trend in the CC of an oocyte resulting in pregnancy (P-value <0.05; only P-values <0.07 are significant after Bonferroni correction for multiple comparisons): EFNB2 (only significant difference between pregnant and non-pregnant), CAMK1D, GSR and PGR. GSTA4, GPX3 and GSTA3 had all P-values >0.05. Fold changes between the CC from the same patient were calculated and an average per gene was made (from 1.1 to 2.5) (Table 7). For the five genes with a P-value <0.1 in the paired t-test, the percentage of correctly estimated CC was 71% to 88%, based on the level expected (e.g. higher expression is expected in the pregnant compared to the non-pregnant related CC) from the paired t-test. In a next step the predictive power of the multiparametric models (the 3 gene model (=Model 1) and the 5 gene model (=Model 2)) obtained in the inter-patient analysis (47 CC samples) was used to rank the CC of each patient (Table 6) for their chance to pregnancy. As all patient and cycle characteristics are identical for oocytes within a single retrieval cycle it makes obviously no sense to use models containing those variables. All CC, except for patient 4, were correctly ranked (Table 7) for their chance to pregnancy.

TABLE 7

Comparison of gene expression levels of fresh cycles not resulting in pregnancy to frozen transfer cycles resulting in pregnancy (Intra-patient analysis).

| | | | Single gene analysis | | | | | | | Multiparametric Model 1 Ranking | Model 2 Ranking |
|---|---|---|---|---|---|---|---|---|---|---|---|
| | Fresh/FRET | Outcome | EFNB2 | CAMK1D | GSR | PGR | GSTA4 | GSTA3 | GPX3 | | |
| Patient 1 | Fresh | not pregnant ratio | 3.4 | 3.5 | 1.8 | 2.1 | 1.4 | 5.4 | 0.7 | 2 | 2 |
| | FRET | clinical pregnancy | | | | | | | | 1 | 1 |
| Patient 2 | Fresh | not pregnant ratio | 4.9 | 4.9 | 2.3 | 4.0 | 2.6 | 0.0 | 2.9 | 2 | 2 |
| | FRET | clinical pregnancy | | | | | | | | 1 | 1 |
| Patient 3 | Fresh | not pregnant ratio | 1.8 | 1.8 | 1.6 | 1.8 | 1.4 | 0.0 | 0.6 | 2 | 2 |
| | FRET | clinical pregnancy | | | | | | | | 1 | 1 |
| Patient 4 | Fresh | not pregnant ratio | 1.6 | 1.8 | 1.4 | 3.6 | 0.7 [a] | 1.1 | 1.0 | 1 [b] | 1 [b] |
| | FRET | clinical pregnancy | | | | | | | | 2 [b] | 2 [b] |
| Patient 5 | Fresh | not pregnant ratio | 4.1 | 3.2 | 4.1 | 1.5 | 1.2 | 1.2 | 1.0 | 2 | 2 |
| | FRET | Live birth | | | | | | | | 1 | 1 |
| Patient 6 | Fresh | not pregnant ratio | 1.4 | 1.3 | 1.3 | 1.0 [a] | 1.3 | 1.2 | 0.8 | 3 | 3 |
| | FRET | not pregnant ratio | 1.0 [a] | 0.6 [a] | 0.6 [a] | 0.7 [a] | 0.9 [a] | 0.8 | 0.6 | 2 | 2 |
| | FRET | clinical pregnancy | | | | | | | | 1 | 1 |
| Patient 7 | Fresh | not pregnant ratio | 2.3 | 2.8 | 2.9 | 2.8 | 3.1 | 1.6 | 1.3 | 2 | 2 |
| | FRET | Live birth | | | | | | | | 1 | 1 |
| Based on the paired t-test expected higher in: | | | pregnant | pregnant | pregnant | pregnant | pregnant | nlr | nlr | | |
| Average: | | | 2.5 | 2.5 | 2.0 | 2.0 | 1.6 | 1.6 | 1.1 | | |
| Min: | | | 1.0 | 0.6 | 0.6 | 0.6 | 0.7 | 0.7 | 0.6 | | |
| Max: | | | 4.9 | 4.9 | 4.1 | 4.1 | 3.1 | 3.1 | 2.9 | | |
| % corrected predictions based on expression level: | | | 86 | 86 | 86 | 86 | 71 | na | na | 86% | 86% |
| P-value paired t-test: | | | 0.006 | 0.026 | 0.037 | 0.033 | 0.074 | ns | ns | | |

This Table gives an overview of the Intra-patient analysis. Each line represents one cumulus complex. Per patient 2 or 3 cumulus complexes from 1 retrieval cycle were analyzed. Ratios of gene expression levels are always pregnant over non-pregnant. For patient 6, the cumulus complex of the pregnant FRET cycle was compared to the cumulus complexes of the fresh and the FRET non-pregnant cycle. Model 1 and 2 are respectively the models built up with 3 and 5 genes from Table 5. Ranking was obtained by inserting the expression values in the mathematical models from Table 6. Rank number '1' is the oocyte with the highest chance to achieve pregnancy.

ns: not significant; na: not applicable; nlr: no linear relation.

[a] the expression value is not higher or lower between pregnant and non-pregnant as expected based on the earlier results.

[b] the ranking is not correct using the multiparametric models.

FRET: frozen embryo transfer cycle.

Discussion

The expression of 12 genes in the CC and their capacity to predict the pregnancy potential of the oocyte they surrounded were analyzed in the present study. Three genes (CAMK1D, EFNB2 and STC1) were included from a previous study (Wathlet et al. 2012), where they were coming out as the most predictive ones for pregnancy prediction. EFNB2 was also significantly up-regulated in the current study in the CC from the oocytes that gave pregnancy and CAMK1D showed the same trend (P=0.0068). The model composed of genes only from the previous patient dataset, using CAMK1D, EFNB2 and STC1, was validated in this independent patient group and yielded a similar overall performance of the model, with accuracies of 72% in the current study and 79% in the previous study.

Besides the EFNB2 and CAMK1D coming from our previous study, two newly studied genes, GSTA4 and GSR, also showed an up-regulated trend in the CC of the pregnant group.

A multiparametric approach tested whether it would be possible to predict live birth by using only 3 of the 12 tested genes in the current sample set (inter-patient analysis). The 3 most predictive genes were GSTA4, PGR and EFNB2 and resulted in a similar accuracy as the previous model with EFNB2, CAMK1D and STC1 (73% versus 72%). Using three genes, none of the patient or cycle characteristics could improve the model, suggesting that the expression of the three genes was minimally influenced by patient and cycle factors. The live birth model could be improved by including two more genes (GPX3 and GSTA3), which increased the accuracy up to 81% and resulted in an AUC of 0.93. This 5 gene model was improved with three patient and cycle characteristics (age, relative E2 and days of stimulation) and resulted in an optimized model with a PPV. NPV and accuracy of 93%, but similar AUC as the model only containing genes. Ideally, pregnancy prediction based on gene expression should be possible with a limited set of genes to reduce analysis time and cost. Of the 12 genes tested in this patient population, the 2 most recurrent genes are GSTA4 and EFNB2 (see Table 5). These 2 genes are present in all 3 pregnancy models and have respectively in 3 out of 3 and in 2 out of 3 predictive models a type-III P-value <0.01. The models also showed that the gene expression values are always more important than the patient and cycle characteristics, as the type-Ill P-values in the models are only significant for the genes and not for the patient and cycle characteristics. Furthermore, the AUC results are comparable between the model containing only genes and the model combining genes and patient and cycle characteristics.

For 7 patients, 2 (or 3) CC from oocytes giving embryos with a good morphology and consecutively transferred, were analyzed (Intra-patient analysis). For all oocytes, pregnancy outcome was known as all embryo transfers were done in subsequent SET cycles. Having assessed the expression of 7 genes (EFNB2, CAMK1D, GSR, PGR, GSTA4, GSTA3 and GPX3), it was easy to estimate, based on single genes or on a combination of them in a model, which oocyte of the two considered ones would have the highest chance to pregnancy. The best predictions, when looking at each gene individually, were found for CAMK1D, GSR, EFNB2, PGR and GSTA4 with 71% to 86% correct estimations. Combining 3 or 5 genes, according to the earlier models, 6 of the 7 patients had the cumulus complexes correctly predicting the chance to pregnancy. This prediction was the same when using the 3 or 5 gene model. Surprisingly, the multiparametric model failed on a different patient than the single gene analysis. The multiparametric approach seems stronger than the individual genes as all genes wrongly predicted the pregnancy outcome for the second comparison of patient 6, but the multiparametric model predicted successfully, especially as the CC of the oocytes that resulted in pregnancy were not considered for building the predictive model. The failed prediction of the multiparametric approach for patient 4, where the individual genes were correct in 4 out of 5, could be due to other factors (e.g. the endometrium status at the moment of transfer). Although this analysis is still limited in patient numbers, these results are encouraging. This is the first study that confirms that some genes predicting pregnancy between patients might also be capable of ranking the quality of oocytes within patients using a multiparametric approach and providing a chance to pregnancy for each oocyte. CC gene expression analysis might become a valuable tool in the ART lab but does obviously not take into account the eventual influence of poor sperm quality and out-of-phase endometrium.

This study could confirm the use of earlier found predictive genes in a new patient population, with the same stimulation protocol, but with different culture media. This data suggests that EFNB2 and CAMK1D, the only genes that we analyzed in two studies using two different culture media, were not affected by culture media. To test the validity of the current models, a future analyze should involve patients with different stimulation protocols and different culture media. Reasons why the specific genes of this study are important for pregnancy prediction remains speculative. As mentioned previously (Wathlet et al. 2012), CAMK1D may, among other pathways, be related to steroidogenesis by its strong correlation with steroid related genes (CYP11A1, STC2 and HSD3B1). In this data set CAMK1D also strongly correlated with a steroid related gene i.e. PGR next to EFNB2 and GSTA4 (all P<0.0001 with Pearson correlation analysis) still leaving the possibilities open for more than one pathway to which CAMK1D could be associated with. The presence of PGR in the pregnancy models and its predictive power within patients might indicate that steroid-related genes could be helpful in pregnancy prediction. PGR has been described before, but no difference between pregnant and non-pregnant could be confirmed with quantitative PCR (Hamel et al. 2010b). GSTA3 that was present in some of the pregnancy models also has a link with progesterone production (Raffalli-Mathieu et al. 2008) reiterating the importance of the steroidogenesis pathway. The function of EFNB2 in the ovary is not yet known, but B-class ephrins were proposed to be related to the luteinization process (Egawa et al. 2003) and the ephrin B2 receptor was found differently expressed between CC from normal oocytes compared to aneuploid oocytes (Fragouli et al. 2012b). Out of the other genes tested, only members of the glutathione family were retained in the models or were significant in the t-test. Glutathione enzymes are important for detoxification actions (of free radicals) in the cells through the use of glutathione. Hypoxia leads to the formation of reactive oxygen species (ROS) which can cause lipid peroxidation, enzyme inactivation and cell damage, resulting in apoptosis (Buttke and Sandstrom 1994) not only in CC, but also in the oocyte (Tatemoto et al. 2000). Oxidative stress has already been reported by other groups as a possible target to assess oocyte quality (Lee et al. 2010; van Montfoort et al. 2008). One reason that some transcripts of those pathways are higher in the CC from oocytes giving pregnancy might be that those oocytes are better protected against a stressful environment if needed.

CONCLUSION

By testing presumably important genes batch wise in three consecutive studies on different patient groups for which cumulus complexes were frozen individually per oocyte, we retained the most predictive genes for pregnancy and opposed these every time to new candidate genes. This 'cascade' strategy attempted to increase the power of pregnancy prediction using CC gene expression as quality marker for oocytes in ART. The strategy proved effective as the model with EFNB2, CAMK1D and STC1 from the second study (Wathlet et al. 2012) could be confirmed on an independent patient sample set. In an attempt to further improve prediction models for live birth, models were built (inter-patient analysis), still retaining EFNB2 together with PGR and genes related to the glutathione metabolism. The new models proved to be able to rank oocyte for their potential for pregnancy (Intra-patient analysis). The validity of our current models, for routine application, still need prospective assessment in a larger and more diverse patient population allowing Intra-patient analysis.

Example 2

Exon Level Analysis

Three micro array experiments were performed and their resulting data led to 4 micro array analyses. Below respectively named micro array analysis 1, 2, 3 or 4 (see table 14 below). Array experiment 1 and 2 were used for data-mining, (for finding genes or exons of genes that are predictive for oocyte competence) and array experiment 3 was used for filtering the recurrent predictive genes (finding genes or exons that are more general applicable as they are predictive in different fertility centers and after slightly different treatments). The most novel analysis is based on micro array experiment 2 which comprises an intra patient and intra-cycle (oocytes from the same stimulation cohort) analysis for live birth.

Material:

For the three micro array experiments cumulus cells were collected as described before (Wathlet et al. 2011). The RNA was extracted using the Qiagen Rneasy micro kit as described in Wathlet et al. 2011. The quality and quantity of the RNA was verified using the Bioanalyzer (Agilent) and the Nanodrop (Thermo Scientific).

For the micro arrays in the first set amplification was performed by starting from 100 ng total-RNA and a 1 round T7 based amplification (Message Amp II-Biotin Enhanced, Ambion). Good Quality aRNA (size distribution, 3'/5' ratio & % present calls) was verified and Affymetrix Human Genome U133 Plus 2.0 Arrays were performed at the Salk Institute (USA, San Diego). Further analysis of the gene readouts was performed using Genesifter (Perkin Elmer). For Array experiment 2 and 3 RNA was extracted, measured, and evaluated as mentioned above but amplification was performed using the Nugen V2 kit. Arrays were, both for array experiment 2 and 3, the Affymetrix Human Gene ST arrays. Data were mainly analyzed in Microsoft Excel.

Method:

Intra-patient comparison comprises that both the positive sample (CC of an oocyte resulting in a pregnancy in a single embryo transfer) and the negative sample (CC of an oocyte resulting in no pregnancy after single embryo transfer) originate from the same patient and the same stimulation and pick up cycle.

Comparison or analysis was performed one parametric with regular or paired t-test and multiparametric using stepwise multiregression analysis. The multiparametric approach resulted in gene or exon combinations which increases the predictive power.

Aim:

Find genes or splice variants of genes (exons) predictive for live birth after ART treatment. This is done in an intra-patient comparison, Set Up and First Results (Array Analysis 1 and 2):

Array experiment 1, performed in 2006, comprised an inter patient comparison for live birth and an intra-patient comparison for embryo development. Patient pretreatment was GnRH Agonist combined with HP-hMG. This resulted in 2 quality lists: comprising over 500 genes, ("Q1"=genes predictive for successful oocyte and embryo development. "Q3"=genes predictive for live birth)

Array analysis 2 was performed in January 2012 and consisted of an intra-patient analysis for live birth and delayed development for 5 patients and 15 arrays and resulted in several lists with differentially regulated genes. Patients were in this case pretreated with GnRH Antagonist and recombinant FSH.

Array experiment 3 was only used as a confirmation dataset in micro array analysis 4 and is further described below.

TABLE 14

| Micro Array experiments by FOBI | | | | | |
|---|---|---|---|---|---|
| Analysis | Time | Setting | Patient prétreatment | Parameters | Outcome |
| 1 | 2006 | intra- and inter-patient comp. | GnRH Agonist + HP-hMG | no development ≍ Live birth ≍ No Pregn. | Q1 and Q3 |
| 2 | January 2012 | intra-patient comparison | GnRH Antagonist + rFSH | deleayed development ≍ Live birth ≍ No Pregn. | 1,246 list, . . . |
| 3 | August 2012 | inter-patient comparison | GnRH Antagonist + rFSH and HP-hMG | Live birth ≍ No Pregnancy | |
| 4 | December 2012 | reanalysis of exp. 2 + 3 on exon level | GnRH Antagonist + rFSH and HP-hMG | deleayed development ≍ Live birth ≍ No Pregn. | 35 and 11 gene list |

Array analysis 4: Reanalysis of the micro array data of array experiment 2+3 on an exon level In searching for genes expressed in the cumulus cells predictive for pregnancy we surprisingly found, that for some genes, specific combinations of splice variants for these genes were predictive. This finding is not obvious with the 2 most standard analysis methods, micro arrays and Q RT-PCR, currently available in the lab, as is explained below.

In this field of research the most commonly applied micro array analysis (Affymetrix Human Genome U133 Plus 2 and Affymetrix Human Gene ST arrays) evaluate/consider one generalized (average) expression value obtained per gene, based on 4 or more probes recognizing some part of the coding and non coding RNA related to a specific gene. This number reflects the abundance or absence of a bulk of RNA molecules related to a specific gene but gives no information on the regulation of specific splice variants.

The alternative "standard" analysis technique, quantitative PCR after reversed transcription (RT-QPCR), on the other hand normally only analyzes the abundance of 1 exon, which corresponds for most of the genes to evaluating only a specific fraction of the splice variants of this specific gene.

Specifically investigating more than 1 splice variant is relevant as specific splice variants could be coding for tissue specific (e.g. cumulus cell specific) or secreted or more active forms of the protein. Alternative splice variants (often shorter forms) can also have a regulatory function and actually down-regulate the amount or the effect of the protein. Therefore combining the information of different splice variants for a specific gene holds more information but requires also more time and resources to investigate and is not commonly done.

Notwithstanding, in the present study we reanalysed the foregoing array experiments on an exon level. In this experiment genes predictive for successful fertilization, embryo development and implantation on an exon level were selected in array experiment 2 as described below.

The Samples:

Fifteen Affymetrix micro arrays were performed on 15 cumulus samples from five ICSI patients. CC originated from oocytes that resulted in 3 outcome categories: 1. an embryo with a high morphological score (Embryo quality 1) that was transferred and resulted in a pregnancy (P-CC) 2. an embryo with a high morphological score (Embryo quality 1) that was transferred but did not result in a pregnancy (NP-CC) and 3. an embryo that developed too slow to be considered for transfer (NT-CC).

The patients considered for this study were stimulated with GnRH antagonist and rFSH and were not pregnant from the first single embryo transfer and came back for the transfer of a single frozen embryo which did result in a pregnancy. As such the CC samples from category 1, 2 or 3 originated from 1 pick up cycle and this thus allowed an intra patient analysis.

The Analysis:

This analysis was performed on an exon level. Four comparisons were performed, 3 times an ANOVA comparing the 3 conditions, 1 time 2 t-tests were performed comparing the best condition, the P-CC to the NP-CC and P-CC to the NT-CC. The variable patient was considered as a random variable in the t-test comparison, and was once random and once fixed in the ANOVA analysis on 5 patients and was considered as random in the ANOVA comparison of 3 of the 5 patients (considering only the patients that got transfer on day 5 and not the 2 patients that got transfer on day 3).

Genes were considered potentially interesting if they were: a) differentially expressed between P-CC and both NP-CC and NT-CC, b) in the same direction different (e.g. down in the 2 negative control samples), c) at least one of the difference was >1.5 with a q<0.1 (False discovery rate) and d) more than one exon of that gene was retained.

The Results:

This resulted in a 34 gene list that was the subject of this patent application. These were than supplemented with the up till now eleven strongest genes from the earlier lists (Q1+2+1.246—table 14 above) which results in the 45 list (Table 13). These were on an exon level filtered in the array experiment 3 using stepwise multiple regression analysis. In brief, in array experiment 3, 112 micro arrays were available from individual CC of 112 patients that were pregnant or not after a single embryo transfer cycle (SET-cycle). All exon values from the table 13 genes in these 112 patients were considered for prediction model building using stepwise multiple regression analysis. This was done in multiple rounds to compensate for too high numbers of variables and was performed using cross-validation to prevent over fitting. This led to the most powerful combinations of genes to be retained, which gave rise to the "11 gene list" (SASH1, MROH9, NCOA7, DNAH3, HSPH1 exon 2, HSPH1exon 6, GALNTL6, SPTBN5, CAMK1D exon 1, CAMK1D exon 9, EFNB2). (Table 8)

The "11 genes list" consists of the most predictive exon level genes combinations and are therefore the core of the current application. The original "45 gene list" contains other genes that are related to them and could eventually replace one or more of the 11 genes if needed. An example of this is given below and discussed in more detail in Table 11. In brief an strong oocyte competence prediction model for GnRH antagonist and rFSH stimulated patients was found to contain CAMK1D exon 9, HSPH1 exon 2 and NCOA7 (Accuracy=73% ROC-AUC=-0.733) but for the same patients a model with CAMK1D exon 9, HSPH1 exon 6 and NCOA7 was also prediction oocyte competence, even if it was slightly less powerful, (Accuracy=68% ROC-AUC=0.714).

TABLE 8

| Gene | Exon | Ref Sequence: Region | SEQ ID No |
|---|---|---|---|
| SASH1 | Exon 12 | NT_025741.15: 53010140-53010486 | 19 |
| NCOA7 | Exon1 | NT_025741.15: 30271764-30271974 | 20 |
| NCOA7 | Exon 2 | NT_025741.15: 30276740-30276816 | 21 |
| CAMK1D | Exon 1 | NT_008705.16: 12331541-12331909 | 22 |
| CAMK1D | Exon 9 | NT_008705.16: 12798249-12798327 | 23 |
| SPTBN5 | Exon 8 | NT_010194.17: 12966103-12966241 | 24 |
| MROH9 | Exon 14 | NT_004487.19: 22454290-22454427 | 25 |
| HSPH1 | Exon 2 | NT_024524.14: 12715613-12716117 | 26 |
| HSPH1 | Exon 6 | NT_024524.14: 12705084-12707088 | 27 |
| DNAH3 | Exon 21 | NT_010393.16: 21057811-21057995 | 28 |
| GALNTL6 | Exon 16 | NT_016354.19: 98420909-98421130 | 29 |
| EFNB2 | — | at gene level | |

NCOA7* also at gene level.
Either of the exons can be used.

Conclusions:

Several gene and specific exons of genes have been successfully related to live birth and embryo development in array experiments comprising patients undergoing different pretreatments and these were also confirmed in an independent array dataset (array experiment 3). The strength of the 3$^{the}$ array experiment lays in the fact that it was performed on samples from three different European sites. As such the final subset of genes retained should be more universally applicable, than any known gene combination up till now. To test this, two confirmation experiments were performed departing from this subset of 11 genes, to demonstrate the ability of the foregoing genes in predicting oocyte competence. The first confirmation experiment has been a retrospective study, including an intra- and inter-patient analysis and the second study has been a prospective study in 3 groups of patients.

Example 3

Retrospective Study

The retrospective study was performed with samples collected from 107 patients in two clinical sites. The QPCR was performed exon specific for 7 oocyte quality markers, from the 11 gene list (HSPH1 exon 2, HSPH1 exon 6, CAMK1D exon 1, CAMK1D exon 9, EFNB2, NCOA7, SASH1) and 2 endogenous controls (UBC and B2M) in three different batches (Table 9).

TABLE 9

The samples available for the proof of concept studies.. B1/2/3 = batch 1/2/3, site 1 + 2 = European and American fertility center, patient pretreatment = GnRH antagonist combined with rFSH or HP-hMG and the outcome pregnant = at least 2 weeks after transfer pregnant, not-Preg. = not pregnant after transfer, delayed = embryo developing slow and not considered for transfer

| Sample set | inter patient analysis | | | | intra-patient |
|---|---|---|---|---|---|
| | B1 | B2 | B3A | B3B | B1 + 2 + 3 |
| Site | 1 | 1 | 1 | 2 | 1 + 2 |
| # Patients | 60 | 26 | 14 | 7 | 11 |
| Anta + rFSH | x | x | x | x | x |
| Anta + HP-hMG | | x | x | x | |
| Pregn | 37 | 15 | 15 | 14 | 8 |
| Not-Preg. | 27 | 17 | 8 | 9 | 7 |
| Delayed | 34 | 12 | 4 | 14 | 8 |
| Total | 98 | 44 | 27 | 37 | 23 |

Cumulus Cell Collection:

The cumulus cell samples were collected in one European and one American Fertility Centre (Table 9) and originate from patients that got one embryo per transfer (SET=Single Embryo Transfer) and proved to be pregnant or not. This allowed the retrospective comparison of CC of competent and less competent oocytes. This is the most obvious approach but oocytes originate from different patients (=inter-patient analysis) and this results in some inter-patient variance that is not controlled for. There was also a subset of patients that got 2 or more consecutive single embryo transfers from a single oocyte harvest procedure (pick up), that resulted in a pregnancy or not and thus allowed also in the retrospective study an intra-patient comparison of the CC.

Three types of cumulus cell samples have been collected: samples from oocytes of which the embryo was transferred and led to a pregnancy, samples from good quality embryos that were transferred but did not result in a pregnancy, and cumulus samples from delayed embryos. Delayed embryos are embryos that are developing slower, which is considered indicative for poor oocyte competence, and these embryos are therefore not considered for transfer. The cumulus cells from delayed embryos were used as an intra-patient, negative control for those patients who had an oocyte giving a pregnancy. The distinction between the CC of morphologic identical embryos resulting in a pregnant and not (later referred to pregnant versus not pregnant) is considered more important than the distinction between the CC of oocytes leading to a pregnancy or to an embryo delayed during in vitro development (later also referred to as "pregnant versus delayed embryo development") as the latter information is already available to labs performing extended embryo culture.

All patients underwent ovarian stimulation with GnRH antagonist and rFSH or HP-hMG and were initially analyzed per treatment group.

Statistics:

During the statistical analysis, first a one-parametric approach was used with Student t-tests (paired and unpaired). Secondly, a cross-validated multi-parametric model was built with the use of stepwise multiple regression analysis for a binary response.

Results 1: Intra-Patient Analysis a) one parametric: Pregnant versus delayed embryo development In the one-parametric analysis (paired t-test) between CC of oocytes resulting in a pregnancy or a delayed embryo growth (n=8), we studied 7 genes and found a consistent upregulation in 4 of the 7 genes (Table 10). CAMK1D exon 1 and NCOA7 were upregulated in 88% of the cases, while CAMK1D exon 9 and SASH1 were upregulated in 75% of the patients. However, no significant differences were reached (paired t-test p-values ranged from 0.14 to 0.24), because of the large inter-patient variance.

b) One parametric: Pregnant versus not pregnant

In the comparison between the CC of oocytes resulting in a pregnancy or not of the same patient (n=7), 3 of the 7 genes that were studied, showed a consistent upregulation in 71 to 86% of the patients: EFNB2, CAMK1D exon 1, and CAMK1D exon 9. Significance was reached with CAMK1D exon 1 (p 0.021). One gene, HSPH1 exon 6 showed a consistent downregulation in 71% of the patients.

This first intra-patient analysis thus confirms an upregulation of a known oocyte quality marker gene, CAMK1D, in the CC of oocytes resulting in a pregnancy compared to the CC of oocytes that will result in good morphology embryos that do not lead to a pregnancy or to delayed embryos of the same patient. These results also confirm the relevance of three new genes: NCOA7, SASH1 and HSPH1.

TABLE 10

| | | | Pregnant >< Delayed | | | | Pregnant >< Not Pregnant | |
|---|---|---|---|---|---|---|---|---|
| n | gene | #ok | in pregnant | p value | n | gene | #ok | in pregnant | p value |
| 8 | HSPH1 ex2 | 50% | | | 7 | HSPH1 ex2 | 57% | | |
| 8 | HSPH1 ex6 | 63% | down | 0.22 | 7 | HSPH1 ex6 | 71% | down | 0.45 |
| 8 | EFNB2 | 50% | | | 7 | EFNB2 | 71% | up | 0.14 |
| 8 | CAMK1D ex1 | 88% | up | 0.17 | 7 | CAMK1D ex1 | 86% | up | 0.021 |
| 8 | CAMK1D ex 9 | 75% | up | 0.14 | 7 | CAMK1D ex 9 | 71% | up | 0.27 |
| 8 | NCOA7 | 88% | up | 0.24 | 7 | NCOA7 | 57% | up | |
| 8 | SASH1 | 75% | up | 0.27 | 7 | SASH1 | 43% | up | 0.31 | n = number of patients, #ok = % of patients having an up or down-regulation, in pregnant = in pregn. patients the gene is up or downreglated Earlier results in a similar setting indicated that a multi-parametric approach increases the number of correctly predicted samples (Wathlet et al., 2013). Therefore, we also performed a multiparametric intra-patient analysis on the same samples.

c) Multiparametric: Pregnant versus delayed embryo development or not pregnant

The more sophisticated multiparametric analysis resulted in a strong pregnancy predictive model with EFNB2 and NCOA7, showing an accuracy of 73% and an ROC-AUC of 0.772. More detailed results are provided below (Table 11 and FIG. 5). This further confirmed the predictive quality of known and novel CC genes as oocyte quality markers.

Results 2: Inter-Patient Analysis

To increase the sample size inter-patient analyses were also performed on samples from 2 sites. This extra analysis should provide more generally applicable models.

While the same genes are predictive for oocyte competence in the patients stimulated with GnRH antagonist and rFSH or HP-hMG, the relation is for some genes inverse (e.g. CAMK1D in FIGS. 6 and 7). For the ease of interpretation, pretreatment specific models were built and described here. These will later be combined into one mathematical model with treatment specific indices (earlier applied in Adriaenssens et al. 2010).

a) GnRH antagonist and rFSH stimulated patients, pregnant versus delayed embryo development The intra-patient analysis indicated that four of the seven genes analyzed here could be used to distinguish the CC of an oocyte leading to a pregnancy or to an embryo delayed in development.

In the current GnRH antagonist and rFSH stimulated patients the inter-patient variance seems however to prevent the construction of a strong mathematical model. The addition of an extra gene of the 45 list could circumvent this.

b) GnRH antagonist and rFSH stimulated patients, pregnant versus not pregnant

For the GnRH antagonist and rFSH stimulated patients in batch 1, 2 and 3 (n=34 pregnant and 29 non-pregnant patients), a strong oocyte quality predictive model containing 3 genes was obtained. Two genes, CAMK1D exon 9 and HSPH1 exon 2, were positively correlated with pregnancy and NCOA7 was negatively correlated. More detailed results are provided below (Table 11 and FIG. 6). The accuracy of this model was 73% and AUC of 0.733. This model is currently used in the prospective study for GnRH antagonist and rFSH stimulated patients.

c) GnRH antagonist and HP-hMG stimulated patients, pregnant versus delayed embryo development It was found that the multi-parametric model for antagonist HP-hMG patients distinguishing the CC of oocytes leading to a pregnancy from the CC of oocytes leading to an embryo with a delayed development (n=20), had a high accuracy (80%) and AUC (0.8081). SASH1 was positively correlated with pregnancy, and CAMK1D exon 1 was negatively correlated with pregnancy. More detailed results are provided below (Table 11 and FIG. 7). SASH1 expression was also correlated with CAMK1D exon 9, NCOA7 expression. CAMK1D exon 1 expression was correlated with CAMK1D exon 9 expression.

d) GnRH antagonist and HP-hMG stimulated patients, pregnant versus not pregnant

The pregnant versus non-pregnant multi-parametric model in GnRH agonist and HP-HMG patients (n=24) was also strong (Accuracy=75% and AUC=0.8392) and was also largely depending on the positive relation of SASH1 expression with oocyte developmental competence (detailed figure not shown).

TABLE 11

Schematic overview of the gene models (exon level where relevant) and their predictive value in the different subpopulations in the retrospective QPCR study

| | Patient pretreatment | Antagonist rFSH | Antagonist rFSH | Antagonist* rFSH | Antagonist HP-hMG | Antagonist HP-hMG |
|---|---|---|---|---|---|---|
| | Analysis | intra- patient | inter-patient | inter-patient | inter-patient | inter-patient |
| | Endpoints | Pregn.><NotPregn. | Pregn.><NotPregn. | Pregn.><NotPregn. | Pregn.><Delayed | Pregn.><NotPregn. |
| Genes | EFNB2 | x | | | | x |
| in the | CAMK1D exon 1 | | | | x | |
| model | CAMK1D exon 9 | | x | x | | |
| | HSPH1 exon 2 | | x | | | |
| | HSPH1 exon 6 | | | x | | |
| | NCOA7 | x | x | x | | |
| | SASH1 | | | | x | x |
| | p-value of the model | 0.0127 | 0.0159 | 0.0322 | 0.1988 | 0.0083 |

TABLE 11-continued

Schematic overview of the gene models (exon level where relevant) and their predictive value in the different subpopulations in the retrospective QPCR study

| | Correlated genes* | CAMK1D exon 9 HSPH1 exon 6 | CAMK1D exon 1 | CAMK1D exon 9 NCOA7 | CAMK1D exon 1 |
|---|---|---|---|---|---|
| Per- | PPV | 86 | 72 | 68 | 82 | 69 |
| for- | NPV | 63 | 75 | 68 | 78 | 81 |
| mance | Sensitivity | 63 | 82 | 77 | 82 | 82 |
| of the | Specificity | 86 | 62 | 59 | 78 | 69 |
| model | Accuracy | 73 | 73 | 68 | 80 | 75 |
| | AUC | 0.7726 | 0.7333 | 0.714 | 0.8081 | 0.8392 |

*Correlated genes are genes that showed a strong correlation to the genes in the model and that were therefore not selected by the multiple regression analysis. Some of these also have a strong predictive power and could be used as "additional" genes in testing. This is demonstrated by the alternative antagonist/rFSH inter-patient pregnant to not pregnant model with HSPH1 exon 2 being replaced by HSPH1 exon 6

Conclusions of the Retrospective Study:

CAMK1D exon 9 and EFNB2, both chosen as positive control genes are in the current dataset confirmed both in the intra- and inter-patient analysis.

The relation between oocyte competence and expression of patentable genes was also confirmed by their implication in predictive models after different types of ART pretreatment. HSPH1 exon 2 and NCOA7 are retained in the final model for antagonist/rFSH stimulated patients. SASH1 is a powerful predictive gene for antagonist/HP-hMG stimulated patients. The fact that HSPH1exon 6 and EFNB2 are not retained in the final model does not imply that these markers are not related to oocyte competence; as they are correlated with other markers (HSPH1 exon 6 is correlated with HSPH1 exon 2, and EFNB2 is correlated with CAMK1D expression) and hence are rejected from the regression analysis.

Example 4

Prospective Study

A case-control assessor blinded prospective study was performed by FOBI using 2 of the oocyte competence predictive models described higher (FIGS. 6 and 7). The study comprised 3 groups of patients: the experimental group with morphological embryo grading (as described in Wathlet et al 2012) and CC gene analysis and transfer of a day 3 embryo and the 2 control groups with morphological embryo grading alone and transfer of a day 3 or a day 5 embryo. The 2 controls are included as pregnancy rates differ between the two transfer regimes. Day 5 transfer slightly increases clinical pregnancy rates in the first cycle but cumulative pregnancy rates are higher in in day 3 transfer cycles (Glujovsky et al. Cochrane review 2012).

The Aim:

The aim was to identify within the pool of oocytes obtained from each patient the oocyte with the highest competence by comparing the expression of specific genes in the CC that surrounded each oocyte. The embryo originating from this oocyte was transferred back to the patient. The CC gene expression analysis combined with morpghological grading is expected to increase the chance on pregnancy for these patients compared to matched patients without the CC evaluation (i.e. choice of embryo to transfer only decided on routine morphological embryo grading).

Patient Population and Genes Analyzed:

This study comprised 17 patients. The patients included are patients from the ART clinic scheduled for fertility treatment with intra-cytoplasmatic sperm injection (ICSI) and single embryo transfer after 3 days of embryo culture (generally an 8 cell stage embryo). Patient pretreatments allowed are GnRH antagonist plus rFSH or HP-hMG and the gene expression models described in FIGS. 5 and 6 are used for these patients respectively.

The genes analyzed (CAMK1D exon 9. CAMK1D exon 1, HSPH1 exon 2, NCOA7. SASH1) originated from the 11 and 45 gene list submitted in this patent application.

The Different Steps in the Procedure:

This study comprised the following steps:

1. Patients were informed and included when they signed informed consent.
2. Oocytes were collected from these patients as usual
3. Oocytes were individually freed from their cumulus cells using cumulase as usual
4. Cumulus cells were processed or frozen immediately
5. The oocytes were further used for the infertility treatment (in the current study: ICSI and embryo culture)*
6. The expression of specific genes in the cumulus cells was assessed
7. The obtained CC score potentially indicated the most competent oocyte (with the highest chance on live birth) and was used to select the most promising embryo between the embryos with the best morphological grade available for each patient
8. This single embryo was transferred back to the patient**
9. For each patient that got an embryo transfer based on the CC gene expression, a matching patient (same age category, similar pretreatment and having the same amount of good quality embryos available for transfer) with embryo transfer on day 3 (generally an 8 cell embryo) and day 5 (generally an expanded blastocyst) without CC gene expression analysis was selected in an assessor blinded manner.
10. For the 3 groups of patients (the experimental group and the 2 control groups) the implantation and pregnancy rates are evaluated.

Remarks: * this step could comprise oocyte freezing for later use, eventually in specific media supplemented with nutrients to compensate for the deficiency that was observed in the CC gene expression result.

** the CC score could be used independently or combined with morphologic or other oocyte, sperm or embryo evaluation methods The Cumulus Cell Gene Expression Evaluation:

The expression of specific genes was quantified in the CC of each oocyte. The absolute expression of each gene was normalized to the expression of 2 endogenous genes in the same CC sample to compensate for cell number differences and technical variance between the samples. The normalized expression values were than used in the mathematical formula described in FIGS. 6 and 7 and result in a score for each oocyte. The higher this score, the higher the chance that this oocyte would result in a live birth.

Results: Pregnancy Rates when Using CC Gene Expression Based Oocyte Evaluation

From the 17 patients 8 had a GnRH antagonist rFSH and 9 had a GnRH antagonist HP-hMG pretreatment. A beneficial effect of the CC evaluation is apparent for the day 3 transfer regimes (FIG. 7). The chance on a pregnancy was 2× higher for the patients with a day 3 embryo transfer and CC-Test compared to those patients with a day 3 embryo transfer without CC-Test. The number of patients is currently too limited to confirm the significance of an increase when compared to the patients with a day 5 embryo transfer.

TABLE 12

Interim results in the prospective study

| Patient pretreatment | Experimental group | Transfer Day | Total # | pregnant # | not pregnant # | Chance on preg. % | Significance |
|---|---|---|---|---|---|---|---|
| 2 Treatments Combined | CC-Test | 3 | 17 | 9 | 8 | 53 | |
| | Control (No CC-Test) | 3 | 17 | 4 | 13 | 24 | p < 0.05 |
| | | 5 | 17 | 8 | 9 | 47 | ns |

Gray = the 17 patients in the experimental arm, white = the 2 control groups, Significance = based on the Chi-square test comparing the experimental group with each of the control groups, ns = p > 0.05, pregnant = at least 2 weeks pregnant (2 consecutive positive hCG detections).

Conclusions of the Prospective Study:

Implementing the CC-Test analysis in the clinic as described above significantly increased the chance on a pregnancy for the patients involved in the study and thus proves the relevance of the genes which are the subject of the current patent application.

The models used in this proof of principle experiment contained 2 and 3 genes. From earlier micro array experiments (with more genes and more patients analyzed) we know that adding more genes (up to at least 5 or 6) will further improve the predictive power of the models. This work is currently ongoing with more genes from the list in the current patent.

General Conclusion:

The 45 oocyte quality marker gene list originates from 2 array experiments using UZBrussel patients and was cross validated using data from a 3th independent array experiment containing more than 100 patients from 3 different European fertility centers. This approach should provide solid marker genes and gene combinations/models to predict treatment outcome.

As a proof of concept a subset of 7 genes, containing 4 novel genes, was tested using an alternative technique (QPCR) on CC samples from new patients collected at 2 fertility centers. The 4 genes were confirmed as valuable oocyte quality marker. This confirms that the proposed gene list contains valid oocyte quality predictive genes.

Finally the gene models were tested in a prospective study where pregnancy rates were increased in the patients where embryos were selected based on the expression of the above described oocyte quality marker genes in the CC.

The latter study was performed in patients of the ART clinic undergoing standard treatment by ICSI and thus confirms the applicability of the oocyte quality markers in a clinical setting.

Example 5

Retrospective Evaluation of Alternative Models for Pregnancy Prediction

Aim: Identify alternative genes and gene models predictive for the 'chance on pregnancy' using a cumulus analysis in ART patients. Here we additionally considered the variability of the assays to obtain a model with genes that are (or might be) less prone to technical variance.

Material and Methods

Setting: retrospective non interventional clinical study

Material: cumulus cells of patients undergoing ICSI with SET in an ART clinic after a stimulation with HP-hMG.

N=number of CC samples=59 coming from 86 patients.

Method: QPCR analysis for specific mRNA molecules in the CC and stepwise linear regression based model building in relation to the oocytes/embryos competence (clinical pregnancy). The genes tested were EFNB2, CAMK1D exon 1, CAMK1D exon 9. HSPH1 exon 2, HSPH1 exon 6, NCOA7 and SASH1. This was a weighted regression taking into account the variability detected in the QPCR analysis.

Results:

A strong model predictive for pregnancy in human ART patients was found.

This model had a p value of 0.0153 and comprised the mRNA expression of HSPH1 exon 6, CAMK1D exon 9 and HSPH1 exon 2, had an accuracy of 77% (PPV=74% and NPV=81%) and an AUC value in the ROC-analysis of 0.7814.

Conclusion:

This is a new clinical study confirming the predictive power of CC-analysis for oocyte competence prediction. Additional genes from the initial 45-list (obtained mainly from micro array experiments) prove to be informative too (HSPH1 exon 2, HSPH1 exon 6) in a QPCR experiment.

Example 6

Retrospective Evaluation of the Predictive Power of Using the Measurement of SASH1 Alone for Pregnancy Prediction Aim: Study whether a CC-Test with SASH1 alone is predictive for the 'chance on pregnancy' in ART patients.

Material and Methods

Setting: retrospective non-interventional clinical study

Material: cumulus cells of patients undergoing ICSI with SET in an ART clinic after stimulation with HP-hMG N=number of CC samples=59 coming from 86 patients.

Method: QPCR analysis for SASH1 mRNA in the CC and the statistical comparison of the expression levels observed in CC in relation to the oocyte competence.

Results:

As evident from FIG. 8, SASH1 alone proved to be predictive for pregnancy with a p=0.0133. The positive predictive value was 74% and the overall accuracy of the prediction is 68%.

Conclusion:

This example proves that SASH1 alone can already predict pregnancy. Nevertheless, combining it with 1 or more genes might make the prediction stronger. This was already proven in earlier developed models using other genes from the 45 list.

Example 7

Finding a Predictive Model for Oocyte Competence in rFSH Stimulated Patients

Aim: Confirm the predictive power of genes expressed in human CC in relation to the oocyte/embryo competence of ART patients stimulated with rFSH with the intention of using it as a diagnostic test for ART-patients in order to increase their chance on pregnancy.

Material and Methods

Setting: retrospective non interventional clinical study.

Material: cumulus cells of patients undergoing ICSI with SET in an ART clinic after a stimulation with rFSH.

N=number of CC samples=69 coming from 45 patients. Of these 69 samples 45 CC samples originate from a oocytes used in a fresh transfer (n=24 resulting in a clinical pregnancy and 21 not resulting in a pregnancy). The remaining 24 samples originate from oocytes/embryos transferred in a consecutive "natural" cycle (n=11 resulting in a clinical pregnancy and 13 not resulting in a pregnancy).

Method: QPCR analysis for specific mRNA molecules in the CC. The expression levels of the specific genes was compared in a one parametric analysis using a t-test in relation to the oocytes/embryos for competence (clinical pregnancy). The genes investigated originate from the 45-list and consisted out of following candidate genes ALDH1L2, ASNS, GOT1, NPR1, SLC6A9, SLIT2.

Results:

While no significant differences were found when comparing the CC expression of the fresh transferred patients (n=45 CC), significantly higher expression levels of ALDH1L2, ASNS and GOT1 were found in the patients undergoing a transfer in a consecutive natural (i.e. unstimulated) menstrual cycle (n=24 CC). This is a surprising finding. The second group of CC (n=24) with transfer done in the consecutive natural cycle) was added only to increase the number of data. The separate analysis of these CC was not part of the original aim. Average fold changes of expression between good and bad outcome range from 2 tot 3 fold. (see FIGS. 9A-9C)

While SLC6A9. NPR1 and SLIT2 expression was also increased in the CC of oocyte with a chance on pregnancy, this did not yet reach statistical significance in the current dataset.

Conclusion:

This new clinical study confirms the predictive power of CC-analysis for oocyte competence prediction. This time evidence is obtained in a stimulation treatment using rFSH.

The 6 "new" genes originate from the initial 45-list. The potentially compromised receptivity of the endometrium of the patients undergoing a fresh transfer might result in false negative results in the analysis of the 45 sample group and seems to prevent the confirmation in the fresh transfer group.

In the monitored natural or programmed natural cycles, the endometrium is known to be better. In this model the oocytes with a 'favorable' gene expression profile will implant more often.

Next to the one parametric analysis mentioned above. Model building has been performed as well. The first findings here confirm the relevance of the genes and results. A strong pregnancy prediction model, comprising 2 from the 6 genes mentioned above, could be obtained. This model had a prediction Accuracy=83% and an ROC curve AUC=0.8601). Next to this also an embryo development prediction model was found. This 3 gene model had a prediction Accuracy=71% and a Roc curve AUC 0.7691. This model based on CC expression only predicts (at the day of pick up or 1 day later after the CC analysis) whether the patient will have an embryo of a good enough quality to ascertain a transfer and from which oocytes the transferable embryo is originating.

Example 8

Gene Model for FRET (Frozen Embryo Transfer)

Material and Methods

Sample set of 45 patients from cDNA material used for CC-Test (Patient Sequence Number 177→Patient Sequence Number 342)

N=84

Clinical pregnant fresh transfer n=24

Not pregnant n=21

From the same patients we also had access to:

Compromised on d3 n=15

Pregnant after FRET n=11

Not pregnant after FRET n=13

→Screen the novel patented genes in an inter/intra-patient setting for pregnancy and embryo development prediction →6 genes out of the "45 gene" list tested: ALDH1L2, ASNS, GOT1, NPR1, SLC6A9, SLIT2

Results

First pregnancy prediction model: all pregnant (n=24+11) vs all non-pregnant (n=21+13)

→1 gene model (ASNS)/Accuracy 62%/Roc curve with AUC 0.60

Additional analyses on Jun. 17, 2018:

Pregnancy Prediction in Frozen Cycles (Excluding Possible Endometrium Effect):

A model built to distinguish successful frozen embryo transfers from unsuccessful frozen embryo transfers: pregnant FRET (n=11) vs non-pregnant FRET (n=13), # pat=17

→2 gene model (SLC6A9. NPR1)/Accuracy 83%/Roc curve with AUC 0.8182

Embryo Development Prediction:

A model will be built to distinguish the embryos that were compromised at day 3 from all the transferred embryos: compromised d3 (n=15) vs all others transferred (n=69), # pat=

→3 gene model (ALDH1L2, GOT1. NPR1)/Accuracy 73%/Roc curve with AUC 0.7614

Example 9

Comparison Pregnant after FRET Vs Non-Pregnant after FRET

In this example, a comparison was between pregnant and non-pregnant after FRET was made using the gene model of example 8, i.e. comprising ALDH1L2, SLC6A9, ASNS, GOT1, SLIT2 and NPR1, supplemented with a normalization factor.

Formula of Selected Model:

$$\text{Pregnant} = -3.14387 - 1.61656*\text{GOT1} + 0.45089*\text{Normalisation factor} + 0.621*\text{SLC6A9}$$

A positive value for "pregnant" is predicted to lead to pregnancy, whereas a negative value is predicted to not lead to pregnancy.

Summary of Predictions:

|  | Predicted - Not pregnant | Predicted - Pregnant |
|---|---|---|
| Not Pregnant | 12 | 1 |
| Pregnant | 3 | 8 |

PPV: 88.9
NPV: 80
Sensitivity: 72.7
Specificity: 92.3

Example 10

Comparison Successful Transfer Vs Non-Successful Transfer

In this example, a comparison was between successful embryo transfer and non-successful embryo transfer was made using the gene model of example 8, i.e. comprising ALDH1L2. SLC6A9, ASNS, GOT1, SLIT2 and NPR1, supplemented with a normalization factor.

Formula of Selected Model:

$$\text{Successful} = -2.20342 - 0.34887*\text{NPR1} + 0.5048*\text{SLIT2} + 0.39441*\text{SLC6A9} + 0.12466*\text{Normalisation factor}$$

A positive value for "successful" is predicted to lead to embryo transfer, whereas a negative value is predicted to not lead to embryo transfer.

Summary of Predictions:

|  | Predicted - Non Successful | Predicted - Successful |
|---|---|---|
| Non Successful | 13 | 2 |
| Successful | 22 | 47 |

PPV: 95.9
NPV: 37.1
Sensitivity: 68.1
Specificity: 86.7

REFERENCES

Glujovsky D, Blake D, Farquhar C. Bardach A. Cleavage stage versus blastocyst stage embryo transfer in assisted reproductive technology. Cochrane Database Syst Rev. 2012 Jul. 11; 7

Wathlet S, Adriaenssens T, Segers I, Verheyen G, Janssens R. Coucke W, Devroey P and Smitz J, New candidate genes to predict pregnancy outcome in single embryo transfer cycles when using cumulus cell gene expression, Fertil Steril 98, 432-439, 2012.

TABLE 13

LIST OF GENES

| Abbreviation | Full Name | NCBI Gene ID |
|---|---|---|
| HSPH1 | heat shock 105 kDa/110 kDa protein 1 | 10808 |
| CAMK1D | calcium/calmodulin-dependent protein kinase ID | 57118 |
| PTGS2 | prostaglandin-endoperoxide synthase 2 (prostaglandin G/H synthase and cyclooxygenase) | 5743 |
| EFNB2 | ephrin-B2 | 1948 |
| GSTA4 | glutathione S-transferase alpha 4 | 2941 |
| STC1 | stanniocalcin 1 | 6781 |
| STC2 | stanniocalcin 2 | 8614 |
| VCAN | versican | 1462 |
| PGR | progesterone receptor | 5241 |
| GSTA3 | glutathione S-transferase alpha 3 | 2940 |
| GPX3 | glutathione peroxidase 3 (plasma) | 2878 |
| MROH9 | maestro heat-like repeat family member 9 | 80133 |
| RABGAP1L | RAB GTPase activating protein 1-like | 9910 |
| SLC7A11 | solute carrier family 7 (anionic amino acid transporter light chain, xc- system), member 11 | 23657 |
| ALDH1L2 | aldehyde dehydrogenase 1 family, member L2 | 160428 |
| ASNS | asparagine synthetase (glutamine-hydrolyzing) | 440 |
| BTNL3 | butyrophilin-like 3 | 10917 |
| TICRR | TOPBP1-interacting checkpoint and replication regulator | 90381 |
| CHTOP | chromatin target of PRMT1 | 26097 |
| CDC42EP3 | CDC42 effector protein (Rho GTPase binding) 3 | 10602 |
| CEBPG | CCAAT/enhancer binding protein (C/EBP), gamma | 1054 |
| DNAH3 | dynein, axonemal, heavy chain 3 | 55567 |
| DOCK9 | dedicator of cytokinesis 9 | 23348 |
| GALNTL6 | UDP-N-acetyl-alpha-D-galactosamine: polypeptide N-acetylgalactosaminyltransferase-like 6 | 442117 |
| GATS | GATS, stromal antigen 3 opposite strand | 352954 |
| GOT1 | glutamic-oxaloacetic transaminase 1, soluble (aspartate aminotransferase 1) | 2805 |
| HINT3 | histidine triad nucleotide binding protein 3 | 135114 |
| KLF10 | Kruppel-like factor 10 | 7071 |
| MBD3 | methyl-CpG binding domain protein 3 | 53615 |
| MOCOS | molybdenum cofactor sulfurase | 55034 |

TABLE 13-continued

LIST OF GENES

| Abbreviation | Full Name | NCBI Gene ID |
|---|---|---|
| MSR1 | macrophage scavenger receptor 1 | 4481 |
| NCOA7 | nuclear receptor coactivator 7 | 135112 |
| NPHP4 | nephronophthisis 4 | 261734 |
| NPR1 | natriuretic peptide receptor A/guanylate cyclase A (atrionatriuretic peptide receptor A) | 4881 |
| PAK7 | p21 protein (Cdc42/Rac)-activated kinase 7 | 57144 |
| PHGDH | phosphoglycerate dehydrogenase | 26227 |
| RNF166 | ring finger protein 166 | 115992 |
| ROBO2 | roundabout, axon guidance receptor, homolog 2 (*Drosophila*) | 6092 |
| SASH1 | SAM and SH3 domain containing 1 | 23328 |
| SLC6A9 | solute carrier family 6 (neurotransmitter transporter, glycine), member 9 | 14664 |
| SLIT2 | slit homolog 2 (*Drosophila*) | 9353 |
| SPTBN5 | spectrin, beta, non-erythrocytic 5 | 51332 |
| TSC22D3 | TSC22 domain family, member 3 | 1831 |
| TUBA1A | tubulin, alpha 1a | 7846 |
| UNC80 | unc-80 homolog (*C. elegans*) | 285175 |

What is claimed is:

1. A method of implanting an embryo in a female, said method comprising the steps of:
   (a) collecting oocytes with their cumulus and/or granulosa cells from a female having undergone an ovarian stimulation treatment;
   (b) measuring in the cumulus and/or granulosa cells from the oocytes, exon levels of gene expression from glutamic-oxaloacetic transaminase 1 (GOT1);
   (c) making intra-patient based comparison of said measurements of said exon levels of gene expression in the cumulus and/or granulosa cells from the oocytes;
   (d) ranking each of said oocytes based on said exon levels of expression in the cumulus and/or granulosa cells from each of said oocytes;
   (e) based on said ranking, determining each of said oocytes' competence to lead to childbirth, to implantation, to form a pre-implantation blastocyst or embryo, and/or to lead to fertilization;
   (f) selecting the oocyte having the highest competence, as being the oocyte having the highest chance of viable pregnancy after fertilization;
   (g) fertilizing the oocyte having the highest competence as determined in (f) to provide an embryo; and
   (h) implanting the embryo in the female.

2. The method of claim 1, wherein said ovarian stimulation treatment is selected from the group consisting of Luteinizing hormone and analogs thereof, Chorionic Gonadotrophins and analogs thereof, FSH and agonists thereof, GnRH and GnRH analogs associated with recombinant FSH and/or hMG, Epidermal growth factor (EGF) and analogs thereof, EGF-like proteins, amphiregulin, epiregulin, betacellulin and analogs thereof, Interleukin-6, Interleukin-1, Leukemia Inhibitory Factor (LIF), Phosphodiesterase type 4 Inhibitors, Low Molecular weight compounds activating any of the foregoing, clomiphene citrate, tamoxifen, letrozole; and any combinations of the foregoing.

3. The method according to claim 1, wherein the exon level analysis of gene expression further comprises measuring in the cumulus or granulosa cells from the oocytes exon levels of gene expression from one or more additional genes selected from the group consisting of HSPH1, CAMK1D, PTGS2, EFNB2, GSTA4, STC1, STC2, VCAN, PGR, GSTA3, GPX MROH9, RABGAP1L, SLC7A11, ALDH1L2, ASNS, BTNL3, TICRR, CHTOP, CDC42EP3, CEBPG, DNAH3, DOCKS, GALNTL6, GATS, HINT3, KLF10, MBD3, MOCOS, MSR1, NCOA7, NPHP4, NPR1, PAK7, PHGDH, RNF166, ROBO2, SASH1, SCL6A9, SLIT2, SPTBN5, TSC22D3, TUBA1A, and UNC80.

4. The method according to claim 3, wherein said one or more additional genes are selected from the group consisting of SLC6A9, SASH1, CAMK1D, EFBN2, and HSPH1.

5. The method according to claim 1, further comprising the step of normalizing the exon levels of gene expression of said gene.

6. The method according to claim 1, wherein measuring the exon levels of gene expression of said gene comprises measuring polynucleotide levels of said gene by means of biological assays using primers and/or probes capable of specifically hybridizing to said polynucleotide or to one or more regions within said polynucleotide.

7. The method according to claim 1, wherein measuring the exon levels of gene expression of said gene comprises measuring protein levels of related gene products by means of biological assays using binders, antibodies, or fragments thereof for said proteins, their pro-forms, or their metabolites.

* * * * *